(12) United States Patent
Truong et al.

(10) Patent No.: US 11,053,289 B2
(45) Date of Patent: Jul. 6, 2021

(54) BUDDING YEAST WITH HUMAN CHROMATIN

(71) Applicant: New York University, New York, NY (US)

(72) Inventors: David M. Truong, New York, NY (US); Jef D. Boeke, New York, NY (US)

(73) Assignee: New York University, New York, NY (US)

( * ) Notice: Subject to any disclaimer, the term of this patent is extended or adjusted under 35 U.S.C. 154(b) by 231 days.

(21) Appl. No.: 16/042,417

(22) Filed: Jul. 23, 2018

(65) Prior Publication Data
US 2019/0023752 A1 Jan. 24, 2019

Related U.S. Application Data

(60) Provisional application No. 62/535,575, filed on Jul. 21, 2017.

(51) Int. Cl.
*C07K 14/395* (2006.01)
*C07K 14/47* (2006.01)
*C12Q 1/02* (2006.01)

(52) U.S. Cl.
CPC ............ *C07K 14/395* (2013.01); *C07K 14/47* (2013.01); *C12Q 1/025* (2013.01)

(58) Field of Classification Search
CPC ....... C07K 14/395; C07K 14/47; C12Q 1/025
See application file for complete search history.

(56) References Cited

U.S. PATENT DOCUMENTS

2011/0152122 A1* 6/2011 Berger .................... C40B 40/08
506/10

OTHER PUBLICATIONS

McBurney et al., Divergent Residues Within Histone H3 Dictate a Unique Chromatin Structure in *Saccharomyces cerevisiae*, Jan. 2016, Genetics, vol. 202, pp. 341-349 (Year: 2016).*

Hamza, A., et al., Complementation of Yeast Genes with Human Genes as an Experimental Platform for Functional Testing of Human Genetic Variants, Genetics Society of America, vol. 201, pp. 1263-1274, Nov. 2015.

Osborn, M., et al., Rescuing yeast mutants with human genes, Briefings in Functional Genomics and Proteomics, vol. 6., No. 2, pp. 104-111, Aug. 13, 2007.

Kachroo, A., et al., Systematic humanization of yeast genes reveals conserved functions and genetic modularity, Science. Author manuscript, vol. 348, Issue 6237, pp. 921-925, May 22, 2015.

* cited by examiner

*Primary Examiner* — Mindy G Brown
*Assistant Examiner* — Khaleda B Hasan
(74) *Attorney, Agent, or Firm* — Hodgson Russ LLP

(57) ABSTRACT

Yeast having modified chromosomes are provided. The chromosomes are modified such that at least one of yeast histones H3, H4, H2A or H2B are fully or partially replaced by their human histone counterparts H3, H4, H2A or H2B, respectively. Histone amino acid substitutions are included. Cell fusions with the yeast having the modified chromosomes and non-yeast cells are provided. Methods for screening test agents using the yeast are also provided. Yeast with a mutated yeast DAD1 gene, the mutated DAD1 gene encoding an E50D mutation in yeast DAD1 protein, are provided, and provide a useful genetic background for making the yeast with partially or fully replaced histone(s).

5 Claims, 28 Drawing Sheets
(23 of 28 Drawing Sheet(s) Filed in Color)
Specification includes a Sequence Listing.

SEQUENCE LISTING

```
<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
ggtaacagct ctagtacctt cagag                                      25

<210> SEQ ID NO 2
<211> LENGTH: 17
<212> TYPE: DNA
<213> ORGANISM: Artificial Sequence
<220> FEATURE:
<223> OTHER INFORMATION: Primer

<400> SEQUENCE: 2
gccgaaaaga aaccagc                                               17

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aggtggtaaa gctggttcag                                            20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
```

```
ttcttgagaa gccttggtag c                                              21

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gctgccagaa aatccgcc                                                  18

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
gccaacttga tatccttctt ttggatagt                                      29

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
agaggtaaag gtggtaaagg tcta                                           24

<210> SEQ ID NO 8
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(13)
<223> OTHER INFORMATION: n is a, c, g, or t

<400> SEQUENCE: 8
ggatttcaag acngctctga c                                              21

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gtaacagcct tggtaccttc ag                                             22

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
aaccagctaa gtctgctcca g                                              21
```

```
<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
agaggtaagc aaggtggtaa gg                                              22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cttacccTta gccttgtggt g                                               21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aggctgctag aaagtctgct                                                 20

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tctcttagcg tggatagcac a                                               21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
ggtggtaagg gtttgggtaa g                                               21

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
gaaaaccttc aaaacacctc tggt                                            24

<210> SEQ ID NO 17
<211> LENGTH: 136
<212> TYPE: PRT
<213> ORGANISM: artificial sequence
<220> FEATURE:
<223> OTHER INFORMATION: swapp back mutation histone
```

<400> SEQUENCE: 17

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Lys Lys Asp Ile Lys Leu Ala
        115                 120                 125

Arg Arg Ile Arg Gly Glu Arg Ala
    130                 135

<210> SEQ ID NO 18
<211> LENGTH: 130
<212> TYPE: PRT
<213> ORGANISM: artificial sequence
<220> FEATURE:
<223> OTHER INFORMATION: swap back mutation histone

<400> SEQUENCE: 18

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Val Leu Pro Asn Ile
            100                 105                 110

His Gln Asn Leu Leu Pro Lys Lys Thr Glu Ser His His Lys Ala Lys
        115                 120                 125

Gly Lys
    130

<210> SEQ ID NO 19
<211> LENGTH: 6
<212> TYPE: PRT
<213> ORGANISM: Homo sapiens

<400> SEQUENCE: 19

Ile Ser Gly Phe Lys Lys
1               5

-continued

<210> SEQ ID NO 20
<211> LENGTH: 94
<212> TYPE: PRT
<213> ORGANISM: Artificial Sequence
<220> FEATURE:
<223> OTHER INFORMATION: DAD1-E50D mutation in DAD1 protein

<400> SEQUENCE: 20

Met Met Ala Ser Thr Ser Asn Asp Glu Glu Lys Leu Ile Ser Thr Thr
1               5                   10                  15

Asp Lys Tyr Phe Ile Glu Gln Arg Asn Ile Val Leu Gln Glu Ile Asn
            20                  25                  30

Glu Thr Met Asn Ser Ile Leu Asn Gly Leu Asn Gly Leu Asn Ile Ser
        35                  40                  45

Leu Asp Ser Ser Ile Ala Val Gly Arg Glu Phe Gln Ser Val Ser Asp
    50                  55                  60

Leu Trp Lys Thr Leu Tyr Asp Gly Leu Glu Ser Leu Ser Asp Glu Ala
65                  70                  75                  80

Pro Ile Asp Glu Gln Pro Thr Leu Ser Gln Ser Lys Thr Lys
                85                  90

<210> SEQ ID NO 21
<211> LENGTH: 5
<212> TYPE: PRT
<213> ORGANISM: artificial sequence
<220> FEATURE:
<223> OTHER INFORMATION: yeast chromosome containing human amino acids

<400> SEQUENCE: 21

Ser Ala Lys Ala Thr
1               5

<210> SEQ ID NO 22
<211> LENGTH: 4
<212> TYPE: PRT
<213> ORGANISM: artificial sequence
<220> FEATURE:
<223> OTHER INFORMATION: yeast chromosome with human amino acids

<400> SEQUENCE: 22

Ser Gln Glu Leu
1

<210> SEQ ID NO 23
<211> LENGTH: 11
<212> TYPE: PRT
<213> ORGANISM: artificial sequence
<220> FEATURE:
<223> OTHER INFORMATION: yeast chromosome with human amino acids

<400> SEQUENCE: 23

Ser Ala Lys Ala Glu Lys Lys Pro Ala Ser Lys
1               5                   10

<210> SEQ ID NO 24
<211> LENGTH: 8
<212> TYPE: PRT
<213> ORGANISM: artificial sequence
<220> FEATURE:
<223> OTHER INFORMATION: yeast chromosome with human amino acids

<400> SEQUENCE: 24

Lys Lys Thr Ser Thr Ser Thr Asp
1               5

```
<210> SEQ ID NO 25
<211> LENGTH: 5
<212> TYPE: PRT
<213> ORGANISM: homo sapiens

<400> SEQUENCE: 25

Thr Glu Ser His His
1               5

<210> SEQ ID NO 26
<211> LENGTH: 7
<212> TYPE: PRT
<213> ORGANISM: homo sapiens

<400> SEQUENCE: 26

Pro Glu Val Ser Ser Lys Gly
1               5

<210> SEQ ID NO 27
<211> LENGTH: 8
<212> TYPE: PRT
<213> ORGANISM: Homo Sapiens

<400> SEQUENCE: 27

Val Val Lys Thr Gln Lys Lys Glu
1               5
```

US 11,053,289 B2

BUDDING YEAST WITH HUMAN CHROMATIN

CROSS REFERENCE TO RELATED APPLICATIONS

This application claims priority to U.S. Provisional Application No. 62/535,575, filed on Jul. 21, 2017, the disclosure of which is hereby incorporated by reference.

SEQUENCE LISTING

The instant application contains a Sequence Listing which has been submitted electronically in ASCII format and is hereby incorporated by reference in its entirety. Said ASCII copy, created on Feb. 8, 2021, is named Revised_BTSequence_2_ST25.txt and is 7,938 bytes in size.

STATEMENT REGARDING FEDERALLY SPONSORED RESEARCH

This invention was made with government support under Grant No. 5F32GM116411 awarded by the National Institute of Health. The government has certain rights in the invention.

FIELD

The present disclosure relates generally to modified yeast, and more specifically to budding yeast modified to contain modified chromatin via humanization of histones.

BACKGROUND

*Saccharomyces cerevisiae* (budding yeast) is a single-cell eukaryote with a simple chromatin environment. The use of yeast as a "chassis" for other organism's chromatin, such as that from humans or pathogenic fungi, could provide a foundational tool for studying chromatin related complexes. Chromatin is important for regulating many aspects of cell biology, including chromosomes and gene transcription. There is an ongoing and unmet need for improved yeast that have modified chromatin for use in numerous applications. The present disclosure is pertinent to this need.

SUMMARY

Humans and yeast are separated by a billion years of evolution, yet their conserved core histones retain central roles in gene regulation. In the present disclosure, we "reset" yeast to use core human nucleosomes in lieu of their own, an exceedingly rare event which initially took twenty days. The cells adapt, however, by acquiring suppressor mutations in cell-division genes, or by acquiring certain aneuploidy states. Robust growth was also restored by converting certain histone residues back to their yeast counterparts, as explained further below. Data provided herein reveals that humanized nucleosomes in yeast are positioned according to endogenous yeast DNA sequence and chromatin-remodeling network, as judged by a yeast-like nucleosome repeat length. However, human nucleosomes have higher DNA occupancy and reduce RNA content. Adaptation to new biological conditions presented a special challenge for these cells due to slower chromatin remodeling. This humanized yeast provides a platform to study histone variants via yeast epigenome reprogramming, as well as other and diverse uses, as described further below. In embodiments, the disclosure provides yeast that have a mutated yeast DAD1 gene, the mutated DAD1 gene encoding an E50D mutation in yeast DAD1 protein. In embodiments, yeast with a mutated DAD1 gene background as described herein comprise one or more modified yeast chromosomes that are modified such that at least one of yeast histones H3, H4, H2A or H2B are fully or partially replaced by human histone H3, H4, H2A or H2B. In certain embodiments, a yeast chromosome in modified yeast of this disclosure comprises a partially replaced yeast H3 histone comprising the sequence: MARTKQTARKSTGGKAPRKQLAT-KAARKSAPATGGVKKPHRYRPGTVALREIRRY QKS-TELLIRKLPFQRLVREIAQDFKTDLRFQS-SAVMALQEACEAYLVGLFEDTNLCAI HAKRVTIMKKDIKLARRIRGERA (SEQ ID NO:17), wherein the enlarged and bold font indicates yeast residues swapped into the human histone sequence.

In certain embodiments, a yeast chromosome in modified yeast of this disclosure comprises a partially replaced yeast H2 yeast histone comprising the sequence: MSGRGKQGGKARA-KAKTRSSRAGLQFPVGRVHRLLRKGNY-AERVGAGAPVYLAA VLEYLTAEILELAG-NAARDNKKTRIIPRHLQLAIRNDEELNKLLGKVTIA QGGVLPNI HQNLLPKKTESHHKAKGK (SEQ ID NO:18), wherein the enlarged and bold font indicates yeast residues swapped into the human histone sequence.

Methods of making the modified yeast of this disclosure are included. Modified yeast cells fused with non-yeast eukaryotic cells are included.

BRIEF DESCRIPTION OF FIGURES

The patent or application file contains at least one drawing executed in color. Copies of this patent or patent application publication with the color drawings will be provided by the Office upon request and payment of the necessary fee.

In FIG. 1A, the sequence SAKAT is SEQ ID NO:21; the sequence SQEL is SEQ ID NO:22; the sequence SAKAEKKPASK is SEQ ID NO:23; the sequence KKTSTSTD is SEQ ID NO:24, the sequence TESHH is SEQ ID NO:25; the sequence PEVSSKG is SEQ ID NO:26; and the sequence VVKTQKKE is SEQ ID NO:27. (B) Dual-histone plasmid shuffle strategy (also see FIG. 8). (C) The "humanization frequency" by which each human histone gene in the context of the relevant histone pairs or all four histone genes complement deletions of the respective yeast counterpart was assessed as in (B). Spots show yeast 10-fold serial dilutions. The densest spot contains $10^5$ yeast. (D) Yeasts with completely human nucleosomes arise after 20 or more days on plates. Only 8 colonies have been isolated thus far, referred to as "yHs". (E) PCRtag analysis of humanized yeast (Mitchell et al., 2015), and confirmed by sequencing extracted plasmids. The human histones differ in DNA sequences enough to enable straightforward PCR genotyping.

In FIG. 11A, the sequence SAKAT is SEQ ID NO:21; the sequence SQEL is SEQ ID NO:22; the sequence TESHH is SEQ ID NO:25. (B) Regions 1, 2, and 4 were partitioned into further systematic swap-backs. (C) Complementation assays of swap strains from (B). (D) Three swapped-back residues each in the N-terminus (hH2A$_N$) or C-terminus (hH2A$_C$) of human histone H2A (hH2A) enhanced humanization frequency and growth rates in combination with human histone H2B (hH2B). (E) Graphic with the combination of all six swapped-back residues (hH2A$_{NC}$), which is optimal.

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all steps and compositions of matter described herein in the text and figures of this disclosure, including all such steps individually and in all combinations thereof, and includes all compositions of matter including but not necessarily limited to all yeast strains, progeny of the yeast, fusions of yeast cells and non-yeast cells, progeny of yeast cell cultures, and the medium in which the modified yeast are grown and/or preserved.

Because they serve as a central interface for hundreds of other proteins, histones are among the most conserved genes in eukaryotes (Talbert and Henikoff, 2010).

Figure 1:
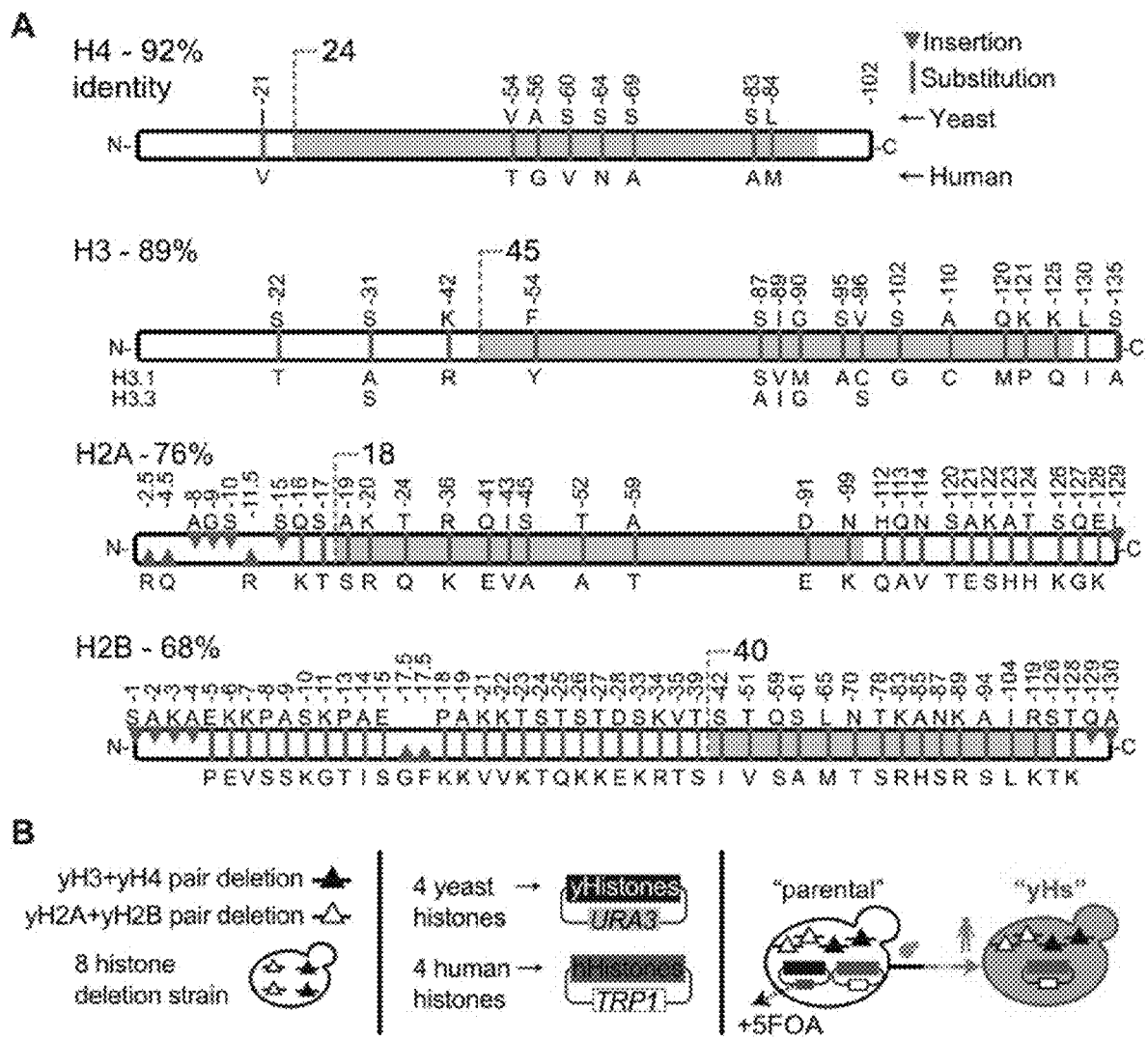
FIG. 1. *Saccharomyces cerevisiae* can subsist on completely human core nucleosomes. (A) Human and budding yeast histones share from 68 to 92% protein identity. Red bars indicate residue positions that differ between the two species. Numbers refer to the yeast histones. Gray colored regions show the globular histone domains, and the white regions show the N- and C-terminal tails.
Figure 1:
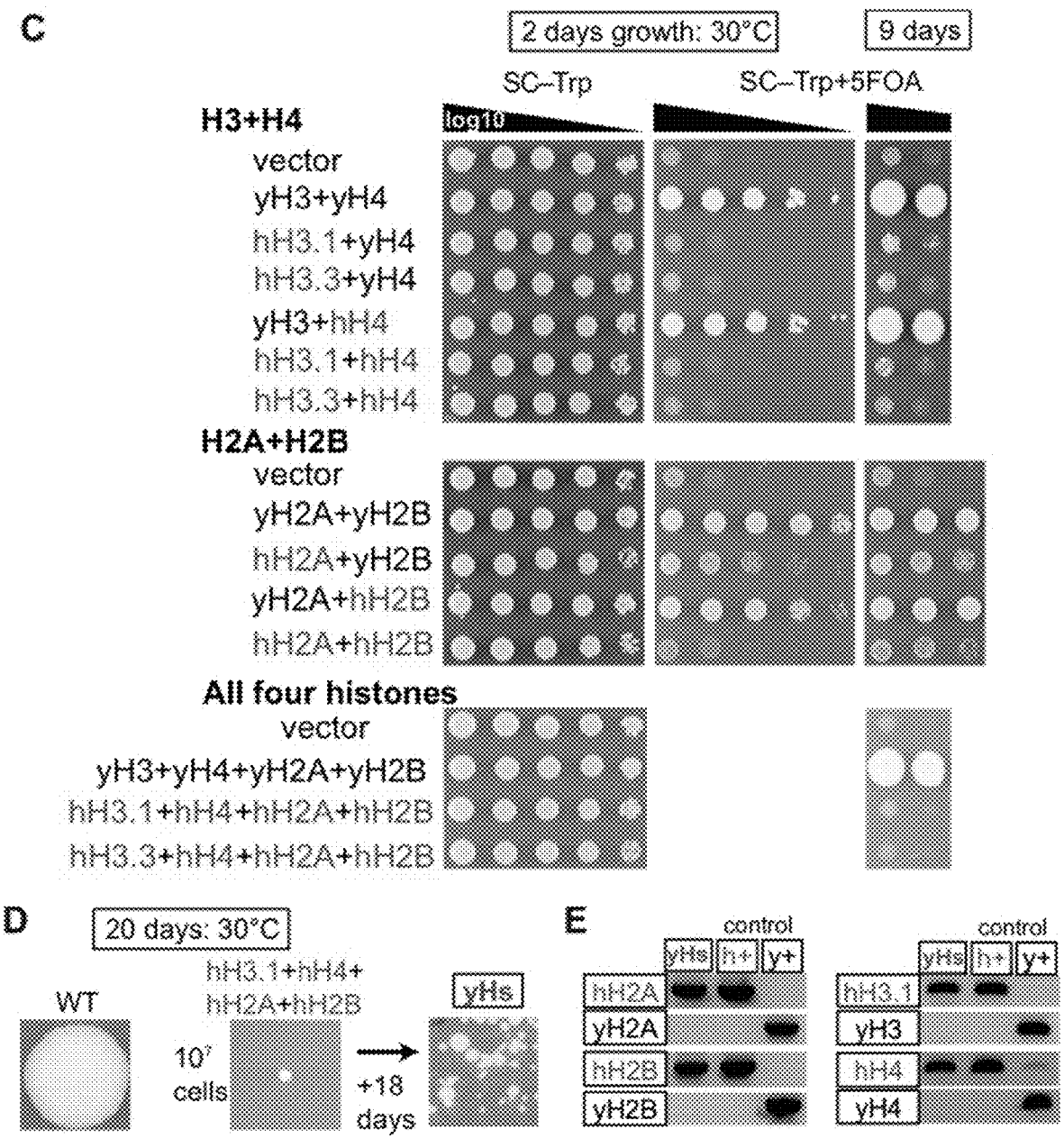

They serve central cellular roles by regulating genome access, DNA compaction, transcription, replication, and repair (Talbert and Henikoff, 2017). Whereas higher eukaryotes evolved myriad histone variants with specialized functions, *Saccharomyces cerevisiae* (budding yeast) encodes but a few, a simplicity that has facilitated many fundamental discoveries in chromatin biology (Rando and Winston, 2012). In this disclosure we investigated why budding yeast have streamlined chromatin compared to humans, and analyzed whether differences in histone sequences reflect functional divergence (FIG. 1A). Without intending to be constrained by any particular theory, it is considered that the disclosure demonstrates use of yeast serve as a "chassis" for understanding how histone variants exert control over cellular transcription. Thus, in embodiments, the disclosure relates to providing modified *S. cerevisiae* that utilizes core histones from humans. It is believed that, prior to the present disclosure, only single yeast genes have been individually humanized (Hamza et al., 2015; Kachroo et al., 2015; Laurent et al., 2016; Osborn and Miller, 2007), but never a whole protein complex, nor one of such central importance as histones. In this regard, the present disclosures could have revealed intrinsically different properties between yeast nucleosomes and those from humans. We initially suspected two possible outcomes: i) that human histones could be used in place of yeast histones because of their high conservation, suggesting that histone sequence divergence provides only minor functional differences; or ii) that human histones in yeast would very poorly complement or even fail entirely, suggesting that the divergent residues are highly optimized for each species and serve specialized or novel functions. Our results are consistent with the latter. In particular, the humanized yeast as described further below had pronounced delays in adapting to new environmental conditions, likely due to slowed remodeling of human core nucleosomes. In addition, our results suggest that human core nucleosomes may have evolved to occupy DNA more tenaciously, as we observed reduced RNA content and greater DNA occupancy by MNase-seq. Results presented herein suggest that yeast may maintain human chromatin even when given access to native yeast histones. This may represent a type of chromatin "memory", whereby cells partition and reproduce parental chromatin to new daughter cells. Thus, while the species-specific coevolution of histones and their associated protein networks is extensive, the present disclosure demonstrates that it is nonetheless possible to reprogram the epigenome of at least one organism to accept histones of a very distant relative.

In view of these results, the disclosure provides in certain aspects compositions and methods for modifying yeast chromatin, and yeast comprising modified chromatin. While these aspects are illustrated by fully and partially replacing histones of *Saccharomyces cerevisiae* with human histones, given the benefit of this disclosure, those skilled in the art can adapt these representative embodiments to generate modified yeast having endogenous histones fully or partially replaced, or optimized for any particular phenotype or other characteristics, with histones from a variety of other eukaryotic organisms/cell types. Such other eukaryotic organisms and cell types can include but are not necessarily limited to yeast other than *S. cerevisiae*, including for example, pathogenic fungi, or any other fungi of interest, any single-celled eukaryote such as amoeba, or any animal, including but not necessarily limited to mammals, and any plant.

In embodiments, the disclosure includes producing human artificial chromosomes (HACs) in yeast using the compositions and methods of this disclosure. Yeast comprising the HACs are also included. The HACs comprise yeast chromosomes that are modified such that at least one of yeast histones H3, H4, H2A or H2B are fully or partially replaced by their human histone counterparts, i.e., human H3, H4, H2A or H2B, respectively. Such yeast histone replacements can be adapted so that histones from any other cell eukaryotic cell type can be incorporated into yeast chromosomes.

Thus, in embodiments, the disclosure relates to replacing all or some histones or some portions of histones in budding yeast with some or all non-endogenous histone counterparts from a distinct organisms(s). As discussed above, in embodiments, the histone counterparts are human histones, which may comprise certain amino acid substitutions, as described further below. In embodiments, the human histone sequences in partially replaced yeast histones comprise one or more yeast histone amino acids from the yeast homologous histone (i.e., a swap-back mutation). Thus, a partially replaced yeast histone comprises a histone that is a non-yeast histone, but retains at least some yeast histone amino acids, when taken in context of the wild type yeast histone amino acid sequence. In embodiments, a partially replaced yeast histone comprises only, or at least, 1, 2, 3, 4, 5, 6, 7, 8, 9, 10, or more yeast amino acids, provided that the partially replaced yeast histone has an amino acid sequence that is distinct from an unmodified yeast histone amino acid sequence, and contains histone amino acids from a non-yeast source, such as human histones.

In embodiments, the human or other non-yeast chromosomes comprise histones that have one or more amino acid modifications. The modifications can comprise, for example, amino acid deletions, insertions, and substitutions. In embodiments, the human or other non-*S. cerevisiae* histone comprises a swapped-back amino acid, thus providing a partially humanized (or other non-*S. cerevisiae*) histone comprising *S. cerevisiae* and non-*S. cerevisiae* histone amino acids. Suitable swap-back mutations can be identified using approaches described herein, and all specific amino acid residue modifications identified herein, and all combinations of such modifications, are included in the invention. Any individual or combination of mutations can also be excluded from the invention.

Human and yeast histone amino acid sequences are known in the art. The disclosure includes all human and yeast histone amino acid sequences. Representative and non-limiting examples of human histone amino acid sequences are available via GenBank accessions numbers, as follows: H3.1-NP_003522.1; H3.3-NP_002098.1; H4-NP_003539.1; H2A.1-NP_003501.1; H2B.1-NP_066406.1. Representative and non-limiting examples of yeast histone amino acid sequences are available via GenBank accessions numbers, as follows: H3-NP_014367.1; H4-NP_014368.1; H2A-NP_010511.3; H2B-ONH73823.1. In embodiments, yeast H2 histone is fully or partially replaced with human H2A.1 or human H2B.1 histone. In embodiments, yeast H3 histone is fully or partially replaced with human H3.1 or H3.3 histone. In embodiments, yeast H4 histone is partially or fully replaced with human H4 histone.

All of the amino acid sequences associated with the GenBank accession numbers are incorporated herein by reference as they exist on the filing date of this application or patent. The disclosure includes amino acid sequences that are from 80%-99% similar to those amino acid sequences, and includes amino acid sequences that include insertions and deletions, provided yeast comprising such modified histones are viable. The disclosure includes all polynucleotide sequences encoding the histone proteins, and all sequences complementary to those sequences.

As is known in the art, by convention, human histone amino acid residue numbers generally do not include the Met in the residue numbering. In embodiments, for human H3, H4, and H2B, this convention is followed in this disclosure, with the exception of human H2A, for which the first Met is counted in the residue numbering, such as in FIGS. 3C and 11A.

In embodiments, the disclosure includes modified yeast comprising a mutation in the yeast DAD1 gene, such as a mutation that changes DAD1 at residue 50, such as an E to D amino acid substitution (referred to herein as DAD1-

E50D). As a consequence of this change, the yeast DAD1 protein comprises the following amino acid sequence: MMASTSNDEEKLISTTDKYFIEQRNIVLQEINETMN-SILNGLNGLNISLDSSIAVGREF QSVSDLWKTLYDG-LESLSDEAPIDEQPTLSQSKTK (SEQ ID NO:17) wherein the D at position 50 is in enlarged and bold font. In embodiments, the mutation in the DAD1 gene comprises a missese mutation in the DAD1 gene, as set forth in Table 1 below. Thus, in embodiments, yeast of this disclosure comprise a mutated DAD1 protein, wherein the protein comprises an E50D mutation.

In an embodiment, the disclosure comprise a modified yeast with a human H3 histone amino acid sequence, except for swapping back only two yeast amino acids. In an embodiment, such a sequence comprises an H3kk mutation comprising the sequence: MARTKQTARK-STGGKAPRKQLAT-KAARKSAPATGGVKKPHRYRPGTVALREIRRYQK STELLIRKLPFQRLVREIAQDFKTDLRFQS-SAVMALQEACEAYLVGLFEDTNLCAIHAKR VTIMKKDIKLARRIRGERA (SEQ ID NO:17), wherein the two yeast K amino acids swapped back to the human histone sequence are in enlarged, bold font. In this sequence, the yeast K amino acid replaces the human P and Q amino acids, respectively in the N to C direction. Per convention for this H3, the first Met is not counted, thus the positions in this amino acid sequence are K121 and K125. In an embodiment, the disclosure comprises a modified yeast with a human H2 histone (H2Ac) sequence comprising: MSGRGKQGGKARA-KAKTRSSRAGLQFPVGRVHRLLRKGNY-AERVGAGAPVYLAAVL EYLTAEILELAG-NAARDNKKTRIIPRHLQLAIRNDEELNKLLGKVTIA QGGVLPNIHQNL LPKKTESHHKAKGK (SEQ ID NO:18). In this sequence, the human QAV amino acids at positions 113, 114 and 115 (QAV) counting the first Met are replaced with HQN. The swapped back yeast amino acids are shown in enlarged, bold font.

In an embodiment, the disclosure provides a single epigenetic element, such as a YAC or other plasmid, encoding human histones H3.1, H3.3, H4, H2A, H2B, or histones comprising yeast swap back mutations or other amino acid changes as described herein, wherein the single epigenetic element is present in a yeast comprising the DAD1-E50D mutation.

In embodiments, modified yeast described herein comprise human histones with mutations selected from the following:
in human 113, a replacement of human H3 amino acids selected from:
human T22 with S; human R42 with K; human Y45 with F; human A87 with S; human A95 with S; human S96 with V; human G102 with S; human 110C with A; human 120M with Q, human 121P with K; human 125Q with K; human 130I with L; human 135A with S; and combinations thereof, and wherein optionally only human→yeast P121K and Q125K are changed;
and/or
in human 114, a replacement of human H4 amino acids selected from:
human T54 with V; human G56 with A; human V60 with S; human N64 with S; human A69 with S; human A82 with S; human M84 with L; and combinations thereof;
and/or
in human H2A
a deletion of at least one of R, Q and R in positions 3, 5 and 12, respectively, of the human H2A histone sequence; or a replacement of human H2A amino acids selected from: human K16 with Q; human T17 with S; human S19 with A; human R20 with K; human K36 with R; human E41 with Q; human V43 with I; human A45 with S; human A52 with T; human T59 with A; human E91 with D; human K99 with N; human Q112 with H; human A113 with Q; human V114 with N; human T115 with S; human S122 with K; human H123 with K; human H124 with T; human K126 with S; human G127 with S; human K128 with E; human V114 with N; and combinations thereof,
and/or;
in human H2B:
a deletion of one or both human H2B amino acids GF in the contiguous sequence ISGFKK (SEQ ID NO:19); and/or a replacement of human H2B amino acids selected from: human P5 with E; human E6 with K; human V7 with K; human S8 with P; human S9 with A human K10 with S; human G11 with K; human T13 with P; human 114 with A; human S15 with E; human K18 with P; human K19 with A; human V21 with K; human V22 with K; human K23 with T; human T24 with S; human Q25 with T; human K26 with S; human K27 with T; human E28 with D; human K33 with S; human R34 with K; human T35 with V; human S39 with T; human 142 with S; human V51 with T; human S59 with Q; human A61 with S; human M65 with L; human T70 with N; human S78 with T; human R83 with K; human H85 with A; human S87 with N; human R89 with K; human S94 with A; human L104 with I; human K119 with R; human T126 with S; human K128 with T;
and/or
any mutation listed in Table 1 or 2.

The disclosure also includes discovering, generating, and/or engineering mutations in other yeast genes (i.e., non-histone genes) that may suppress negative effects caused by or correlated with the presence of the non-endogenous histone(s). In embodiments, such suppressor mutations are present in genes directly or indirectly related to cell cycle regulation.

In embodiments, the disclosure comprises fusing a modified yeast cell comprising fully or partially modified histones with a distinct cell type, thereby facilitating "uploading" the modified chromosomes into the distinct cells. In embodiments, the distinct cell types are non-*S. cerevisiae* eukaryotic cells. In embodiments, the distinct cell types are non-*S. cerevisiae* fungi, including but not limited to pathogenic fungi. In embodiments, the distinct cell types to which modified yeasts of this disclosure are fused are animal cells. In embodiments, the cells are human, non-human primate, or porcine cells. In embodiments, the cells are stem cells. In embodiments, the stem cells are totipotent, pluripotent, multipotent, or oligopotent stem cells when the modified histones are introduced. In embodiments, the cells are pluripotent, and the pluripotency of the cells is induced, such as by using exogenous genes or compounds. In embodiments, the cells are neural stem cells. In embodiments, the cells are hematopoietic stem cells. In embodiments, the cells are leukocytes. In embodiments, the leukocytes are of a myeloid or lymphoid lineage. In embodiments, the cells are embryonic stem cells, or adult stem cells. In embodiments, the cells are epidermal stem cells or epithelial stem cells. In embodiments, the modified cells of this disclosure are allowed to differentiate, and/or are coaxed into differentiation, such as into an organism, organ, or tissue. In embodiments, the cells are differentiated cells when the modified histone(s) is/are introduced. In embodiments, the cells are cancer cells, or cancer stem cells. In certain approaches, cells produced according to this disclosure are maintained as cell lines.

In embodiments, cells of this disclosure comprise one or more histone mutations, and may be at least for a period of time heterozygous or homozygous for such mutated histones.

In certain embodiments, cells modified to comprise non-endogenous histones according to this disclosure are engineered to produce a protein or other compound, such as an antibody, and the cells themselves or the protein or compound they produce is used for prophylactic or therapeutic applications, or industrial applications, including but not necessarily limited to food and beverage technologies.

In embodiments, one or more histone mutations or other genes as described herein can be made by direct modification of an endogenous histone-encoding or other gene, such as by CRISPR-mediated gene editing. The histone mutants, or non-endogenous histone can also be introduced on a plasmid or "neochromosome", which comprises a yeast artificial chromosomes containing essential components for replication.

In certain approaches, cells modified according to this disclosure are such that they comprise fully or partially non-endogenous histones and are used for screening any of a wide variety of test compounds. In embodiments, the cells are modified such that the histones comprise, in addition to non-endogenous histone amino acid residues, at least one mutation or other genetic or metabolic feature that is causative of or is correlated with a particular disease, disorder, or condition.

In embodiments, a plurality of cells modified to comprise non-endogenous histones as described herein is contacted with distinct test agents, wherein a change in any characteristic of the cells as a result of being contacted with the test agent indicates the test agent is a candidate for eliciting a similar response in cells that are the source of the histones used to modify yeast of this disclosure. By way of non-limiting example, S. cerevisiae can be modified to comprise, for instance, full or partial histones that are endogenous to pathogenic fungi such as Candida spp., Pneumocystis spp., and/or Cryptococcus spp. Such modified budding yeast can be used to test candidate agents for use as anti-fungal agents, wherein the anti-fungal agent's cytostatic activity is at least partially attributable to the presence of the modified histones.

It will be clear to one skilled in the art that such screens are readily adaptable to high-throughput approaches, which furthermore can be fully or partially automated. In embodiments, the test agents are contacted with cultures of cells comprising histones modified as described herein, wherein the cell cultures comprise a liquid culture which is separated into a plurality of reaction chambers, such as in a high-throughput configuration. In an embodiment, the plurality of reaction chambers comprises up to or at least 1536 reaction chambers. Into each reaction chamber one or more test agents may be added, and a change in the cells in the cell culture due to the presence of the test agent can be observed, thereby identifying the test agent as a candidate for use in eliciting a similar change in non-modified cells that are the source of the modified histones in the cell culture. In an embodiment, a test agent is tested for killing and/or inhibiting the growth of, for example, yeast cells comprising histones from cancer cells.

The following Examples are intended to illustrate but not limit the disclosure.

Example 1

*Saccharomyces cerevisiae* can Subsist on Fully Human Core Histones

Figure 8:
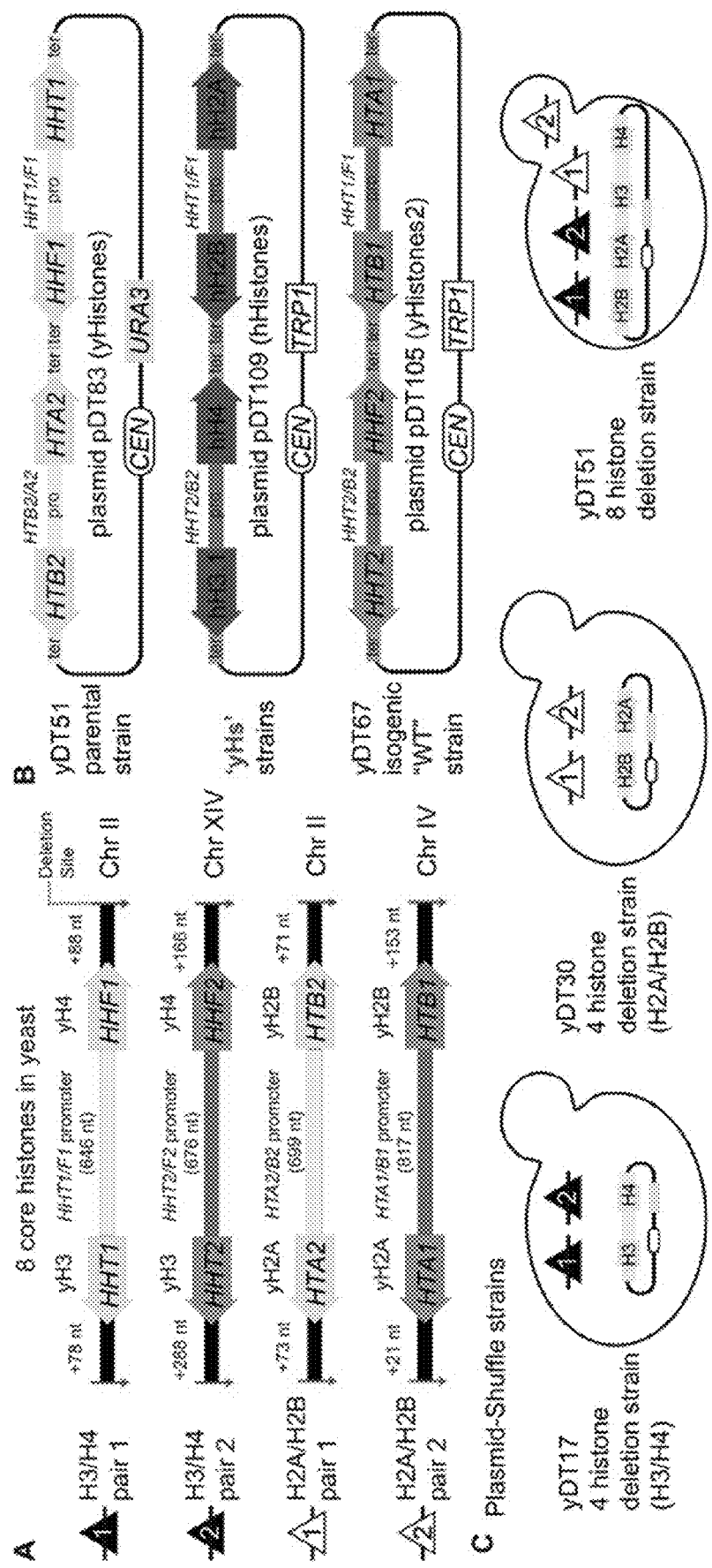
FIG. 8. Construction of yeast with completely human nucleosomes ('yHs'), Related to FIG. 1. (A) Map of histone genomic locations in yeast. Triangles show histone pairs deleted in (C). Red arrows indicate CRISPR/Cas9 deletion junctions. Different shades of green show the divergent histone promoters. (B) Diagram of main histone plasmids used in this study for the dual-plasmid histone shuffle. Note the different promoters/terminators used shown in different shades of green. (C) The three histone deletion strains used for humanization studies in FIG. 1C, and stabilizing plasmids as indicated. (D) PCRtag confirmation of yeast containing human histones H3.1/H3.3 and H4 (hH3.1/hH3.3 and hH4). (E) PCRtag confirmation of yeast containing human histones H2A and H2B (hH2A and hH2B). (F) PCRtag confirmation of the 8 yeast with completely human nucleosomes with the names "yHs" for "Yeast Homo Sapiens". (G) Colony growth rates for various "WT" versions of yeast that contain different complements of native yeast histone plasmids. (H) Demonstration of how rapidly "yHs" yeast accumulate suppressors and evolve towards faster growth.
Figure 8:
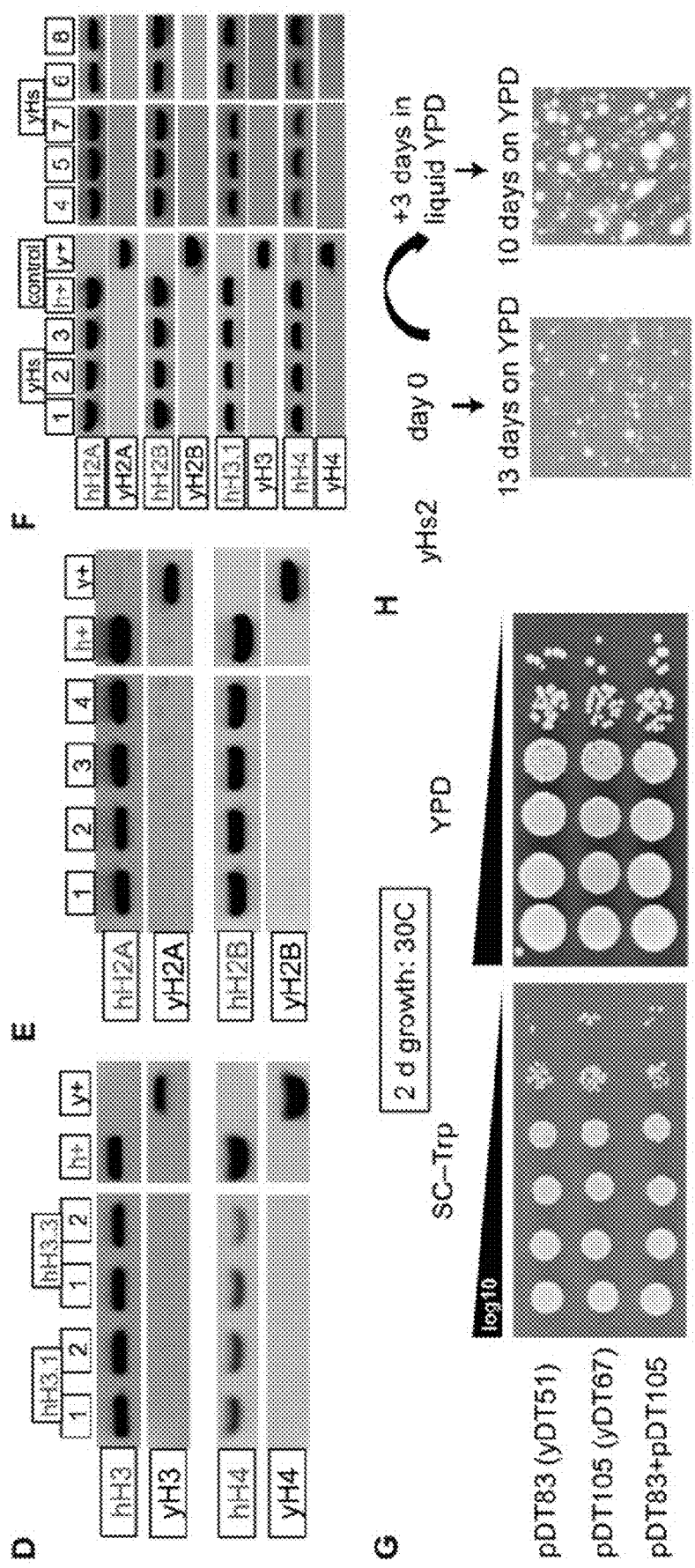

*S. cerevisiae* cells possess a relatively simple repertoire of histones. The core nucleosome, the four histones H3, H4, H2A, and H2B, comprise duplicate copies in the genome—each with divergent promoters and terminators—for a total of eight histone copies (Eriksson et al., 2012) (FIG. 8). Additionally, there are three histone variants, H2A.Z, CENPA, and H1 (HTZ1, CSE4, and HHO1, respectively), which were not altered here.

To humanize the core nucleosome of yeast, we constructed three strains in which the target histones of interest (e.g., all 8 core histones) were deleted from the genome. We then used a plasmid shuffle approach (i.e., yeast vs. human histones on plasmids) for quickly eliminating the native yeast histones in favor of their human counterparts, by 5-FOA counter-selection (Boeke et al., 1987) (FIGS. 1B and 8; see Methods). The dual plasmids, containing either human or yeast histone genes, are expressed from different sets of endogenous histone promoters and terminators to eliminate recombination. Any designed humanized histone strain will carry only half the target histone copies (e.g., 4 instead of 8 histones).

First, we determined the relative "humanization frequencies" (i.e., humanized colonies per cell plated) for individual or pairs of human histones. Human histone H4 (hH4) had the highest humanization frequency (fast growth, 20%), followed by hH2B (slow growth, 20%), hH2A (slow growth, $10^{-2}$), and finally hH3.1 and hH3.3 (very slow growth, $10^{-4}$ and $10^{-5}$ respectively) (FIG. 1C). Combining hH4 with either hH3.1 or hH3.3 also produced very slow growth (frequency of $10^{-4}$ and $10^{-5}$, respectively), whereas combining hH2A with hH2B led to slow growth, but a modest humanization frequency of ~$10^{-3}$. For both human histone combinations, we confirmed the loss of yeast histones by PCRtag analysis (Mitchell et al., 2015), which uses PCR to discriminate between sequence differences of yeast and human histones, and a lack-of histone mutations by Sanger sequencing of recovered plasmids (FIG. 8D, E).

We then attempted to exchange all four histone genes simultaneously (FIG. 1C). An "isogenic-WT" strain (yDT67) that replaces one native yeast histone plasmid with a plasmid containing the other set of native histones "shuffled" readily (FIGS. 1C and 8). Yet neither plasmid encoding fully human core nucleosomes containing either hH3.1 or hH3.3 produced colonies within nine days. However, upon plating at least $10^7$ cells and waiting 20 days we did see colonies representing humanized yeast, but only for the hH3.1 plasmid (FIG. 1D). These humanized yeast colonies were confirmed via PCRtag analysis and sequencing of extracted plasmids (FIG. 1E), which showed no mutations in the human histones. These humanized colonies are unlikely to contain residual yeast histones, as "old"—histones turnover by at least two-fold per cell division (Annunziato, 2005; Radman-Livaj a et al., 2011). Since each haploid cell contains about 67,000 nucleosomes (Brogaard et al., 2012), and a small yeast colony contains at least $10^7$ cells, those underwent at least 23 cell divisions. Therefore, the cells contain on average 0.01 original yeast nucleosomes, assuming an infinite nucleosome/histone half-life.

Figure 9:
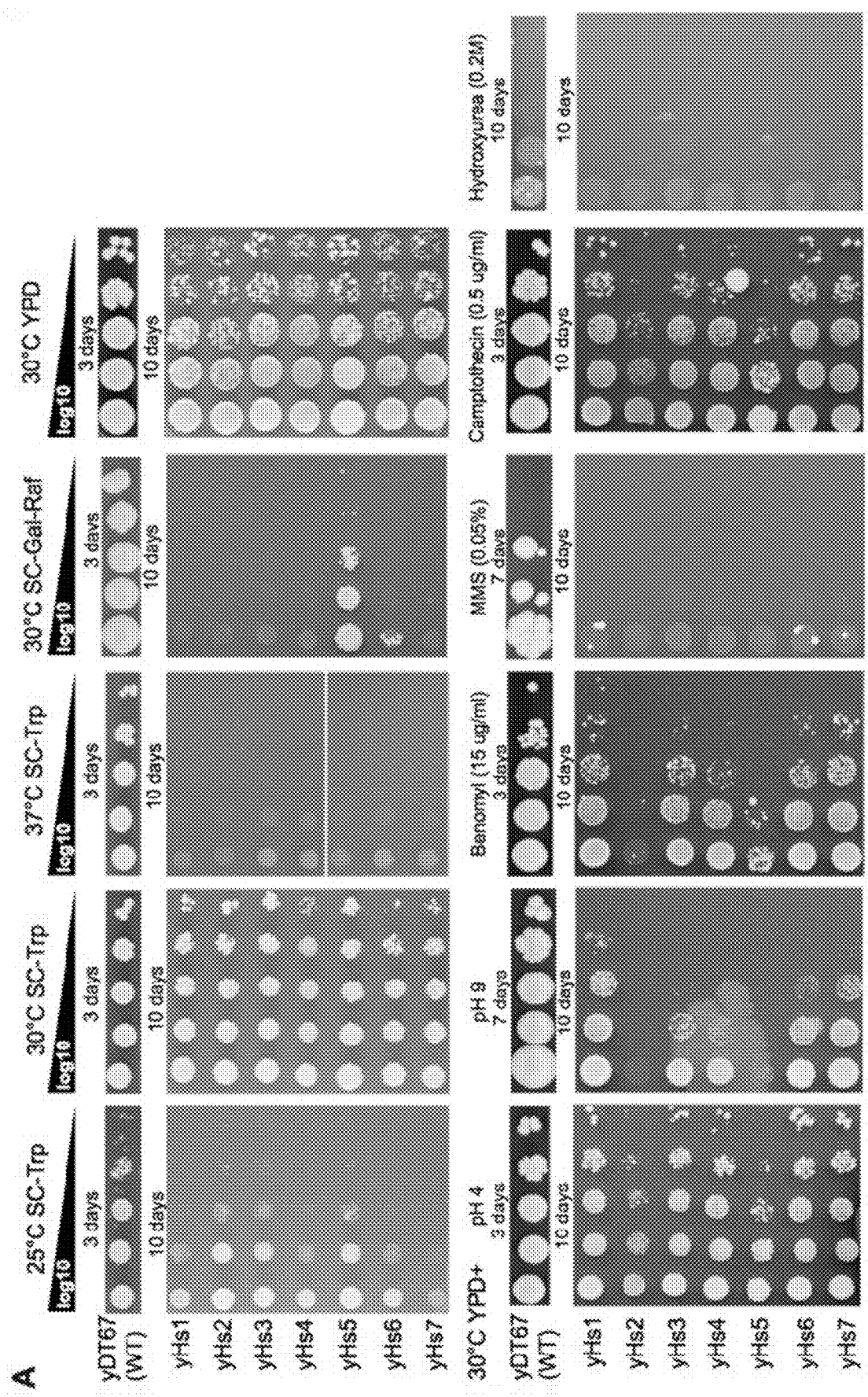
FIG. 9. Growth rates of 'yHs' strains and chromosomal aneuploidy, Related to FIGS. 1 and 2. (A) Growth of yHs1-7 on the following drugs and conditions: SC-Trp+2% dextrose, SC+1% raffinose and 2% galactose (respiration), YPD+2% dextrose, YPD+2% dextrose+either: HCl (pH 4.0; vacuole formation defects), NaOH (pH 9.0; vacuole formation defects), Benomyl (15 µg/ml; microtubule inhibitor), Methyl methanosulfate (MMS 0.05%; defective DNA repair), Camptothecin (0.5 µg/ml; topoisomerase inhibitor), and Hydroxyurea (0.2 M; defective DNA replication). (B) Mating tests of yHs1-7. Mated diploids were then sporulated. (C) Growth comparison of yHs1-7 from original colony isolates, maintenance strains (yHs-m), and evolved strains (yHsC5) on solid media for 3 and 7 days using 10-fold serial dilutions. Cells were normalized to an $A_{600}$ of 10. (D) None of the eight yHs lineages possess gross chromosomal abnormalities (deletions or insertions) as analyzed by pulsed-field gel electrophoresis. (E) Examples of chromosomal aneuploidies for 3 yHs lineages, including yHs7 (aneuploid) and yHs7C5i1, which showed no aneuploidies and acquired a mutation E50D in gene DAD1. Box-plots show read counts across each chromosome.
Figure 9:
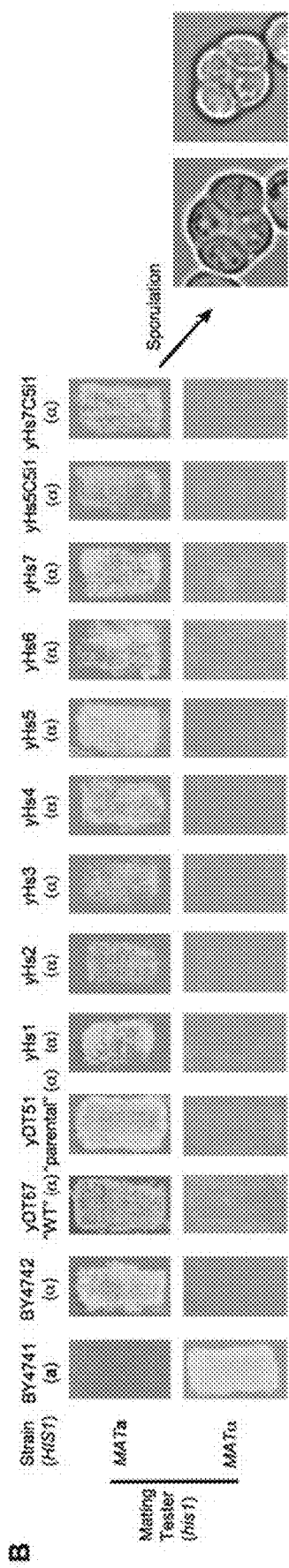
Figure 9:
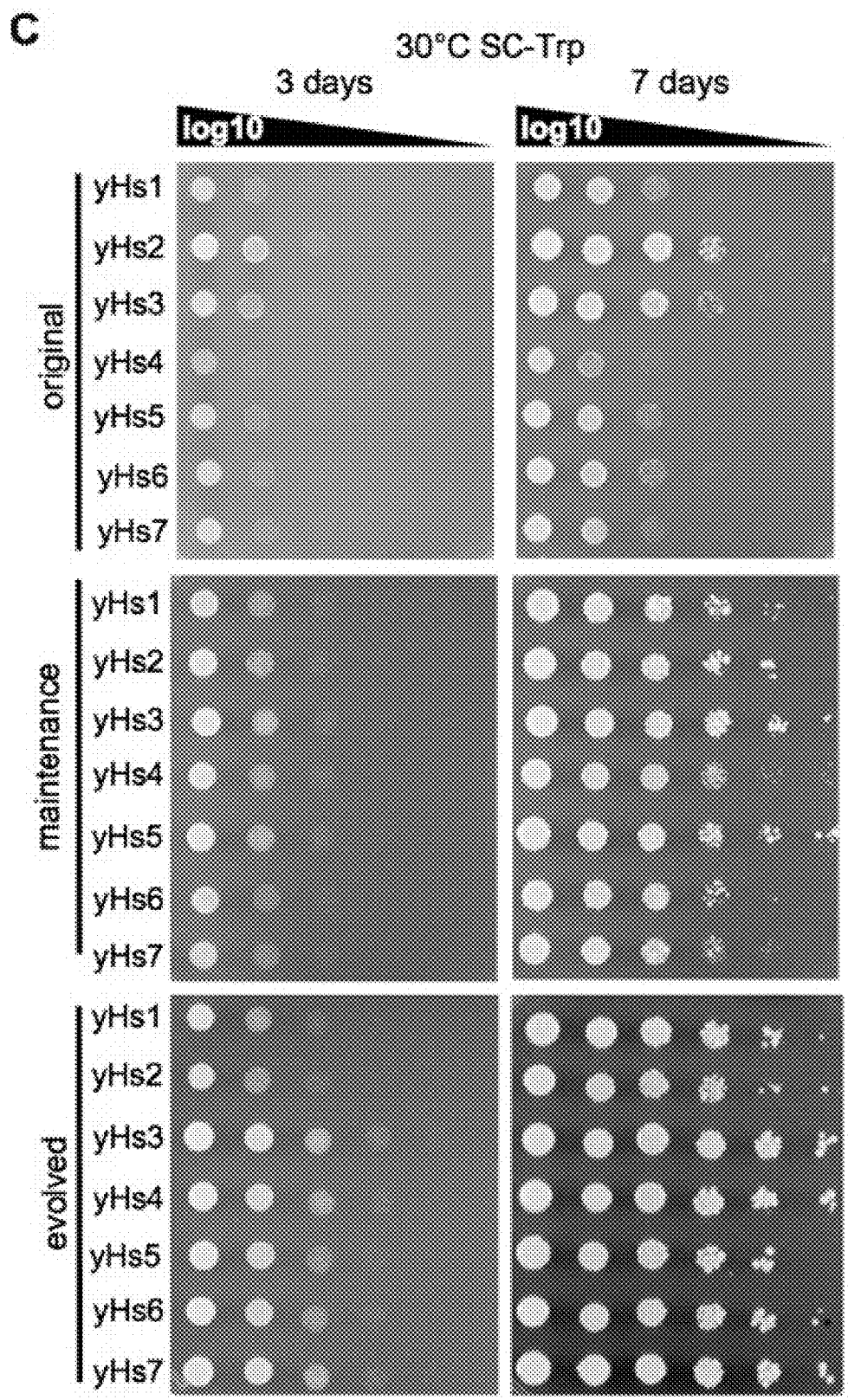
Figure 9:
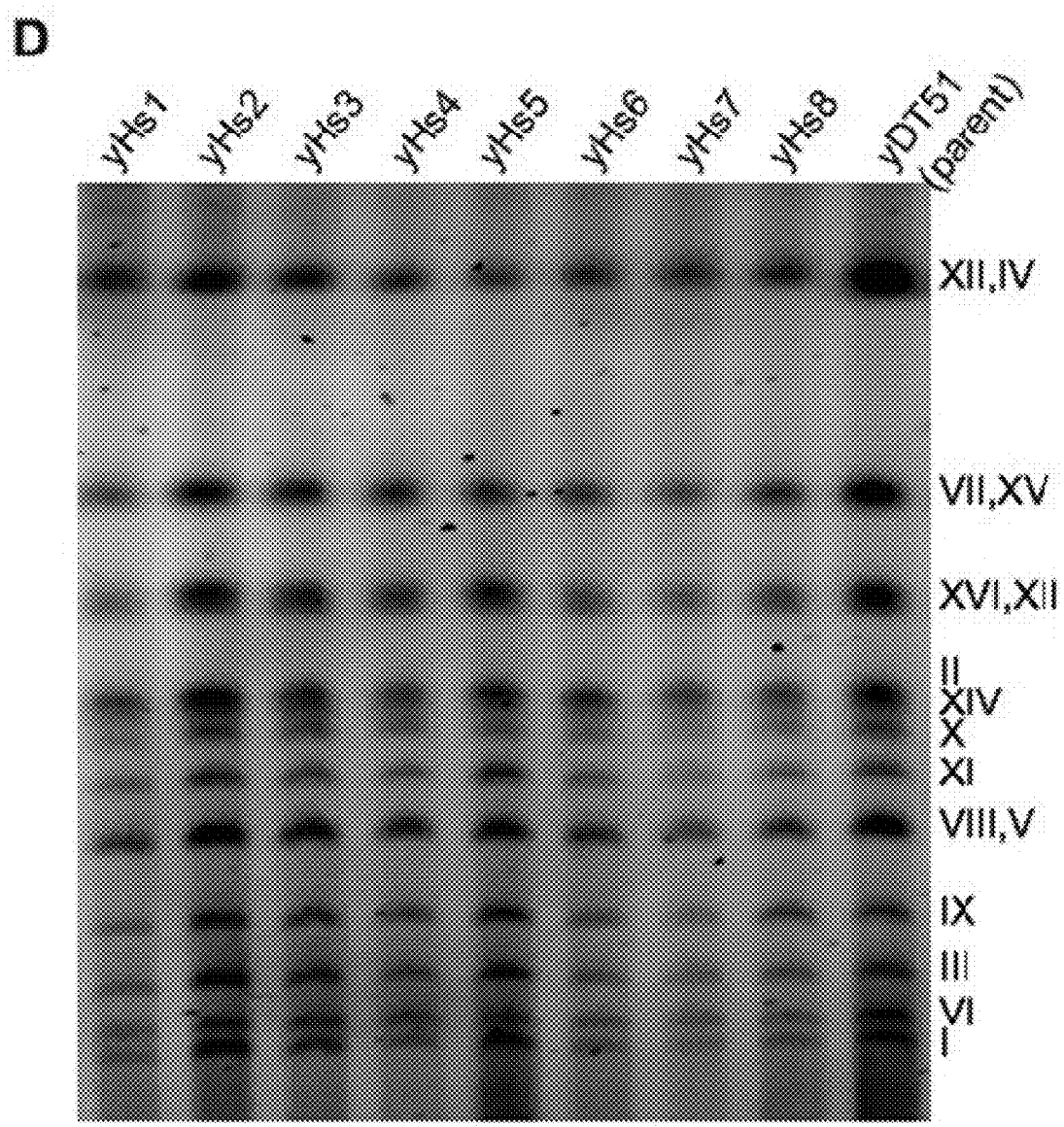
Figure 9:
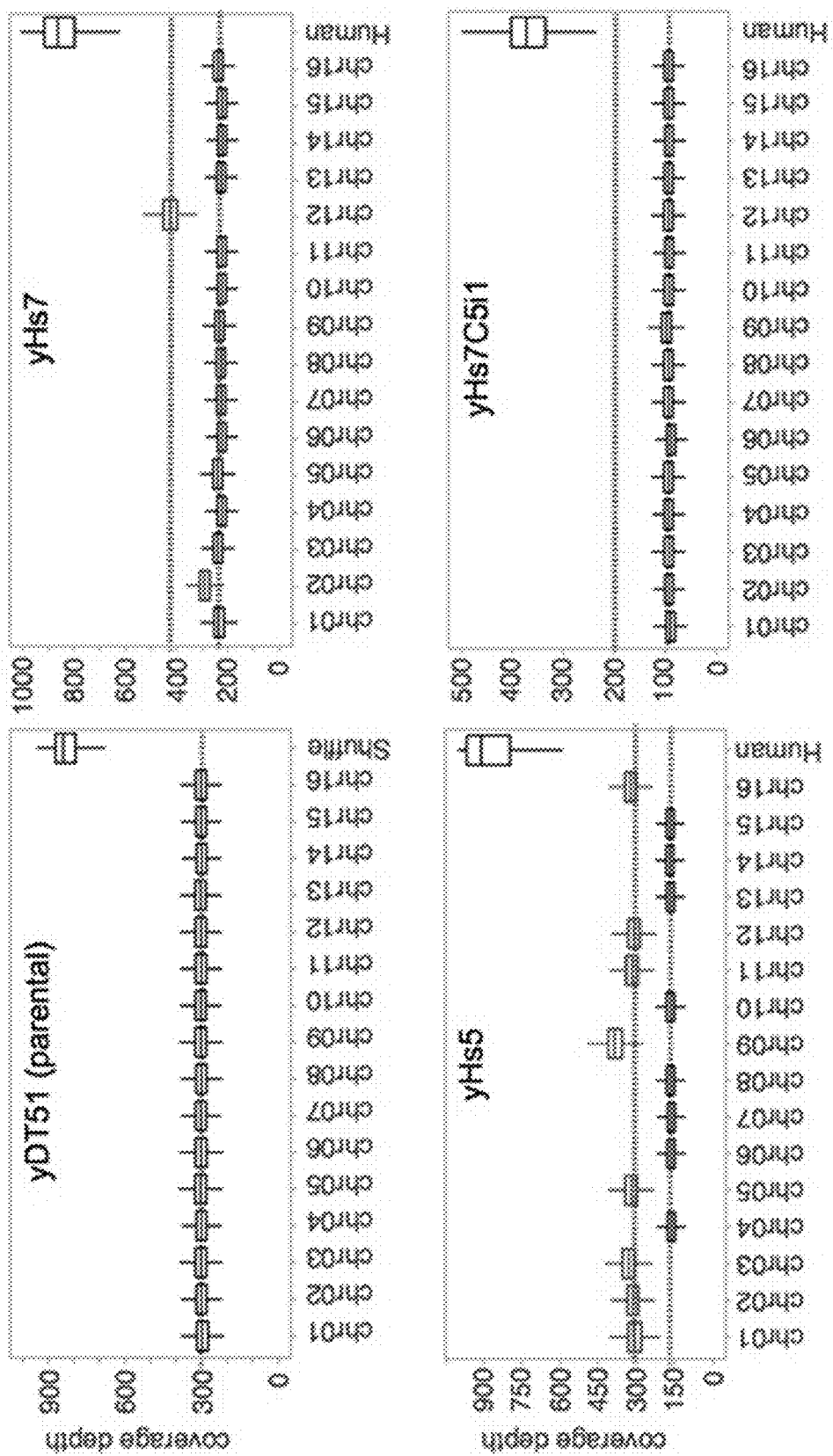

To date, we have only identified 8 such confirmed direct humanization events ("yHs"-series; FIG. 8F). Increased (high-copy plasmid) or decreased (genomic integration) human nucleosome gene copy number did not enhance humanization frequency (Table 3). The "yHs" cells grow on both synthetic complete (SC) and yeast complete (YPD) medium at 30° C. and 25° C., but not at higher temperatures (e.g., 37□C), can mate, and grow to various degrees on media that enhance defects in DNA replication, DNA repair, and vacuole formation (FIG. 9A, B). Finally, each of the humanized strains possessed differing rates of substantially slower than normal growth, and frequently produced larger and faster growing colonies over time (FIG. 1D and FIG. 8H). These observations are consistent with the accumulation of suppressors. A second factor reducing the humanization frequency is that a substantial proportion of the humanized cells in a population are unable to form a living colony.

Example 2

Bypass of Cell-Division Genes Promotes Growth With Human Nucleosomes

We performed evolution experiments on seven "yHs" lineages to determine how and to what extent yeast cells adapt to "live with" core human nucleosomes. The seven lineages were selected by serially diluting and sub-culturing liquid stationary phase cultures for 5 cycles (FIG. 2A). The evolved pools and isolates outperformed the pre-evolved strains on solid media, and doubled 33% more rapidly in liquid culture (FIGS. 2B and 9C). We then performed WGS on 32 of these humanized yeasts.

Pulsed-field gel electrophoresis of whole chromosomes from each yHs-lineage showed normal chromosome size (FIG. 9D). However, WGS revealed recurrent aneuploidy of specific chromosomes (FIGS. 2D, 9E, and Table 2). The human-histone plasmid copy number was no more than 2-fold higher than that in the parental strain yDT51. The majority of aneuploidies may be a detrimental consequence of human nucleosomes—as aneuploidies typically reduce fitness (Sheltzer et al., 2011)—but our frequently recurring aneuploidies (FIG. 2D) were consistent with other studies (Pavelka et al., 2010), which consider them possible reservoirs for positive selection. Chromosome number was often unstable during lineage evolution, as fractional differences (e.g., 1.5-fold chr1) were not due to insertions/deletions or diploidy, indicating potentially variable levels of aneuploidy at the population level. Only the evolved isolates yHs4C5i1 and the yHs7C5 lineage had a normal chromosomal sequence coverage, the latter perhaps due to a mutation in the gene DAD1, which controls microtubule force at the centromere (Sanchez-Perez et al., 2005). By contrast, yHs5 and its progeny had higher levels of aneuploidy, perhaps due to a subtle mutation in the gene SCC4, a cohesin loader (Lopez-Serra et al., 2014).

All humanized strains were either missing segments of mitochondrial DNA (mtDNA)(ρ−) or showed complete loss of mtDNA (ρ0), except for the lineages from yHs5 (ρ+). We investigated whether mtDNA loss alone might explain the slow growth rates (Veatch et al., 2009), but found that isogenic-WT ρ0 cells grow better than all humanized lines, and moreover the ρ+ yHs5C5i1 isolate was not the fastest growing isolate (Table 2).

We identified 36 mutations in or near genes among the 8 isolates and their derivatives (FIG. 1C, Tables 1 and 2), and 22 unique mutations appeared likely to affect gene function based on alterations to protein sequences. We constructed an interaction network from these 22 mutations using the String algorithm (Szklarczyk et al., 2015) (FIG. 2E). The enrichment of GO terms in this network was non-random, as the genes clustered in 4 processes: chromosome segregation, cytoskeleton, cell-cycle progression, and genes affecting RNA metabolism. These first 3 processes collectively affect mitotic cell-division (Janke et al., 2001; Lew and Reed, 1995). Therefore, mutations in genes that affect cell-division may suppress defects arising from human histones, possibly by circumventing cellular checkpoints triggered by aberrant chromatin properties. These results illustrate how much easier it is to evolve the surrounding the gene network to accommodate new functions rather than the gene itself.

Example 3

Specific Residues in Termini of Human Histones H3 and H2A Limit Yeast Growth

Figure 10:
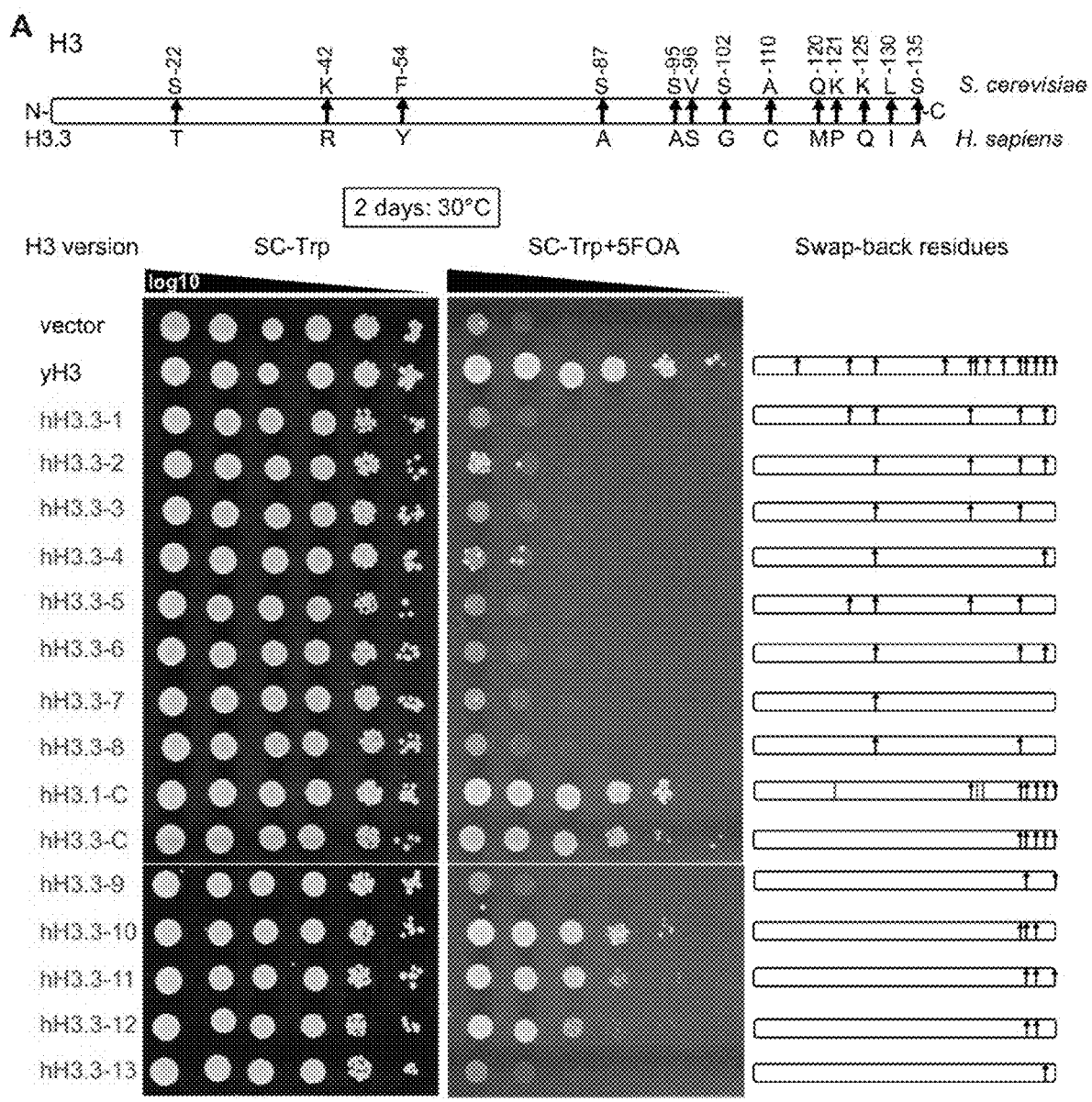
FIG. 10. Identification of residues in human 113 and 114, when swapped-back to yeast, improve humanization frequency, Related to FIG. 3. (A) Systematic mapping of human to yeast residues in human histone H3.3 using 5-FOA plasmid shuffling. The right-hand shows maps of the tested mutants, with black-arrows indicating positions swapped-back to yeast. Each plasmid was tested in strain yDT17, which contains deletions of both H3/H4 loci and is stabilized with a URA3-CEN plasmid containing the HHT1-HHF1 locus. Yeast are spotted in 10-fold serial dilutions. Versions labeled hH3.1-C and hH3.3-C were shown to complement well in yeast (McBurney et al., 2016). (B) Systematic mapping of human to yeast residues in histone H4. Swapped-back residues in hH4 were tested as described in (A) also in strain yDT17. (C) Combination of different hH3-swapback strains with completely human H4. When combined with human histone H4 (hH4), only two swap-back residues (P121K and Q125K) are required for hH3.1, whereas three are required for hH3.3.
Figure 10:
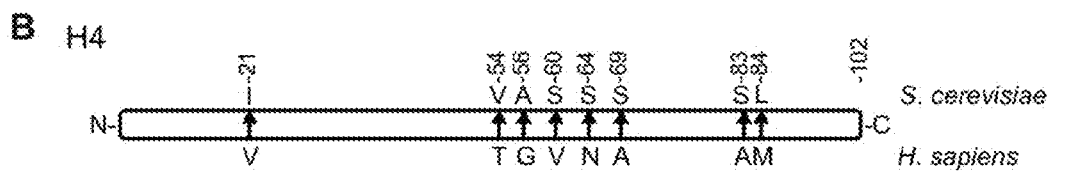
Figure 10:
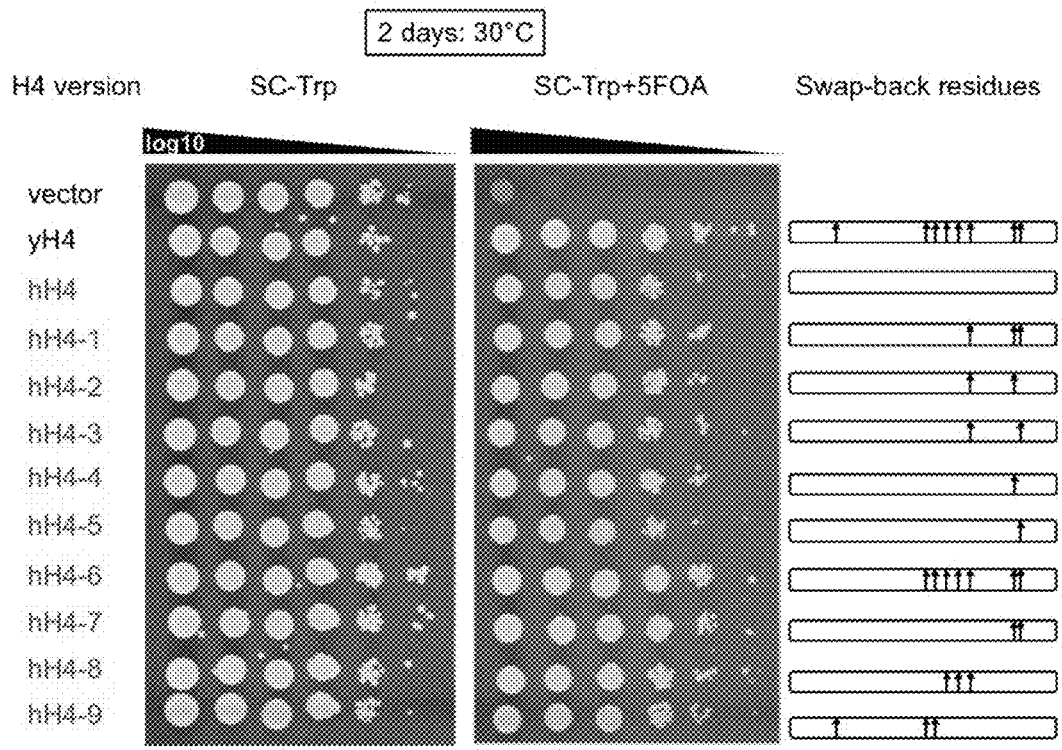
Figure 10:
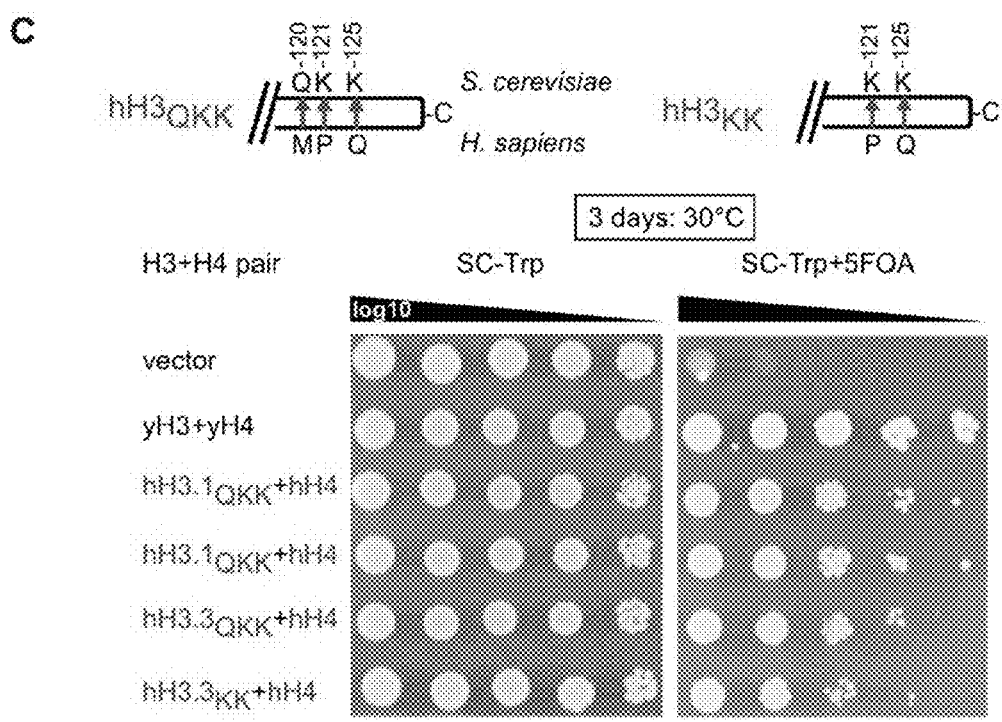

We were surprised to not identify any mutations within the human histone genes themselves. Converting the C-terminal residues of human histone H3 back to the yeast sequence enhances complementation (McBurney et al., 2016), and some species-specific residues cause lethality when mutated to alanine (Dai et al., 2008; Nakanishi et al., 2008). We systematically swapped residues from human to yeast across histones H3, H4, and H2A, in order to identify species-specific regions (FIGS. 10 and 11), but did not perform such studies on H2B as it complemented relatively well.

Swapping-back three residues in the C-terminus of hH3 enhances the humanization frequency (FIG. 10A), consistent with a recent study (McBurney et al., 2016), whereas swapping-back the lethal residues provided no benefit (Dai et al., 2008). Although hH4 already worked well, we identified two residues in its C-terminus that enhanced humanization (FIG. 10B). Only two swapped-back residues in hH3 (hH3KK; human→yeast P121K and Q125K) were required for complementation when combined with completely human H4 (FIG. 10C), although there appear to be differences between hH3.1 versus hH3.3 in this regard. A possible explanation for the two hH3 swap-back residues may be that in yeast H3, the two lysine swap-back residues are ubiquitylated by Rtt101Mms1, and mutations in H3 of K121R/K125R reduced H3/H4 dimer release from Asf1, restricting transfer to other histone chaperones (Han et al., 2013).

Figure 11:
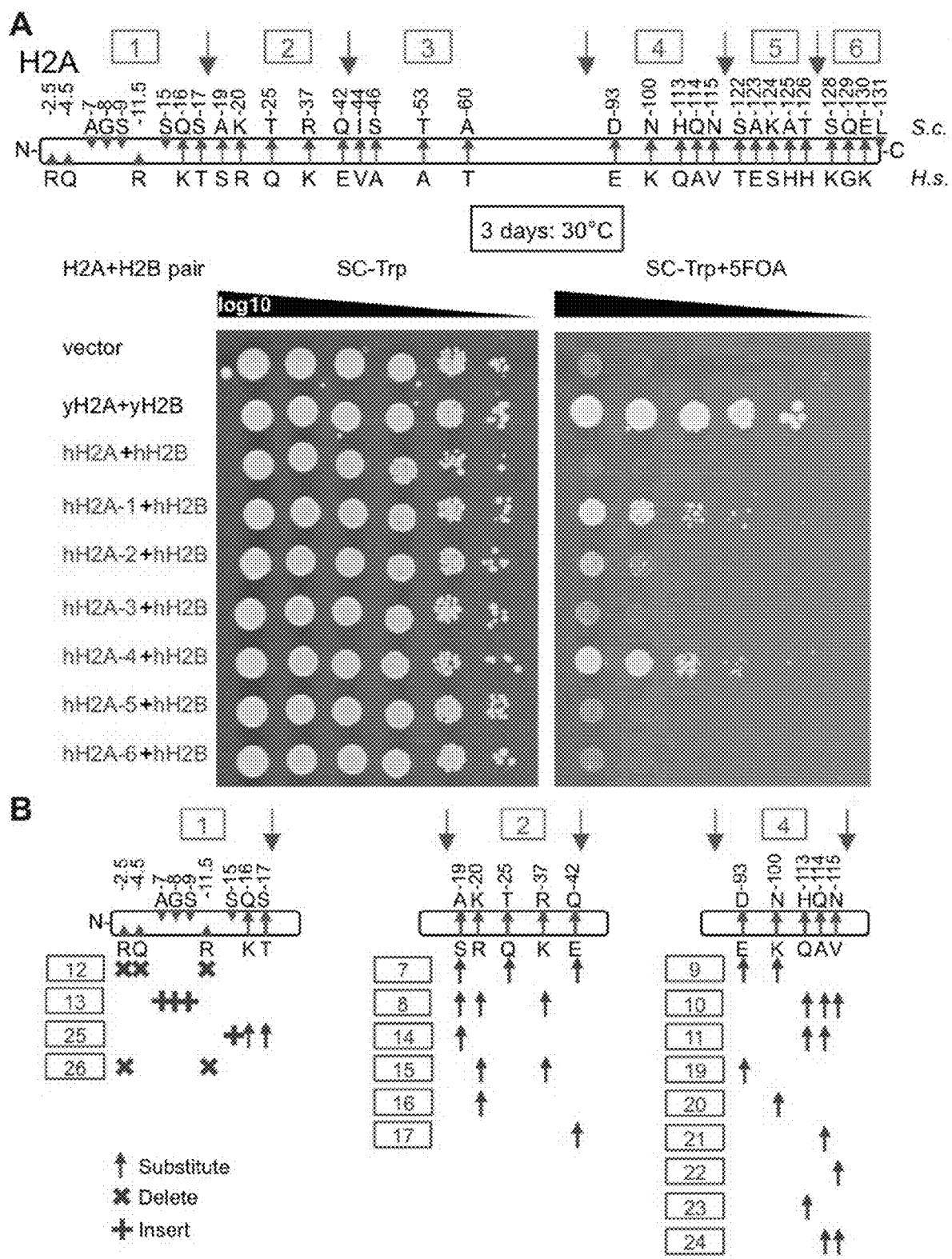
FIG. 11. Identification of swap-back residues in human H2A, that improve humanization frequency, Related to FIG. 3. (A) hH2A was partitioned into 6 regions, and each region was swapped-back to yeast to test complementation frequency using 5-FOA plasmid shuffling in strain yDT30.
Figure 11:
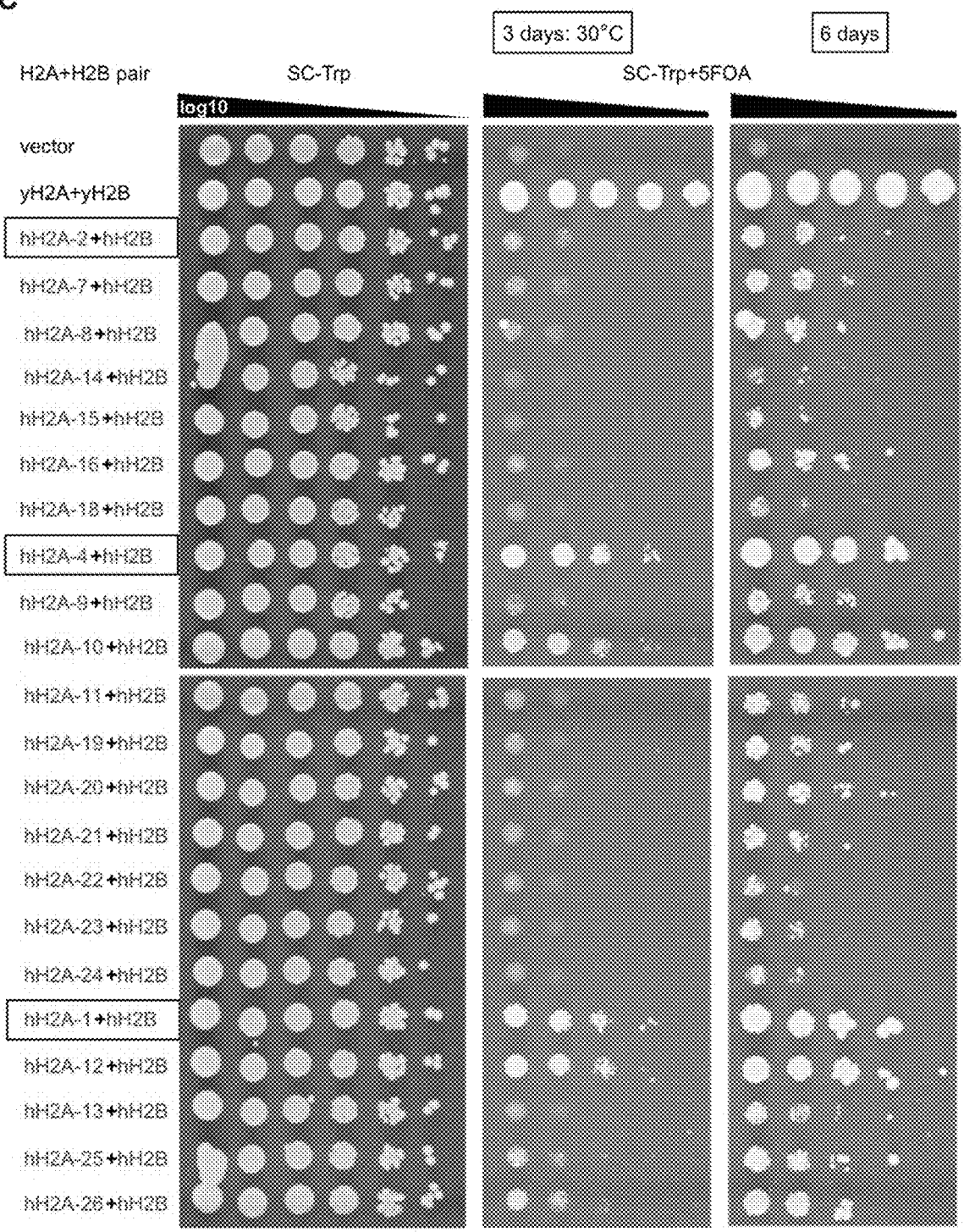
Figure 11:
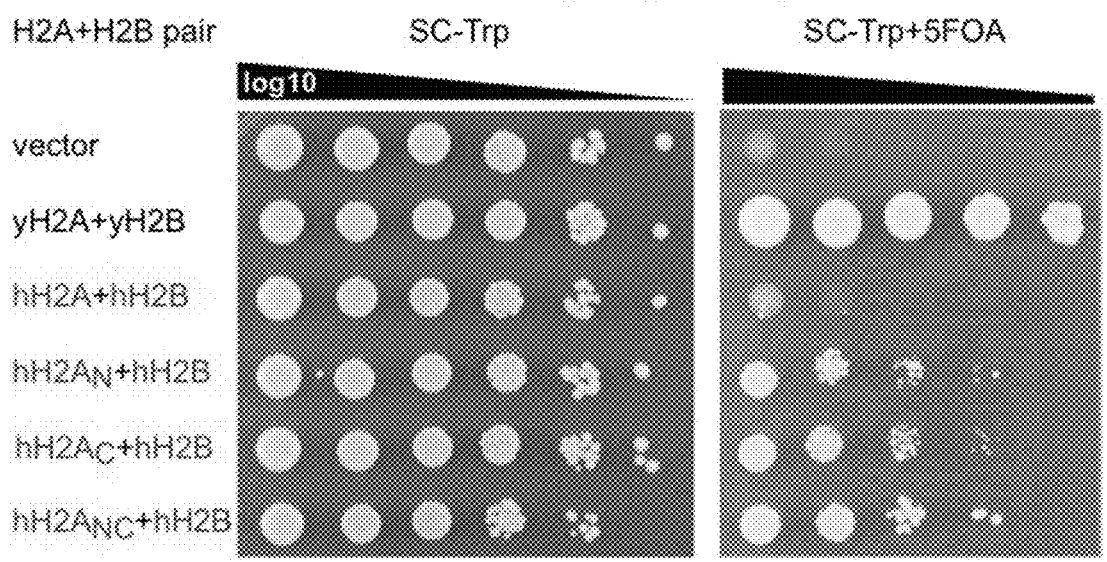
Figure 11:
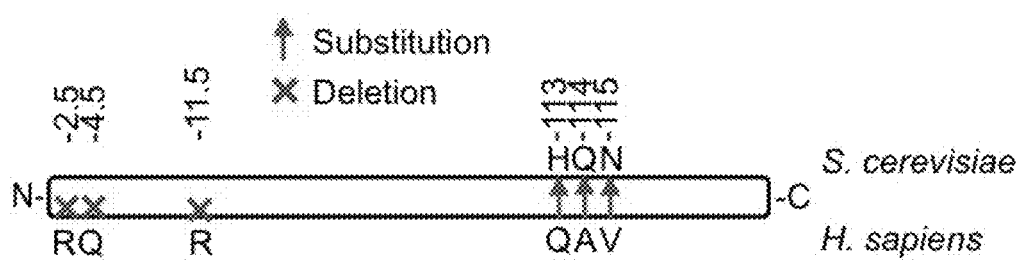

Swapping-back three broad regions in hH2A enhanced complementation in combination with fully human hH2B, the N-terminus, the C-terminus, and a region from residues 19 to 42 (FIG. 11). Further analyses narrowed the essential residues to three residues each in the N-terminus and C-terminus. Combining all six of these residues significantly enhanced the humanization frequency and growth rate of the yeast (FIG. 11D). Intriguingly, the mammalian lineage-specific N-terminal arginine residues, when inserted into yeast H2A, have been shown to increase chromosome compaction (Macadangdang et al., 2014). The C-terminal portion, which is exposed on the nucleosome face (White et al., 2001), may interact with histone chaperones (e.g., NAP1) analogous to the H3/H4 interaction with Asf1.

Figure 3:
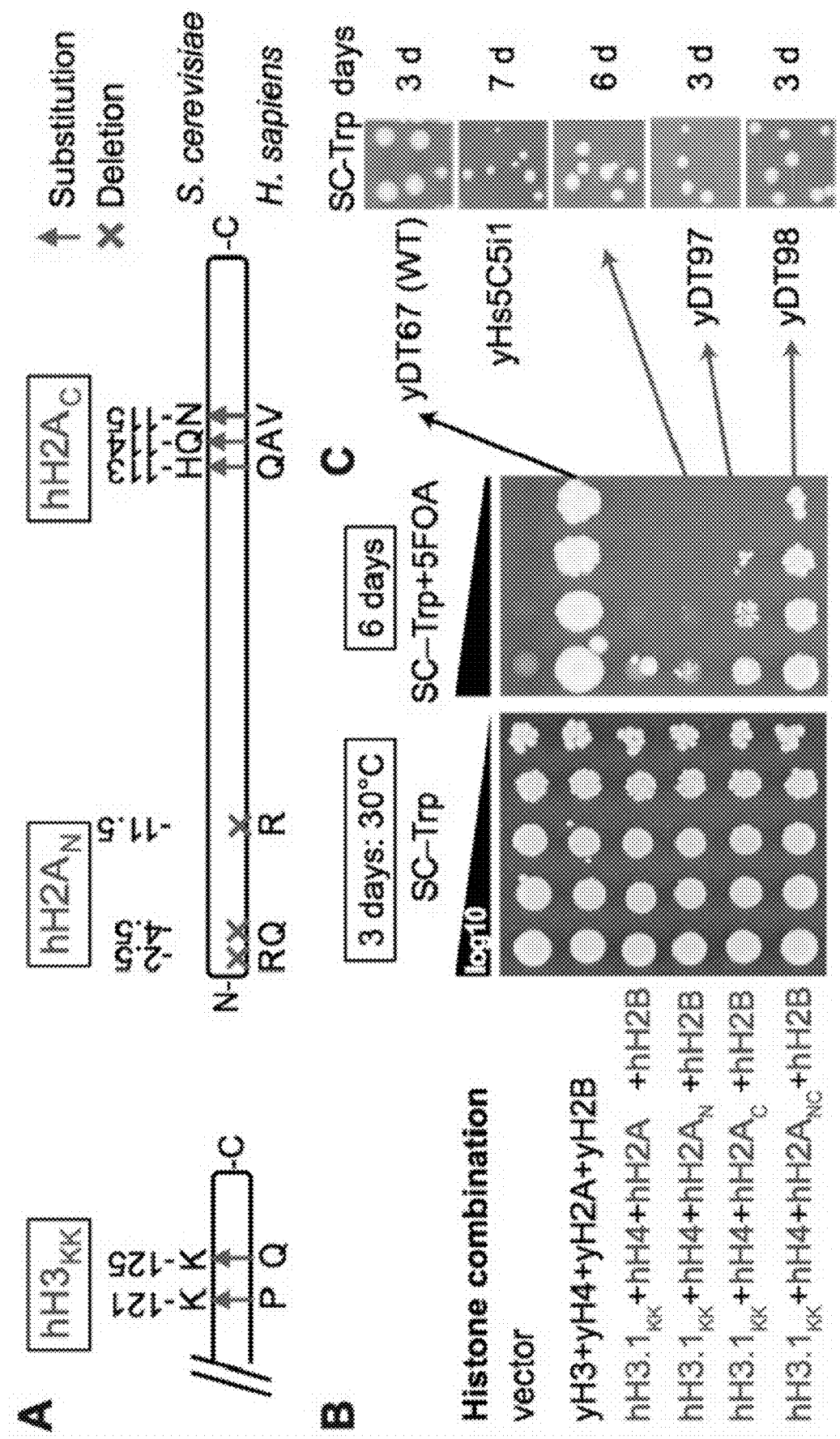
FIG. 3. Specific residues in the C-termini of histones 113 and H2A limit growth rates. (A) Maps of swapback residues that enhance human histone utilization identified in FIGS. 10 and 11. Two residues in the C-terminus of human histone H3 (hH3), and three swap-back residues each in the N-terminus or C-terminus of human histone H2A (hH2A) improved the complementation frequency and growth rate in conjunction with their respective human histone counterpart (i.e., hH4 and hH2B respectively). (B) Systematic combinations of swapback residues in hH3 and hH2A along with hH4 and hH2B show that eight swapback residues promote the highest rates of complementation. (C) Colony growth rate analyses shows that the five-residue swapback strain (yDT97) grows as well as the eight-residue swapback strain (yDT98). Both swapback strains grow at rates closer to isogenic-WT yeast (yDT67), and better than the fastest growing completely humanized isolate (yHs5C5i1).

We combined the 3 terminal-regions (hH3.1KK, hH2AN, and hH2AC) into human nucleosomes as various "Swap-back strains" (FIG. 3). As expected, combining all 3 swapped-back regions enhanced humanization (8-residue swayback strain yDT98) to 10-2 in only 3 days (FIG. 3B). However, the swapback strain with only the two C-terminal regions (hH3.1KK and hH2AC; 5-residue swap strain yDT97) grew as fast as the 8-residue swapback version (yDT98), and both of these strains grew nearly as fast as our isogenic-WT strain (yDT67) in 3 days. The 5-residue swapback strain (yDT97) was used for further studies.

Example 4

Human Nucleosomes Delay Adaptation to New Transcriptional Programs in Yeast

Figure 4:
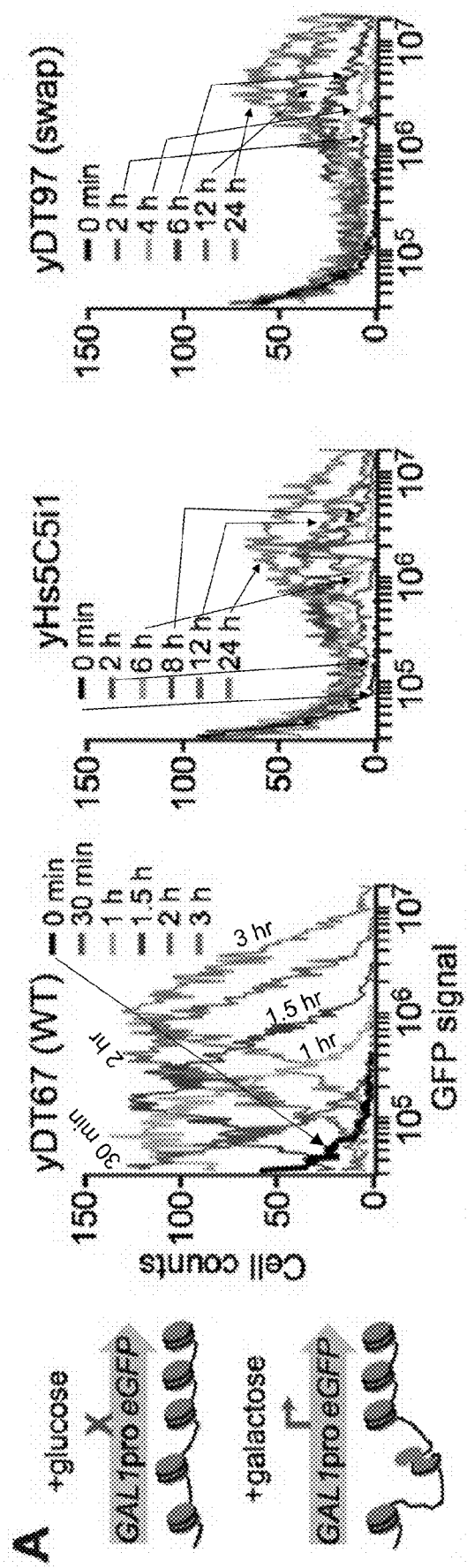
FIG. 4. Humanized yeast have trouble adapting to new conditions. (A) Humanized yeast have delayed chromatin remodeling. Chromatin remodeling time-course was analyzed by galactose induction of eGFP using flow cytometry. (B) Humanized yeast have a prolonged S-phase and/or arrest in G1. Cell-cycle analysis based on DNA content. Cells were stained with sytox green, and DNA content was measured by flow cytometry. Each plot shows 10,000 cells in log-phase growth, except where indicated. (C) Violin plots showing that humanized yeast cells are larger and have dysregulated cell size based on phase-contrast microscopy measurements.
Figure 4:
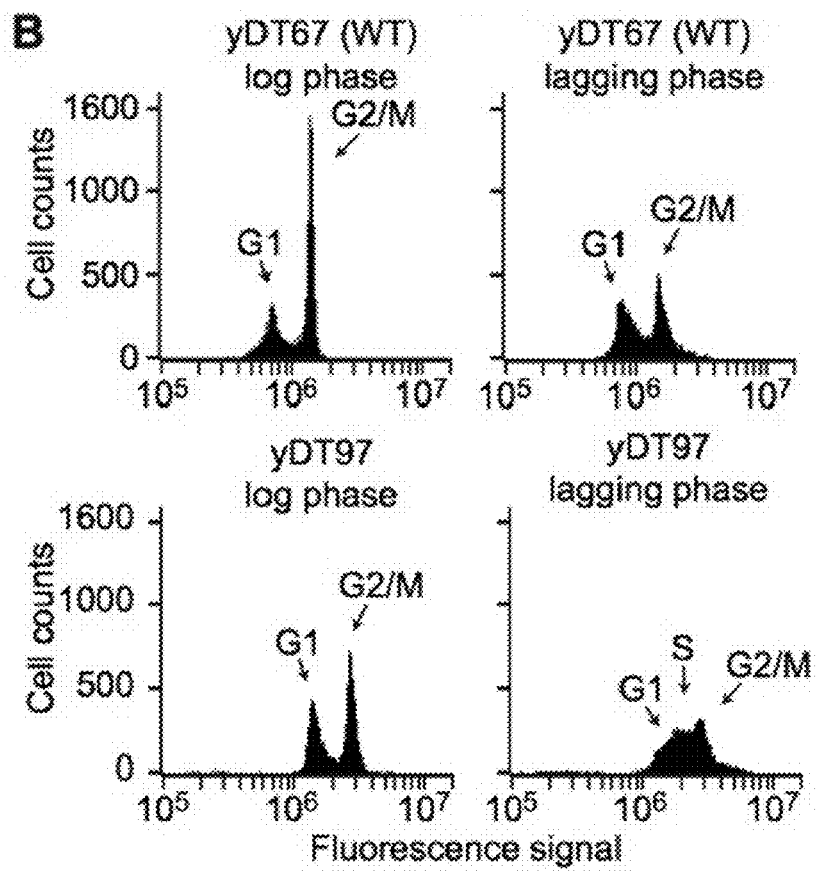
Figure 4:
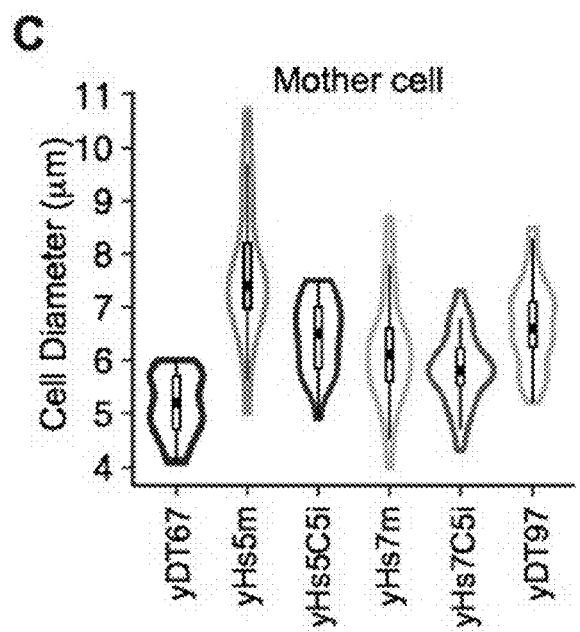

Intriguingly, we often observed that the humanized cells had difficulty adapting to new environments (e.g., colony to liquid culture), which suggested slowed chromatin remodeling to new transcriptional programs. Consistent with this hypothesis, using a GAL1-promoter driven eGFP as a proxy for switching to the galactose utilization transcriptome using the RSC complex (Floer et al., 2010) we showed that cells with human nucleosomes had a pronounced delay in transcriptional response to galactose as the sole carbon source, as well as decreased maximal expression on induction (FIG. 4A).

We then assessed how readily the cells adjust to new phases of the cell-cycle, a process that also requires extensive chromatin remodeling. Using both bud-counting and flow cytometry of log-phase cells, we observed reduced cell-division, as only 40-60% of humanized cells reach the G2/M phase compared to ~90% in isogenic-WT (FIG. 12B). More importantly, the lag-phase cultures of the yDT97 "swap" strain display a prolonged S phase, indicative of a delay in adjusting to log-phase growth (FIGS. 4B and 12D). This could result from an inability to accumulate new histones onto nascent DNA or an inability to remodel and remove chromatin-bound factors (Ma et al., 2015).

Figure 12:
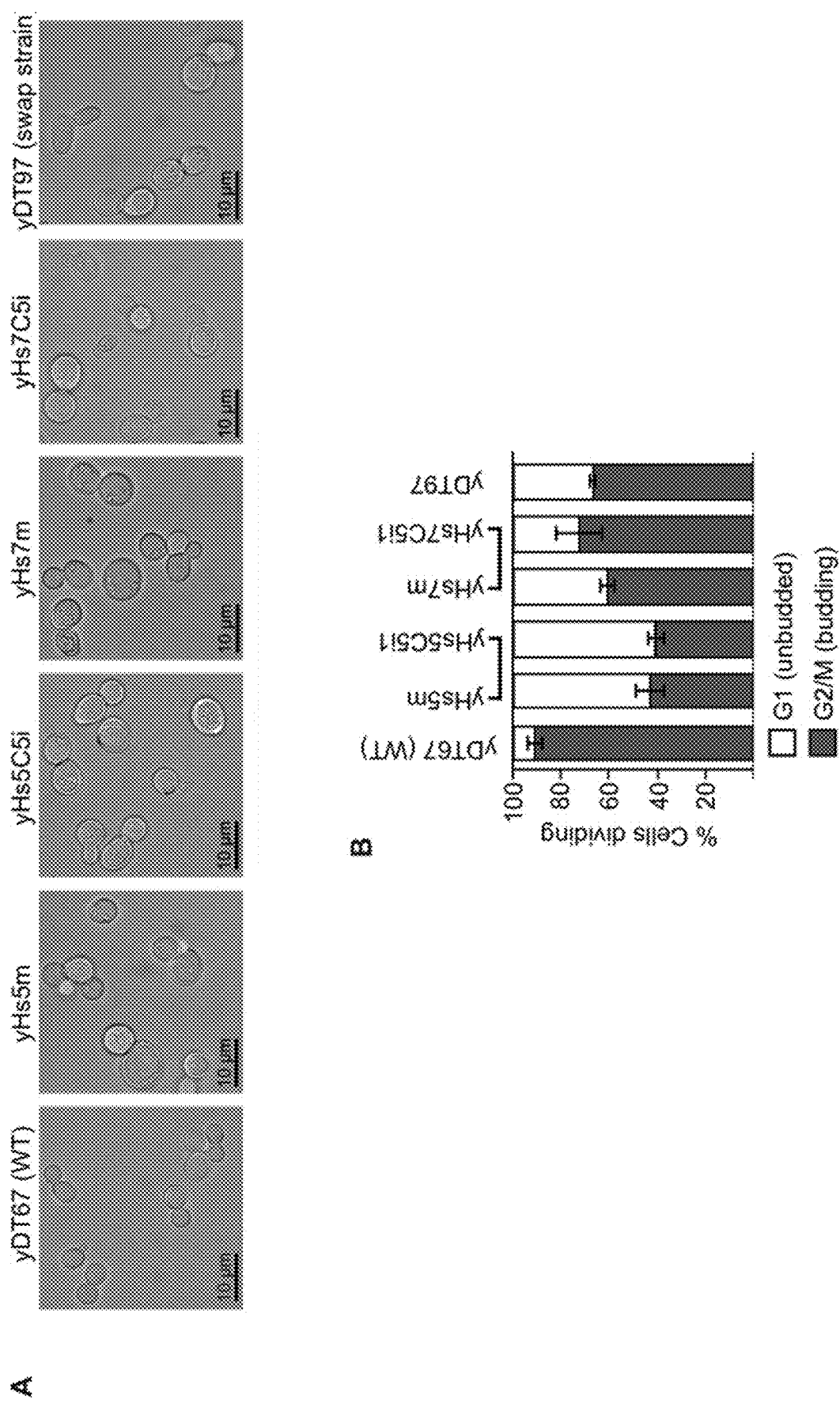
FIG. 12. Yeast with human nucleosomes have larger and less regulated cell sizes, and arrest in G1, Related to FIG. 4. (A) Image stills of yDT67 (WT) yeast compared to humanized strains. (B) Percent of cells in either the unbudded or budded state from phase-contrast microscopy images. Bars are standard error of the mean from 4 separate images. (C) Violin plots with boxplots inside showing size distributions of the indicated strains for various states of budding. Plots are based on ~50 cells measured from four separate microscopy images. F-tests measure significance of whether two populations have different size distributions. Two-tailed T-tests measure significance of difference in average cell size. (D) Cell-cycle analysis based on DNA content. Cells were stained with sytox green, and DNA content was measured by flow cytometry. Each plot shows 10,000 cells in log-phase growth, except where indicated. (E) Micromanipulation of single-cells for growth. Most cells remained intact (black underline). Cells with white circles grew for a few cell-divisions and then arrested.
Figure 12:
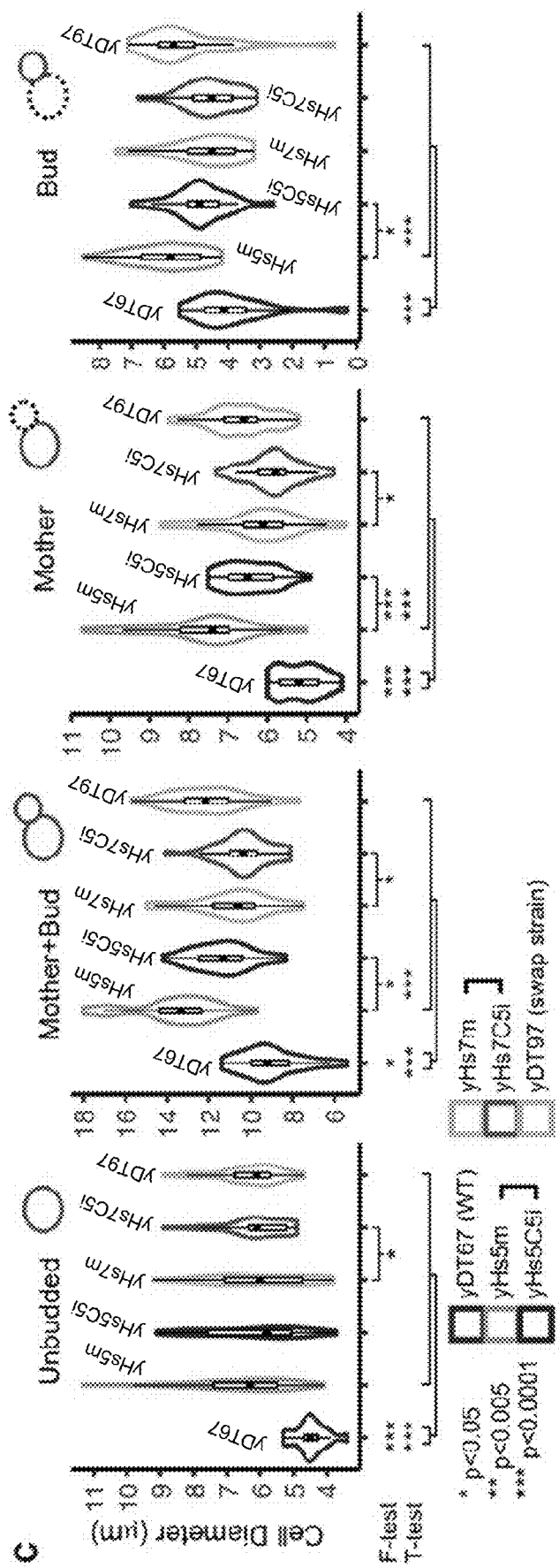
Figure 12:
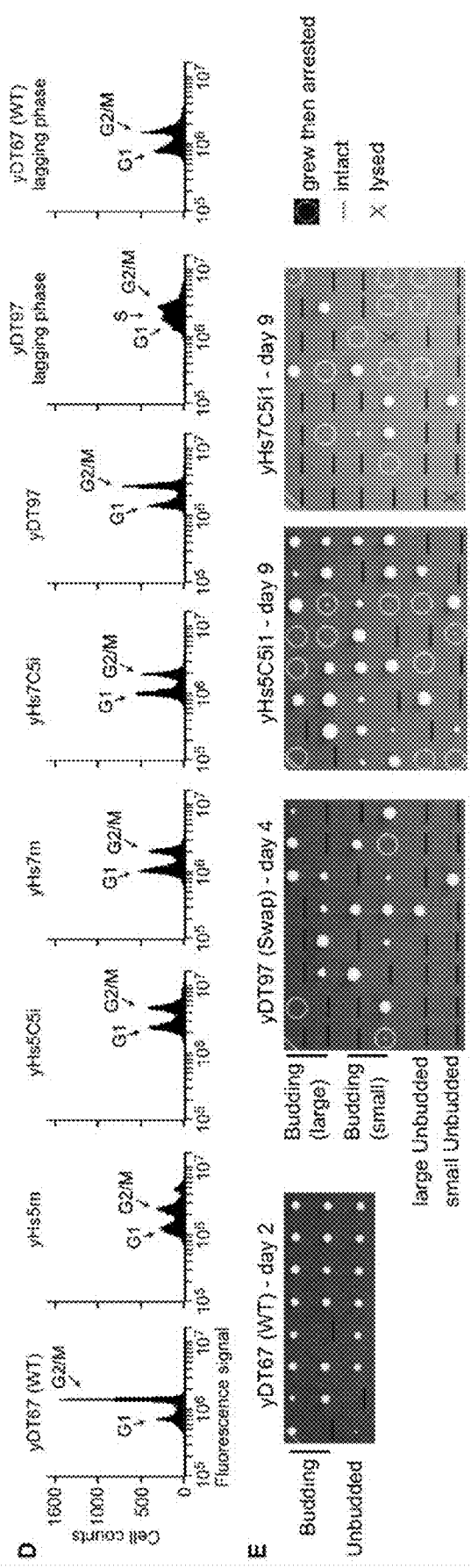

The humanized cells were also larger in size on average and produced a greater range in cell sizes (FIGS. 4C and 12), which could indicate an inability to regulate cell-size control due to less permissive chromatin. By micro-manipulating single cells onto YPD plates, we found no growth difference between large and small cells (FIG. 12E). However, unbudded cells (G1) were less likely to continue to grow than budding cells, although they all mostly remained intact after several days of monitoring. Surprisingly, a high fraction of single cells grew for a number of cell-divisions before arresting as a population (i.e., arrested before reaching the size of a visible colony). Together, these results are consistent with the hypothesis that human nucleosomes delay adaptation to other phases of the cell-cycle.

Nucleosome Organization is Specified by the Chromatin Remodeling Network

Figure 5:
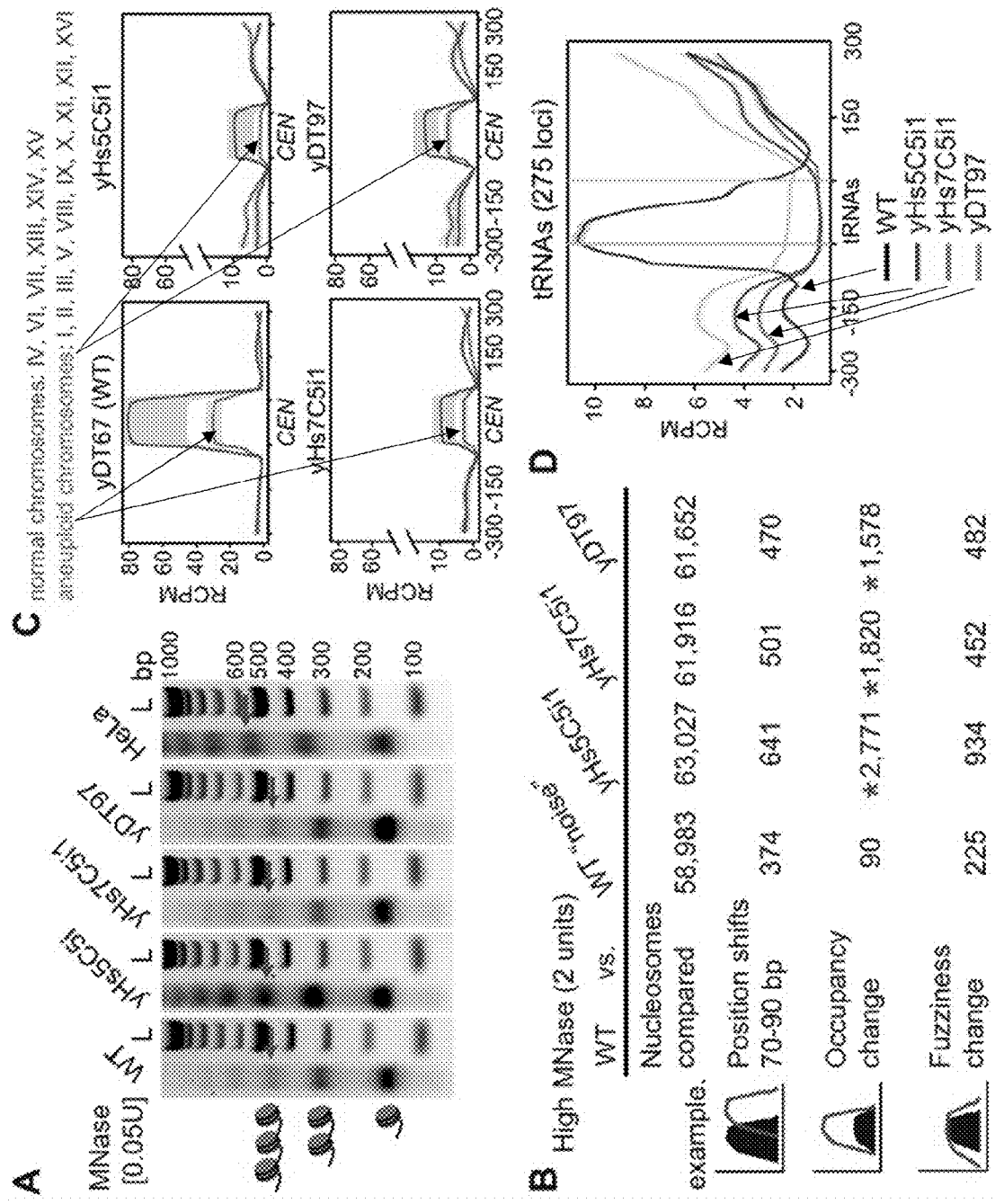
FIG. 5. Human nucleosome organization in yeast. (A) MNase digestions reveal that human nucleosomes produce the same nucleosome repeat length as yeast nucleosomes, compared to the longer length of human nucleosomes in HeLa cells. Red arrows indicate position of the tri-nucleosome. The "bp" indicates base-pair size of the DNA ladder ("L"). (B) Table of high (2 units/ml) MNase-seq nucleosome dynamics between humanized to WT yeast, and WT experiment 1 to WT experiment 2 ("noise"). Occupancy and fuzziness changes use a strict False Discovery Rate cut-off of 0.05 ($p<10^{-85}$) and additional parameters in Methods. (C) High MNase-seq read counts at centromeric regions, plotted for chromosomes that were normal or aneuploid in FIG. 2D. RCPM refers to read counts per million mapped reads. (D) High MNase-seq read counts for all 275 tRNA genes comparing humanized vs. WT strains showing depletion of either RNAP3 or nucleosomes.
Figure 13:
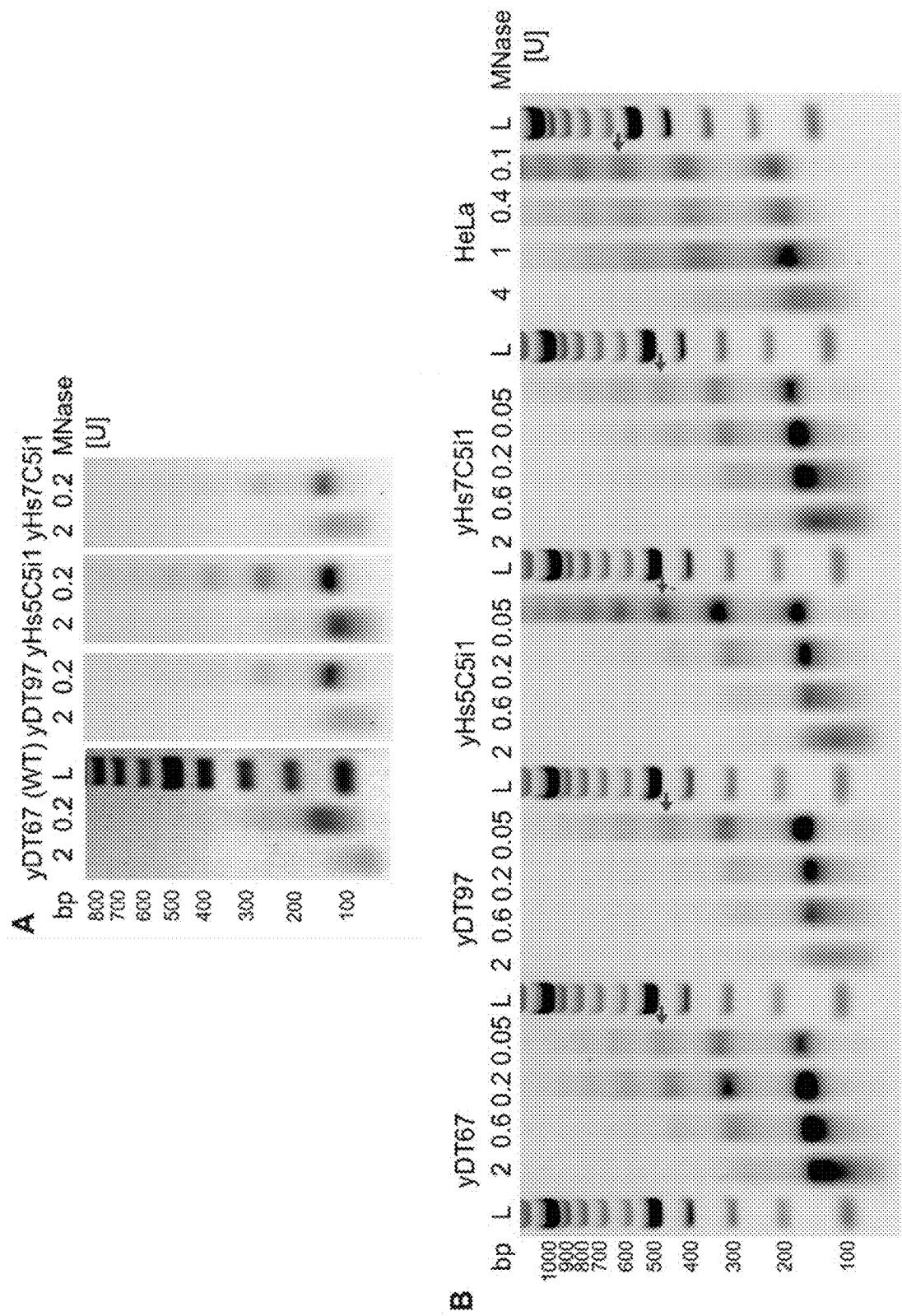
FIG. 13. MNase digestions and MNase-seq of humanized yeast, Related to FIG. 5. (A) Representative DNA fragments of high (2 units) and low (0.2 units) chromatin MNase digestions used for MNase-sequencing run on a 1% agarose gel. Experiment 1 was performed in biological triplicate and experiment 2 was performed once. All samples from same strain had similar profiles. WT high MNase digests consistently produced a lower DNA yield (3-4 fold), suggesting more accessible DNA, but we chose not to normalize to this because we did not use spike-in controls. "M" refers the DNA marker. (B) Full MNase-titration digestion agarose gel shown in FIG. 5A. As WT digests produced less yield, these gels show normalized DNA loading. Red arrows indicate position of the tri-nucleosome, which differs only in the human cell line nucleosome digest. HeLa cells were digested at higher concentrations for a shorter duration and with sonication. "L" refers the DNA marker and "bp" indicates base-pair size. (C) Fragment length histogram from the low and high MNase-seq reads. (D) Low MNase-seq read counts at centromeric regions, plotted for chromosomes that were normal or aneuploid in FIG. 2D. RCPM refers to read counts per million mapped reads. (E) Table of Low (0.2 units/ml) MNase-seq nucleosome dynamics between humanized to WT yeast, and WT experiment 1 to WT experiment 2 ("noise"). Occupancy and fuzziness changes use a strict False Discovery Rate cut-off of 0.05 ($p<10^{-85}$) and additional parameters in Methods.
Figure 13:
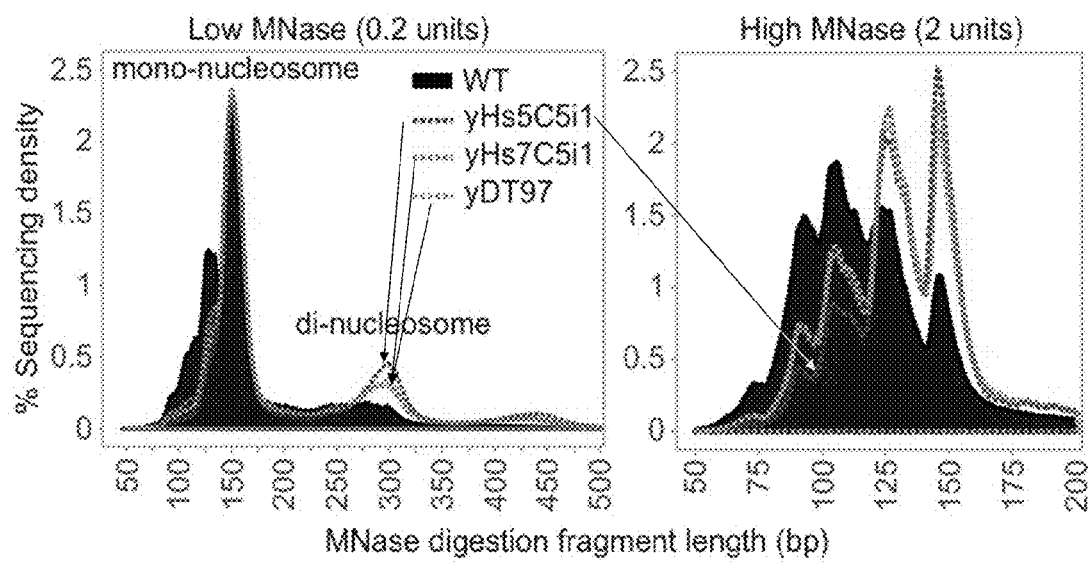
Figure 13:
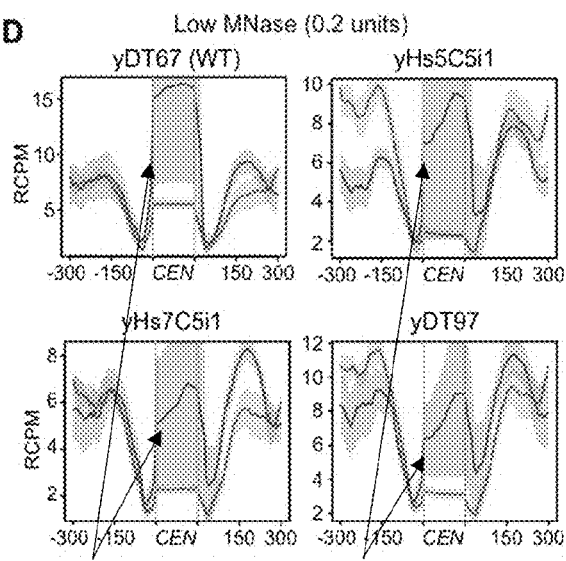
Figure 13:
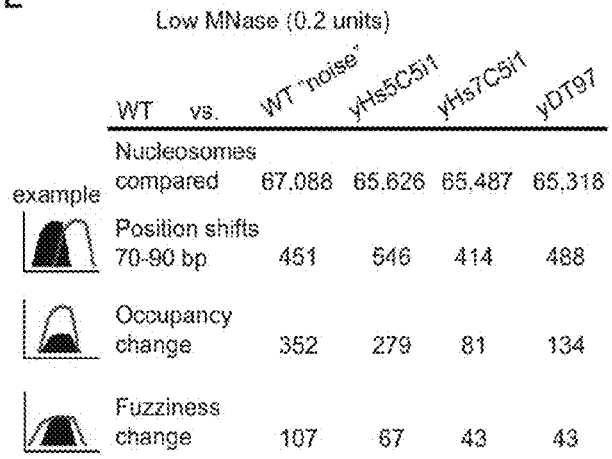

To evaluate the organization of human nucleosomes on the yeast genome we performed MNase digestion titrations and MNase-seq on evolved and swapback strains using 'high' and 'low' enzyme concentrations (FIGS. 5 and 13), to reveal possible differences in nucleosome accessibility (Kubik et al., 2015).

Unexpectedly, the nucleosome repeat length (NRL) of yeast chromatin built using human nucleosomes was identical to the NRL in isogenic-WT yeast, and is substantially shorter than that for human HeLa cells (FIG. 5A). The di-nucleosome length (~300 bp) from low concentration MNase-seq confirms a short mean nucleosome repeat length (FIG. 13C). These data indicate that the NRL in humans is not an intrinsic property of human core nucleosomes, but is likely specified by nucleosome remodelers, by the genomic sequence itself (Segal and Widom, 2009) or by some combination of these factors.

To our surprise, the numbers of nucleosomes with altered positioning or fuzziness (movement) was no different than that of isogenic-WT "noise" (Chen et al., 2013). However, there are substantial occupancy differences, which are distinct even amongst the humanized lines (FIG. 5B). Nevertheless, this suggests that nucleosome positioning is determined less so by the type of nucleosome, and much more so by the underlying DNA sequences and the network of chromatin-remodelers for a given species.

As suggested by the chromosome segregation suppressor mutations identified earlier (FIG. 2E), we find that human nucleosomes lead to depletion of centromeric nucleosomes as well as relative to the surrounding nucleosomes, perhaps due to conflict with the yeast centromeric H3 variant CSE4 (FIGS. 5C and 13D). Relative to the neighboring nucleosomes, depletion was greatest for centromeres on aneuploid chromosomes observed earlier by WGS (FIGS. 2D and 5C). Strain yHs5C5i1, which had the highest levels of aneuploidy, had greater depletion at these nucleosomes, whereas strain yHs7C5i1, which has normal chromosome numbers and carries a relatively subtle missense mutation (E50D) in the essential gene DAD1, has slightly better positioning at these nucleosomes (FIG. 5C).

Finally, all 275 tRNA genes had depleted sequence coverage in their gene-bodies compared to WT (FIG. 5D). Unlike RNAP2 genes, tRNAs possess an 'internal control region', thus, the depleted regions could represent a loss of RNAP3 and accessory factors (Acker et al., 2013), or nucleosome depletion coupled to RNAP3 transcription elongation. In fact, substantially elevated tRNA levels were observed in RNA from yHs cells (FIG. 14A), perhaps suggesting human nucleosomes are less stably bound to tRNA sequences. However, as yeast tRNAs are already highly expressed and mostly devoid of nucleosomes, this could instead indicate that tRNA levels are normal, and that it is mRNAs that are highly repressed by human nucleosomes, thus altering the tRNA/mRNA ratio.

Example 5

Human Nucleosomes Produce Chromatin More Generally Repressive for RNAP2

Figure 6:
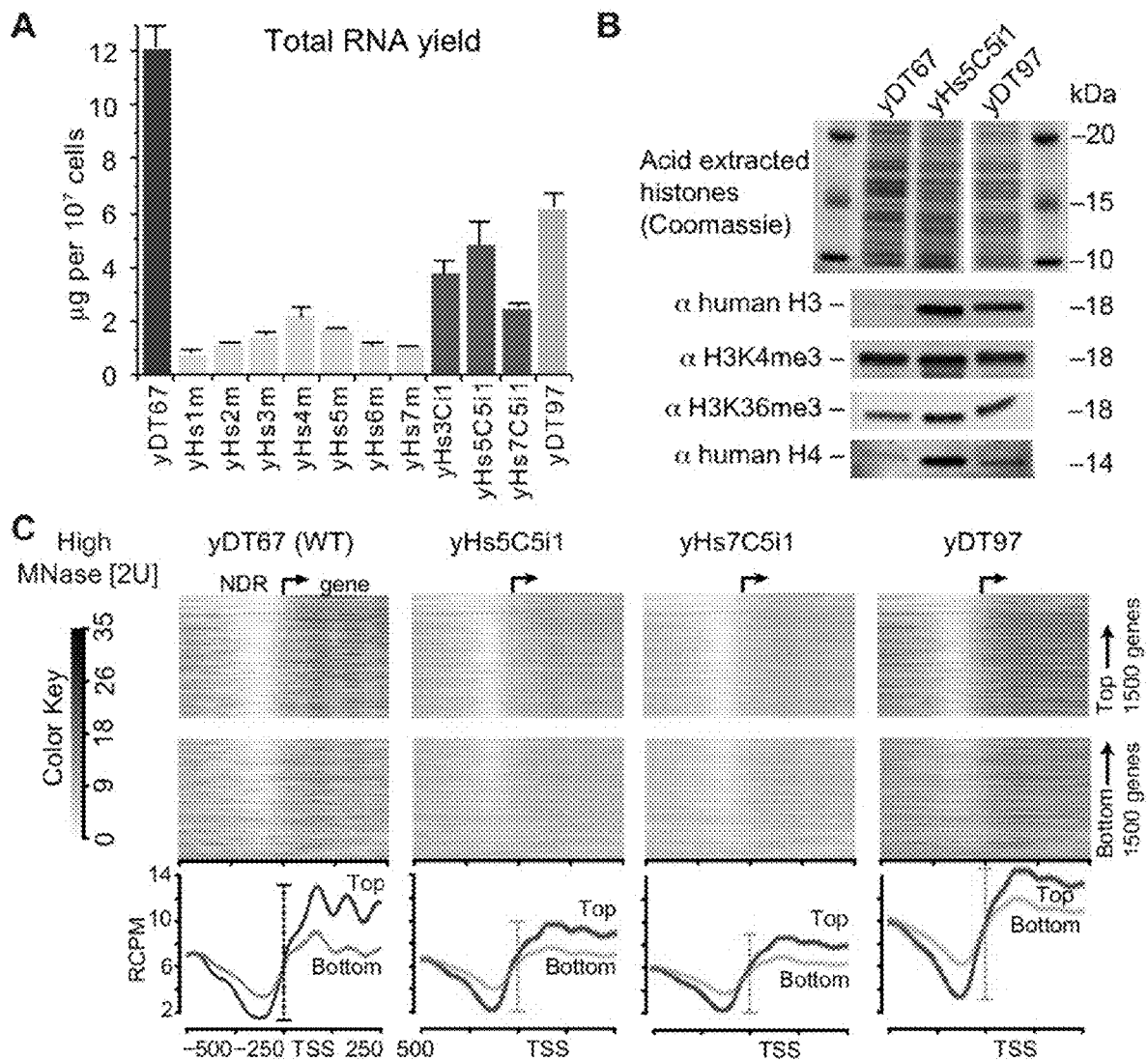
FIG. 6. Human nucleosomes are more repressive. (A) Pre-evolved yHs strains (yHs-m) have reduced levels of bulk total RNA (6-8 fold), whereas the evolved and swap strains slightly increase RNA content. Bars show standard error of the mean of 3 biological replicates. (B) Acid-extracted histones from strains analyzed for equal loading by Coomassie staining, and then immunoblotted using different H3 and H4 antibodies. (C) Heatmaps and average profiles of high concentration MNase-seq reads aligned around the transcription start sites (TSS)±500 bp of the top and bottom 1500 genes by expression. RCPM and color key refers to read counts per million mapped reads.
Figure 14:
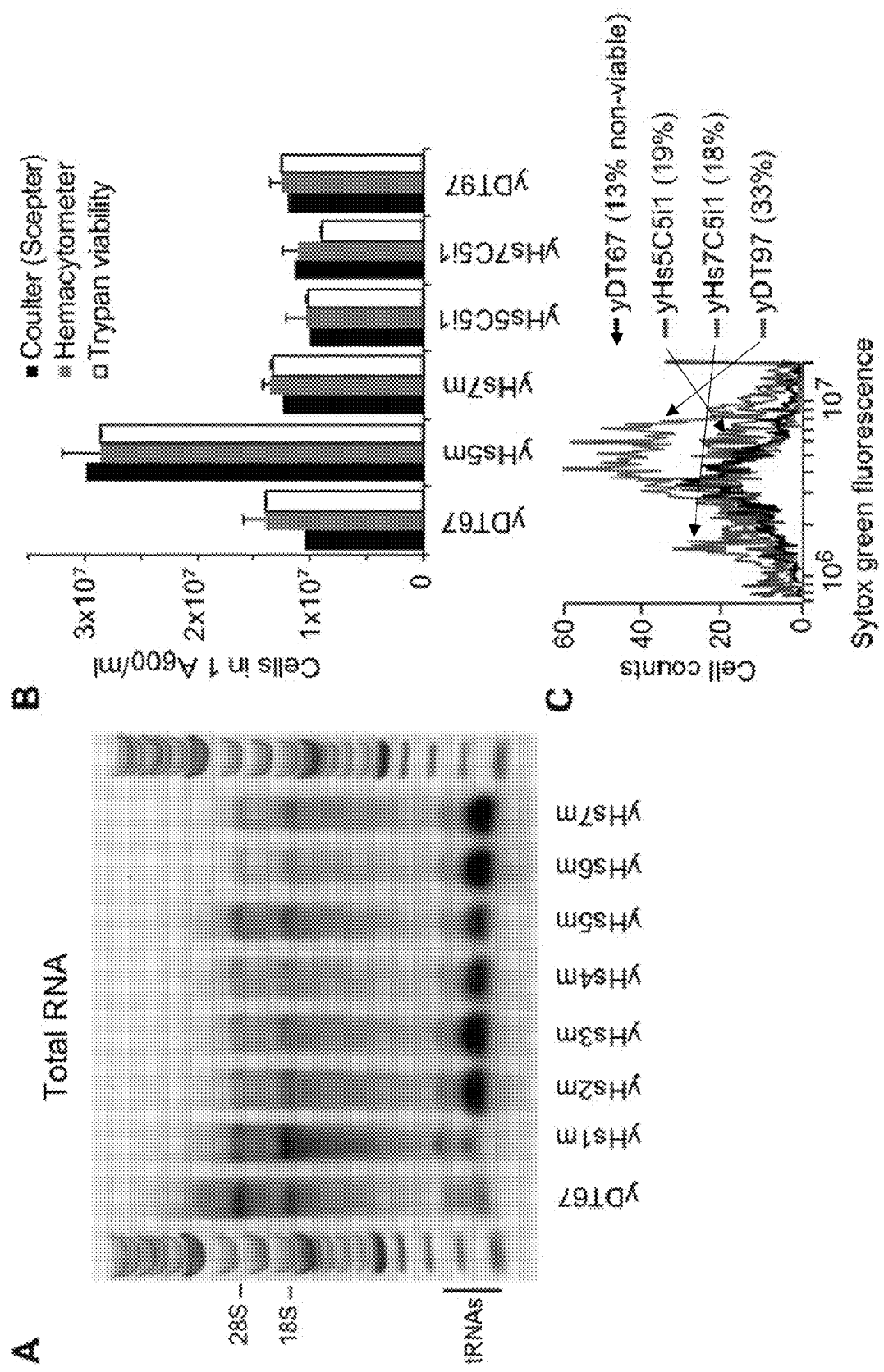
FIG. 14. Humanized yeast RNA and protein levels, Related to FIG. 6. (A) Total RNA from humanized cells have a similar rRNA to mRNA pattern and ratios as WT cells, although most have elevated tRNA expression. Because tRNA levels are so elevated, mRNA levels are likely lower than indicated in FIG. 6A. (B) Reduced RNA content is not due to reduced cell numbers per $A_{600}$, as yHs cells possess identical or even higher numbers of viable cells ($\geq 10^7$ cells or $A_{600}$). Cells were measured using both coulter counting (Millipore Scepter) and hemocytometer microscopic counting. Viability was determined by counting number of cells that exclude Trypan blue staining. Bars show standard deviation of 2 replicates. (C) Percentage of non-viable cells (cell viability) determined by Sytox green uptake into dead cells and measured by flow cytometry. (D) Whole-protein extracts of indicated strains run on 12% SDS-bis-Tris acrylamide gel and stained with Coomassie blue. Protein yields were similar on a per cell basis, and each lane has 50 µg total protein loaded. Proteins <25 kDa (e.g., histones) appear reduced in abundance. (E) Heatmaps and average profiles of low concentration MNase-seq reads aligned around the transcription start sites (TSS)±500 bp of the top and bottom 1500 genes. RCPM refers to read counts per million mapped reads.
Figure 14:
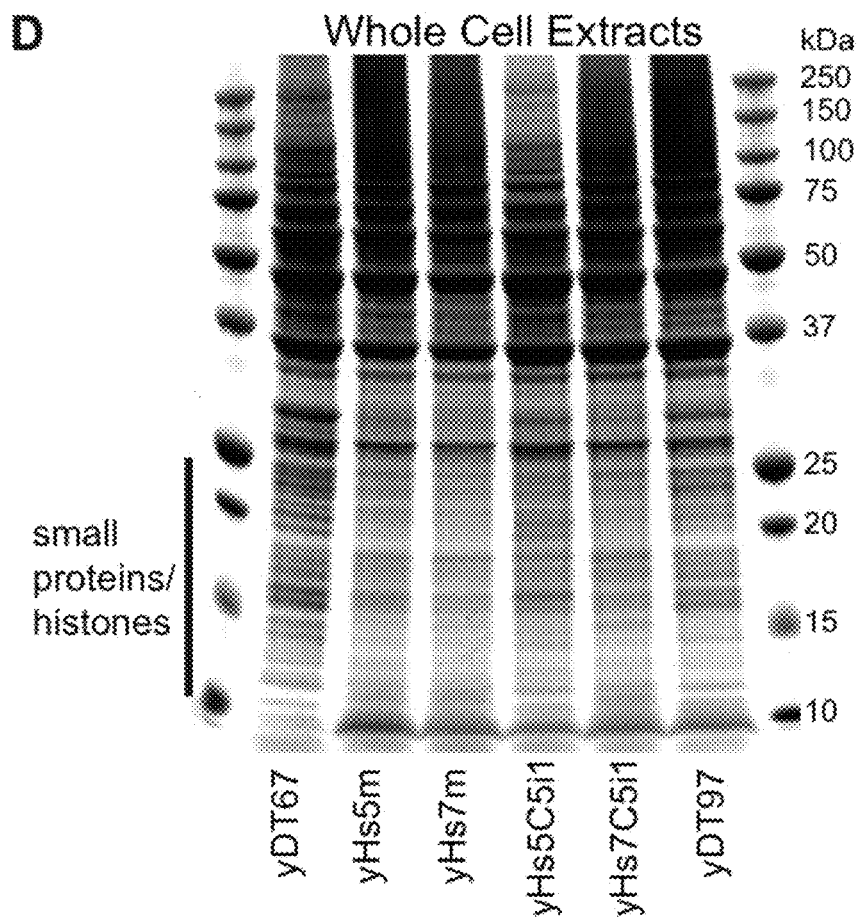
Figure 14:
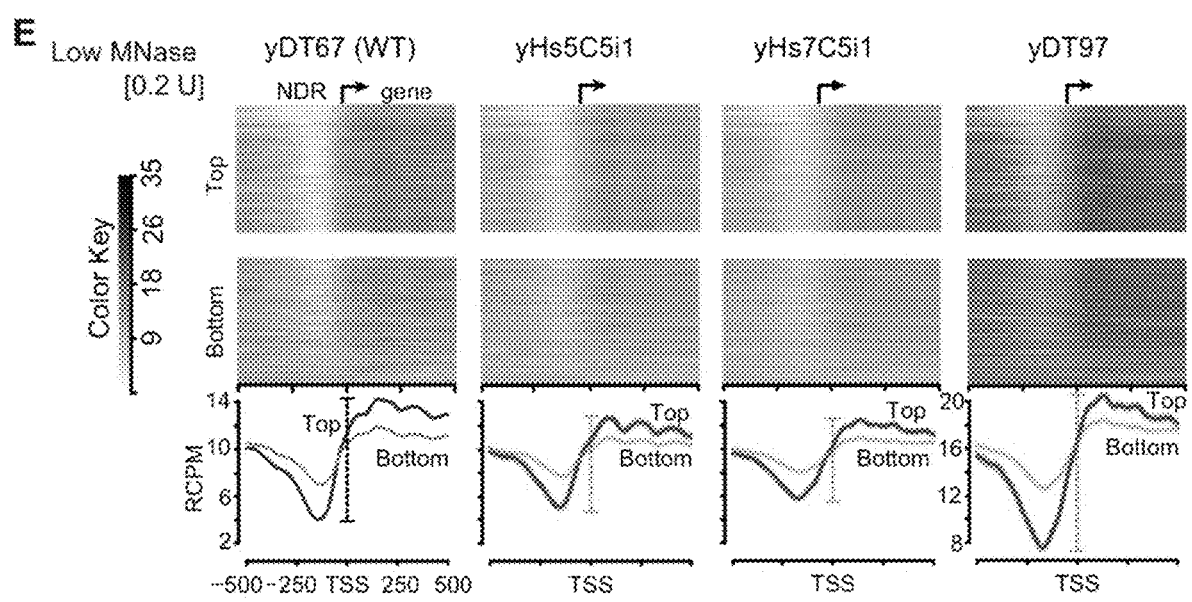

As predicted, total RNA content—predominantly mRNA and rRNA—is reduced by 6-8 fold in all the pre-evolved humanized yeast, and only slightly increased in the evolved and swapback strains (FIG. 6A). The mRNA to rRNA ratios remain similar to our isogenic-WT strain (FIG. 14A). However, tRNA sized molecule(s) are elevated relative to total RNA, and this may alter the balance of RNA types in the cell. However, we found the reduced total RNA is not explained by substantially altered cell numbers per A600 or reduced cell viability as determined by sytox green or trypan blue staining of dead cells (Kwolek-Mirek and Zadrag-Tecza, 2014) (FIG. 14B, C). Humanized whole-cell extracts had similar bulk protein yields to isogenic-WT, but the SDS-page gel stained with Coomassie shows numerous proteins with reduced levels, consistent with reduced RNA (FIG. 14D), whereas other presumably highly stable proteins are relatively unaffected. Immunoblots using antibodies more specific for human H3 and H4 show greater signal for humanized strains (FIG. 6B). Finally, both H3K4 trimethylation and H3K36 trimethylation signals were similar to the isogenic-WT strain, as these modifications are in regions conserved between yeast and humans. This suggests that low mRNA levels are not due to changes in these histone modifications.

The reduced RNA content and slowed growth might reflect differences in nucleosome dynamics (Chen et al., 2013), and could indicate a fundamental property of human histones or their relative inability to interact with yeast chromatin remodelers. To understand this effect, we mapped the MNase-seq reads across the transcription start sites (TSS) of the top 1500 genes by expression, and the bottom 1500 genes by expression. Genome-wide, the MNase-seq reveals a less "open" nucleosome depleted region (NDR) upstream of the TSS for humanized yeast than that found in isogenic-WT yeast (FIGS. 6C and 14E). The amplitude (difference between the NDR and gene bodies) is smaller for fully humanized yeast compared to isogenic-WT, suggesting reduced RNAP2 transcription that is consistent with the decreased total mRNA/rRNA content (FIG. 6A). The amplitude of highly expressed genes in humanized yeast looks more similar to the amplitude of the lowest expression genes in isogenic-WT. Even amongst themselves, the humanized strains show distinct nucleosome profiles, suggesting chromatin heterogeneity at the population-level. Furthermore, nucleosome fragment lengths at high concentration MNase of isogenic-WT yeast show a greater fraction of sub-nucleosomal particles (90-125 bp) compared to humanized yeast (~147 bp), suggesting that human chromatin is less accessible to MNase (FIG. 13C).

The above results combined with the poor environmental adaptability and cell cycle delays suggest that human nucleosomes are more generally repressive to RNAP2 transcription than yeast nucleosomes, possibly because they have a higher intrinsic affinity for DNA (the model we favor), thus making them more static, or are less easily removed by the yeast chromatin-remodelers, which did not coevolve with these histone sequences. Such a finding is consistent with the relatively more unstable nature of yeast chromatin in vitro compared to human chromatin (Leung et al., 2016), as well as their biology—yeast genes are predominantly expressed (Rando and Winston, 2012)—while humans repress the majority of the genome in virtually all cell types (Djebali et al., 2012; Talbert and Henikoff, 2017; Thurman et al., 2012) (Buschbeck and Hake, 2017). Thus, specialized histone variants with higher DNA affinity and stronger gene repression, might enable multicellular organisms to generate a larger variety of transcriptional landscapes.

Example 6

Suppressor Mutations and Human Chromatin "Memory" Enhance Humanization Frequency The numerous suppressor mutations identified earlier (FIG. 2) may counteract the various defects observed in yeast with human nucleosomes. If the suppressors make human histones more tolerable, they would be predicted to enhance the "humanization frequency". To determine this, we re-introduced the native yeast histone plasmid into 13 humanized suppressor strains (FIG. 7A; black dots), and allowed mitotic loss of the human histone plasmid, thus reverting these cells to native yeast chromatin, whereupon their growth properties improve. These lines were used for dual-plasmid histone shuffling as before, by reintroducing the human histone plasmid. The humanization frequencies, 10-100 fold greater than for non-suppressor ρ0 or ρ+ strains, confirms that the identified suppressors enhance tolerance of human nucleosomes. Furthermore, humanized colonies appeared as early as 12 days instead of the 20 originally required. These frequencies are high enough to support histone shuffling using any histone variant or from potentially any species.

While the suppressor mutations improved the humanization frequency going from native yeast chromatin to fully human chromatin, we also contemplated how readily human chromatin resists "invasion" by native yeast histones. If the humanization frequency improves in this scenario relative to the above, this might suggest maintenance of human chromatin, and a preference for re-incorporation of nucleosomes of their own type. To test this hypothesis, we re-introduced the native yeast histones into the fully humanized suppressor strains, and allowed for single colonies containing both types of chromatin to grow for approximately 26 cell division generations (FIG. 7A; red dots). This is a suitable time frame for native yeast chromatin to outcompete human chromatin, if not for "parental" nucleosome maintenance. Indeed, upon performing 5-FOA plasmid shuffling to remove the native yeast histones, the humanization frequencies reached 10-5-10-3, and cells appeared as early as 7 days.

We interpret this result to suggest that pre-existing human chromatin might help maintain chromatin of its own kind, at least regionally—a type of chromatin "memory" and transgenerational inheritance—thus pre-disposing some small fraction of cells to resist native yeast chromatin even after many cellular divisions. These results are surprising, as with few exceptions yeast do not have protein machinery dedicated to maintenance of different histone variants, let alone for human histones. In our model, (FIG. 7B) nucleosomes prefer their own type, thus seeding and maintaining similar chromatin domains. Therefore, different histone-types or nucleosome compositions are less likely to invade and outcompete this "parental" chromatin during the partitioning of chromatin during cellular division. This may occur in all cells or perhaps a smaller fraction of "older" cells that retain more of the earlier human chromatin. Finally, these results are consistent with our earlier observation demonstrating the relatively static nature of human core nucleosomes, thus making them more likely to maintain a certain epigenetic state.

From the foregoing Examples, the following will be apparent;

Because histones are some of the most conserved genes amongst eukaryotes, it was surprising that fully human nucleosomes so rarely led to bona fide humanized yeast. This speaks to the centrality of nucleosomes in regulating diverse cellular processes, including transcription and chromosome structure and movement. Cumulatively, our data suggest that human histones in yeast are deposited less efficiently, possibly due in part to sequence incompatibilities mapping to only 5 residues in the C-termini of H3 and H2A. When they do get deposited, the human histones lead to greater gene repression via less accessible NDRs, variations in chromatin, delayed environmental adaptation resulting from slowed chromatin remodeling, and depleted centromeres that possibly limit kinetochore assembly. The sum of these effect leads to partial cell-cycle arrest in G1 and a slower S-phase, which suppressor mutations in these same pathways alleviate.

The human core nucleosome, consisting of H3.1, H4, H2A.1 and H2B.1, may bind DNA more tightly, as it is predominantly deposited during DNA replication, (Campos et al., 2015) and then can remain in place for years, if not for decades, in a terminally differentiated state (Toyama et al., 2013). Earlier studies on in vitro reconstitution of yeast and mammalian nucleosomes suggested that mammalian nucleosomes bind DNA more readily, and that yeast nucleosomes are comparatively unstable (Lee et al., 1982). Given that yeast genes are generally euchromatic, and human genes are heterochromatic, this might indicate an evolutionary basis for histone sequence divergence. Yeast, which must readily adapt to new environments, evolved highly dynamic histones, that retain bifunctional characteristics of histone variants found in humans (Rando and Winston, 2012). For instance, yeast H3 acts as both as an H3.1 (replication-dependent) and H3.3 (replication-independent) variant, while yeast H2A acts as both an H2A.1 and H2A.X (DNA-damage) variant (Eriksson et al., 2012). In contrast, human cells must retain transcriptional states corresponding to cellular type. Thus, specialized histone variants with higher DNA affinity and stronger gene repression, enables multicellular organisms to generate more diverse transcriptional landscapes (Buschbeck and Hake, 2017). Indeed, these yeast with human nucleosomes had great difficulty adapting to new environmental conditions, perhaps due to the fundamentally more static biophysical properties of human core nucleosomes (Leung et al., 2016).

Furthermore, our data suggests that histone sequences do not contribute to the nucleosome repeat length (NRL), as the NRL of yeast with human histones remained yeast-like. In higher eukaryotes, longer linker length is partially attributed to linker histone H1 (Fan et al., 2005; Woodcock et al., 2006), but in yeast, it has been shown that expressing the human H1.2 linker had no effect on the NRL (Panday and Grove, 2016). In humans, the NRL ranges from ~178-205 bp, depending on histone modification state (Valouev et al., 2011), with activation marks having the shortest NRL. Thus, the underlying DNA sequence (Segal and Widom, 2009) and the proteins that interact with histones, such as Isw1a (Krietenstein et al., 2016), are more likely to specify this property.

Converting only five residues, 2 in H3, and 3 in H2A promoted relatively robust utilization of human nucleosomes as "Swapback" strains. In the case of human histone H3, the incompatibility with yeast may be attributed to an absence of two lysines required for ubiquitilation in yeast (Han et al., 2013). Human H2A may also poorly interact with yeast histone-interacting genes. However, this finding is still somewhat surprising as numerous other residues differ from yeast to humans that presumably should have larger roles—including many modified residues. As just one example, histone H3 position 42 is a lysine in yeast, but an arginine in humans (Hyland et al., 2011). Numerous other positions differ (FIG. 1A), thus, the relative inability to interact and modify histones at these different sites poses a serious question about the cumulative role of histone modifications during cell growth.

Figure 7:
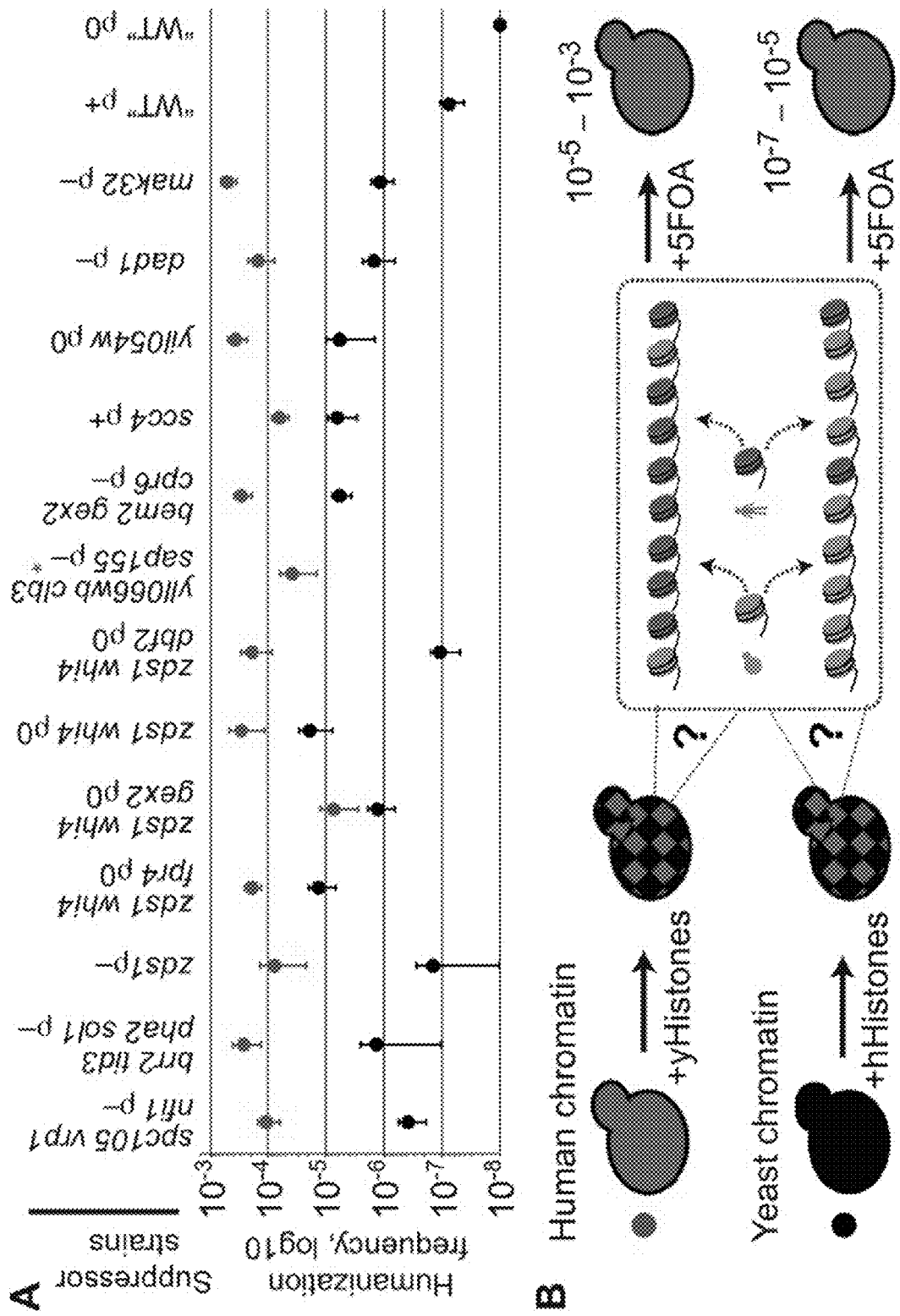
FIG. 7. "Re-humanization" of suppressor mutants starting with human or yeast chromatin. (A) Suppressor strains were "re-humanized" (see (B)), by generating a mixed chromatin environment (yeast+human), either starting from human chromatin (red dots) or native yeast chromatin (black dots). Genotypes are listed at top. The yHs suppressor strains were converted to a mixed chromatin environment, and then assayed by the dual-plasmid shuffle experiment. Each dot represents the mean of 3 or more experiments on a log 10 scale, and the bars are standard error of the mean. Suppressor strain with red asterisk was unable to lose human histone plasmid. (B) Diagram of suppressor strain "re-humanization" frequency experiments. Partitioning of nucleosomes between cells is poorly understood, especially in the context of variant histones. The dotted line inset with a question mark shows the possible chromatin states that may apply when yeast and human nucleosomes coexist and partition to new cells, showing how they may prefer their own histone sub-types.

Results presented herein suggests a type of chromatin partitioning "memory", as yeast with pre-existing human chromatin more readily resisted native yeast histones (FIG. 7). Histones are displaced from DNA during transcription, replication, and repair, and then reassembled onto DNA strands (Campos et al., 2014). How cells determine which histone sub-type and modification state must be deposited on the parent and daughter DNA strands in the replication fork remains a continuing question (Lai and Pugh, 2017). Based on our results, the restoration of nucleosomes to the parental strand and inheritance to the daughter strand may occur as a type of "semi-conservative replication" of chromatin, whereby both parent and daughter strands retain a portion of the ancestral nucleosome (human), and then may simply attract similarly composed or modified new nucleosomes. This may be a simple way to retain an epigenetic state. Our results argue against a "conservative" model, wherein daughter strands acquire only fresh nucleosomes. This model predicts that humanized yeast transformed with yeast histones, would react similarly to native yeast transformed with human histones (FIG. 7B). However, the results leave open the possibility of a "dispersive" model, which is a mixture of the two models. Nevertheless, humanized yeast may permit more systematic study of this process, coupled with future advances in single cell chromatin-profiling methods.

More generally, humanizing the chromatin of budding yeast provides new avenues to study fundamental properties of nucleosomes. We have explored some of these longstanding questions about histone variants: how they alter the dynamics of the genome at the structural and transcriptional level (Talbert and Henikoff, 2017); how they associate into different compositions of nucleosomes (Bernstein and Hake, 2006); and how they are partitioned and repositioned from cell-to-cell across generations (Budhavarapu et al., 2013; Campos et al., 2014). These questions remain fundamental, as many human cells are reprogrammed and differentiate using histone variants during development and disease (Santenard and Torres-Padilla, 2009; Wen et al., 2014). The number of histone variants found in humans is large, and includes many variants that accumulate during aging and disease. Thus, introducing foreign histones from a distant species into the simple yeast genome as described herein will help address these many questions.

Example 7

The following materials and methods were used to produce the results described above, and in the figures and tables of this disclosure.

Strains, plasmids, and media. All yeast strains used in this disclosure were haploid MATα, except as indicated in Table 5. Yeast to human complementation studies of histones H3 or H4 alone or in combination, were performed in strain yDT17. Strain yDT17 was generated by replacing the HHT1-HHF1 locus with NatMX4 by one-step PCR recombination, reintroducing HHT1-HHF1 on a URA3 containing pRS416 plasmid, and then replacing the HHT2-HHF2 locus with HygMX4. Experiments involving H2A or H2B alone or in combination used strain yDT30. Strain yDT30 was generated by replacing the HTA2-HTB2 locus with HygMX4, transformation with pRS416-HTA2HTB2, and then deleting the HTA1-HTB1 locus as above with KanMX4. Analysis of all four histones was performed in strain yDT51. yDT51 was generated similarly to the above, but contains plasmid yDT83 (pRS416-HTA2-HTAB2-HHT1-HHF1). The antibiotic markers (KanMX4, NatMX4, HygMX4) and the His3MX4 cassette used in replacing the four loci were reclaimed by deleting these open reading frames using the CRISPR/Cas9 system (DiCarlo et al., 2013) at the positions indicated with red arrows in FIG. 8A. Human histone genes were codon-optimized for yeast and synthesized by Epoch Biolabs. All cloning was performed by Gibson Assembly (Gibson et al., 2009). Swapback residue (human to yeast) histone variants were generated either by gene synthesis or site-directed mutagenesis. A complete list of available strains and plasmids are in the Supplemental Data.

Dual-plasmid histone shuffle assay. Shuffle strains (yDT17, yDT30, or yDT51), which already contains a set of yeast histones on a URA3 plasmid, were transformed by a standard Lithium Acetate protocol with a TRP1 human histone plasmid, which uses the endogenous promoters/ terminators from the other yeast histone set. Colonies were selected for 3 days at 30° C. on SC-Ura-Trp plates. Single colonies were picked and grown up overnight at 30° C. in 2 ml of SC-Trp. Spot assays (as indicated) were diluted 10-fold from overnight cultures ($A_{600}$ of ~10) and spotted on both SC-Trp and SC-Trp+5FOA plates. Shuffle assays for fully human nucleosomes using strain yDT51, were done as above, except 400 µl of overnight culture were spread onto a 10-cm SC-Trp+5FOA plate (25 ml) and incubated at 30° C. for up to 20 days in a sealed Tupper-ware container.

Plasmid isolation from yeast cells. Cells were harvested from 5 ml SC-Trp overnight culture and re-suspended in 600 µl of water and glass beads. Cells were vortexed for 10 minutes to disrupt cells. Plasmids were then isolated by alkaline lysis using the Zymo Zyppy miniprep kit and eluted in 20 µl of water. 5 µl was used to transform E. coli, and isolate pure plasmid.

PCRtag analysis. Crude genomic DNA was generated using a SDS/Lithium Acetate method (Looke et al., 2011). Comparative PCRtag analysis was performed using 0.5 µl of crude gDNA in a 20 µl GoTaqGreen Hot Start Polymerase reaction (Promega) containing 400 mM of each primer (Table 7). Reactions were run as follows: 95° C./5 min, followed by 35 cycles of (95° C./30 s, 62° C./30 s, 72° C./30 s) followed by a 72° C./2 min extension. A 10 µl aliquot was run on a 1% agarose/TTE gel.

Pulsed-field gel electrophoresis. Intact chromosomal DNA plugs were prepared as described elsewhere (Hage and Houseley, 2013). Chromosome identity was inferred from the known molecular karyotype of parental cells (yDT51) itself derived from S288C that was run on the same gel. Samples were run on a 1.0% agarose gel in 0.5×TBE for 24 h at 14° C. on a CHEF apparatus. The voltage was 6 V/cm, at an angle of 120° and 60-120 s switch time ramped over 24 h.

Mating and sporulation tests. Mating tester lawns (his1 strains 17/17 MATα or 17/14 MATα) were replica plated to YPD plates. A large amount of humanized strains (HIS1) were then smeared onto the replica plate to form rectangles, and then incubated overnight at 30° C. Plates were then replica plated onto synthetic defined (SD) plates and incubated overnight at 30° C. The diploids were sporulated for 7 days as previously described (Dai et al., 2008).

Microscopy. All yeast were grown to an $A_{600}$ of 0.5-0.9 in SC-Trp liquid media, and imaged under phase-contrast conditions at 100× magnification using a Nikon Eclipse Ti microscope. Cellular diameters were measure from 4 images each, comprising a total of 50 single cells. Violin plots and boxplots were generated using the R-package ggplot2.

Cell counting and viability. Cells were manually counted using a hemacytometer with Trypan blue vital dye under a microscope. Cell viability was also measured by incubating cells in 1 µM Sytox Green solution in PBS, and counting number of fluorescent cells (dead) by flow cytometry on a BD Accuri C6 flow cytometer. Coulter counting was performed using a Millipore Scepter by diluting log phase cultures 1:100 in PBS, and then taking up cells according to manufacturer's recommendations. Micromanipulation of single cells was performed using a Singer MSM 400 onto YPD plates.

Cell-cycle analysis using sytox green. Cell-cycle analysis by DNA content was adapted from (Rosebrock, 2017). Yeast were grown to log phase unless otherwise indicated in SC-Trp. Lag-phase for yDT67 took 45 min, whereas yDT97 took 2 h. Briefly, $10^7$ cells were fixed overnight in 70% EtOH overnight. Cells were incubated in 500 µl 2 mg/ml RNaseA solution for 2 h at 37° C. Then, 25 µl of 20 mg/ml Proteinase K solution was added, and cells incubated for 45 min at 37° C. Cells were washed and then stored in 1 ml 50 mM Tris pH 7.5. 50 µl of cells were re-suspended in 1 ml of 1 µM solution of Sytox Green (Thermofisher), and then 10,000 events were analyzed by flow cytometry on a BD Accuri C6 flow cytometer.

Flow cytometry of GAL1-eGFP induction. Strains as indicated were transformed by standard lithium acetate with plasmid pAV115-GAL-GFP, and selected on SC-Leu+2% glucose plates at 30° C. Single colonies were grown overnight at 30° C. in SC-Leu+glucose (2%). Cells were washed once in PBS, and then sub-cultured into SC-Leu+galactose (2%)+raffinose (1%) media and incubated at 30° C. For the times indicated, 25 µl of cells were diluted into 0.2 ml PBS and 10,000 events were analyzed by flow cytometry on a BD Accuri C6 flow cytometer.

"Re-humanization" of suppressor mutants starting with human or yeast chromatin. Humanized lineages were re-transformed with native yeast histone plasmid pDT83 (URA3) using standard Lithium Acetate transformation, and selected on SC-Ura-Trp plates for 4 days at 30° C. To determine the "human histone memory", single colonies were grown overnight in 2 ml SC-Trp and directly used in dual-plasmid histone shuffle as described above. To determine the "rehumanization" rate of suppressor mutations, single colonies from the above re-transformed strains were grown in SC-Ura for multiple sub-cultures to allow mitotic loss of the TRP1 human histone plasmid pDT109. Cells were replica plated onto SC-Ura and SC-Trp to identify those containing only the native yeast histones. These strains were then used for another round of dual-histone plasmid shuffle as described above.

Protein Analysis and Western Blotting. Whole-cell extracts were generated using a modified protocol from (Zhang et al., 2011). Briefly, $10^8$ log-phase yeast cells were re-suspended in 400 µl 0.15 M NaOH and 0.5 mM dithiothreitol (DTT), and incubated for 10 min on ice. Cells were pelleted at top speed for 10 min at 4° C., and re-suspended in 65 µl lysis buffer (20 mM HEPES pH 7.4, 0.1% Tween20, 2 mM MgCl2, 300 mM NaCl, 0.5 mM DTT, and 1 mM Roche Complete protease inhibitor) and an equal volume of 0.5 mm glass beads. Mixture was vortexed at top speed for 10 min in the cold room. Subsequently, 25 µl of NuPAGE (4×) LDS Sample buffer and 10 µl beta-mercaptoethanol was added, and the mixture was heated at >95° C. for 10 min. The debris was pelleted and the supernatant was run on a 12% Bis-Tris SDS acrylamide gel and stained with Coomassie blue.

Acid extracted histones were generated by first re-suspending $5 \times 10^8$ log-phase yeast in spheroblasting buffer (1.2M Sorbitol, 100 mM potassium phosphate pH 7.5, 1 mM $CaCl_2$, and 0.5 mM β-mercaptoethanol) containing Zymolase 40T (40 units/ml) and incubating for 20 min at 37° C. Spheroblasts were gently spun down at 3000 rpm for 3 min and then re-suspended in 1 ml of 0.5 M HCl/10% glycerol with glass beads on ice for 30 min. Cells were vortexed at top speed for 1 min every 5 min and kept on ice. Mixture was spun at 16,000×g for 10 min and the supernatant was added to 8 volumes of acetone and left at −20° C. overnight. The following day, mixture was pelleted for 5 min at 16,000×g, the solution poured off and the pellet was air-dried. Pellet was resuspended in 130 µl water, and then 50 µl NuPAGE (4×) LDS Sample buffer and 20 µl beta-mercaptoethanol was added, and the mixture was heated at >95° C. for 10 min. Supernatant was run on a 12% Bis-Tris SDS acrylamide gel and stained with Coomassie blue, or directly used for Western blotting.

Protein samples run on 12% Bis-Tris SDS acrylamide gel were transferred to membrane (Millipore, Immobilon-FL) using the BioRad Trans-Blot Turbo system according to manufacturer's recommendations. Membranes were blocked for 1.5 h at room temperature in 1:1 Tris-buffered saline (TB S)/Odyssey blocking buffer (LiCor). Blocking buffer was removed and membrane re-suspended in primary buffer overnight at 4° C. containing 1:1 TBS+0.05% Tween-20 (TBST)/Odyssey and the following antibodies used at 1:2,000 dilution: human H3 (abcam ab24834), H3K4me3 (abcam ab1012), H3K36me3 (abcam ab9050), human H4 (abcam ab10158). The following day, membrane was washed 5 times for 5 min each in TBST/Odyssey, re-suspended in secondary antibody buffer TBST/Odyssey/0.01% SDS with 1:20,000 dilution of both IRDye 800 goat anti-mouse and IRDye 680 goat anti-rabbit (LiCor) for 1.5 h at room temperature. Secondary was washed 5 times for 5 min each in TBST/Odyssey and then imaged using dual channels on a LiCor Odyssey CLx machine.

Growth assay on various types of solid media. Cultures were normalized to an $A_{600}$ of 10 and serially diluted in 10-fold increments in water and plated onto each type of medium. The following drugs and conditions were mixed into YPD+2% dextrose+2% agar: benomyl (15 µg/ml; microtubule inhibitor), camptothecin (0.5 µg/ml; topoisomerase inhibitor), hydroxyurea (0.2 M; defective DNA replication), NaOH (pH 9.0; vacuole formation defects), HCl (pH 4.0; vacuole formation defects), and methyl methanosulfate (MMS 0.05%; defective DNA repair). Galactose plates were prepared in Synthetic Complete media+1% raffinose and 2% galactose.

Whole genome sequencing and data analysis. Genomic DNA was isolated using Norgen Biotek's Fungal/Yeast Genomic DNA isolation kit, which included a spheroblasting step and bead-beating step. At least 1 µg of genomic DNA was used for Illumina library preparation using the Kapa Truseq library prep, and we routinely multiplexed 30 yeast genomes on a single HiSeq 4000 or 2500 lane.

Paired-end FASTQ files were aligned with the following pipeline. First, adapters, reads shorter than 50 bp, and poor quality reads near ends, were removed using Trimmomatic (Bolger et al., 2014). Data quality was assessed using FastQC. Processed reads were aligned to a custom genome reference (yDT51H.fa) using Burrows Wheeler aligner (BWA) mem algorithm (Li and Durbin, 2010), and Sam files were converted to sorted Bam files using Samtools (Li, 2011). Variants were called using the GATK "best practices" pipeline for Haplotype caller, custom scripts, and manually verified on the IGV viewer. Variants were identical using Samtools "mpileup". Read counts for each chromosome were determined from WGS Bam files using Bedtools "genome coverage" (Quinlan, 2014). Chromosome copy number was then calculated by generating boxplots in R using ggplot2. Networks for suppressor mutants were generated by uploading genes into the String online server (Szklarczyk et al., 2015). GO-terms were identified using the Panther database (Mi et al., 2016). Of the 37 mutations identified (Tables 1 and 2), 6 synonymous mutations were considered "innocuous" based on their similar codon usage.

MNase-digestions and MNase-sequencing. Experiments were adapted from (Kubik et al., 2015). Biological triplicate yeast colonies were each grown at 30° C. to an $A_{600}$ of ~0.9 in 100 ml of SC-Trp media. Cultures were crosslinked with 1% formaldehyde for 15 min at 25° C., and then quenched with 125 mM glycine. Cultures were washed twice in water, and pellets were then stored at −80° C. To perform MNase digestions, cells were first spheroplasted by suspending pellets in 4 ml spheroplasting buffer (1.2M Sorbitol, 100 mM potassium phosphate pH 7.5, 1 mM $CaCl_2$, and 0.5 mM β-mercaptoethanol) containing Zymolase 40T (40 units/ml) and incubated for 20 min at 37° C. Spheroblasts were gently washed twice with spheroblasting buffer, and then re-suspended in 1 ml digestion buffer (1M Sorbitol, 50 mM NaCl, 10 mM Tris-HCL (pH 7.4), 5 mM $MgCl_2$, 1 mM $CaCl_2$, 0.5 mM spermidine, 0.075% NP-40, and 1 mM β-mercaptoethanol). Samples were split into 500 µl aliquots equivalent to 50 ml culture each. To each sample, micrococcal nuclease (Sigma: N5386) was added to a final concentration for high digestion (2 units/ml) or low digestion (0.2 units/ml) or as specified in FIG. 13. Digestions proceeded at 37° C. for 45 minutes. Reactions were quenched with 16.6 µl of 0.5 M EDTA. Crosslinks were reversed in 0.5% SDS and 0.5 mg/ml proteinase K, by incubating at 37° C. for 1 h, followed by 65° C. for 2 h. Nucleic acid was extracted with phenol/chloroform twice, followed by chloroform. Nucleic acid was precipitated by adding 50 µl Sodium Acetate (3M, pH 5.2), an equal volume of isopropanol, and spinning for 20 min at 16,0000×g. Pellets were washed once with 70% EtOH, and then resuspended in 50 µl TE buffer containing 6 kUnitz of RNase A, and incubated for 30 min at 37° C. DNA was then purified using a Zymo DNA clean and concentrator, and eluted in 20 µl. MNase digested fragment DNA was measured by Qubit, and assessed on a 1.5% agarose TTE gel. At least 200 ng of DNA (PCR-free or minimal PCR of 2-3 cycles) for each replicate was used to generate a library for paired-end sequencing on an Illumina Hiseq 4000.

Nucleosome positioning analysis. MNase-seq FASTQ reads were processed using Trimmomatic (Bolger et al., 2014), FastQC, and then aligned to the sacCer3 reference genome using BWA-mem (Li and Durbin, 2010), and then converted to a sorted Bam file using samtools (Li, 2011). Custom bed files corresponding to the top and bottom 1500 genes, centromere regions, and tRNA regions were used to align MNase reads using Ngs.plot (Shen et al., 2014) to regions as specified. Fragment lengths were obtained from Sam files and plotted using ggplot2. Nucleosome dynamics were analyzed using DANPOS2 (Chen et al., 2013). Custom scripts were used to process the data to reduce erroneously called and altered nucleosomes as based on comparing MNase-seq data from WT experiment 1 against WT experiment 2 ("noise"). Nucleosome shifts passed the threshold when both nucleosome comparisons had aligned reads >300 and when shifts were greater than 70 bp. Nucleosome occupancies required that at least one nucleosome comparison have an aligned read count >300, and the False Discovery Rate (FDR) was lower than 0.05 with a $p<10^{-85}$. Fuzzy nucleosomes required that both nucleosome comparisons have read counts >300 and an FDR of <0.05.

TABLE 1

Figure 2:
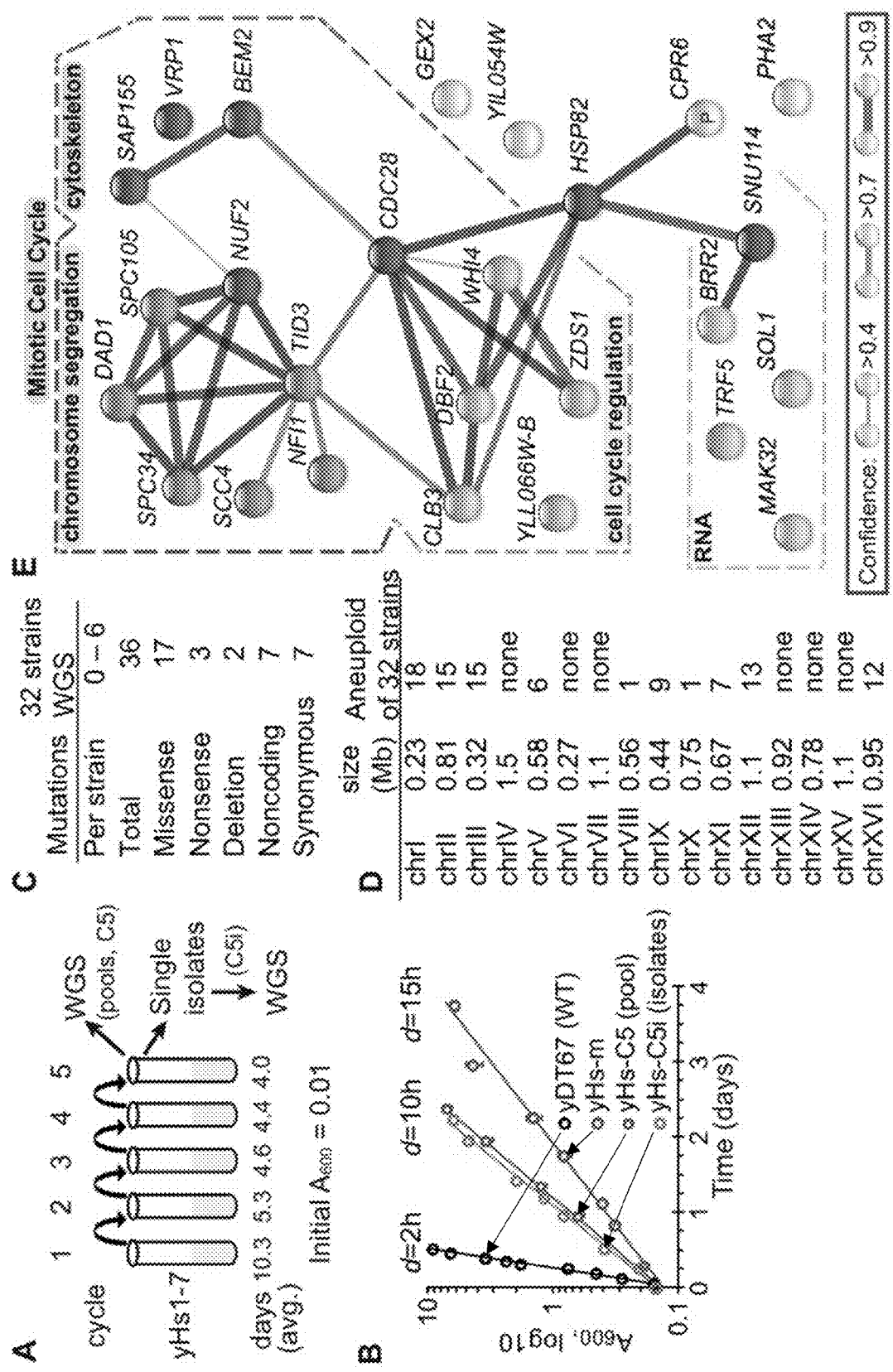
FIG. 2. Acquisition of bypass mutations in cell-cycle genes promotes growth with human nucleosomes. (A) Seven yHs-strains were evolved for 5 cycles in liquid medium (SC-Trp). (B) Growth rates and doubling times (d) in SC-Trp. Complete doubling times are listed in Table 2. (C) Types of DNA mutations identified by whole-genome sequencing (WGS). (D) Number of times each listed chromosome was scored as aneuploid. (E) 22 unique mutations identified by WGS (Tables 1 and 2) were constructed into a network ($p=5\times10^{-5}$) using the String algorithm (Szklarczyk et al., 2015). Colored nodes are in similar processes. Black nodes are top 4 interacting genes inferred from the network, but not arising as suppressors.

Whole genome sequencing mutations, Related to FIG. 2.

| Chr - Position | Gene | Mutation; pos | Amino acid Δ | Mut Effect | Function |
|---|---|---|---|---|---|
| 1 - 14,018 | TDA8 | A -> C; -275 | n/a | noncoding | Putative protein of unknown function |
| 3 - 142,928 | MAK32 | G -> T; 805 | A269S | missense | Stability of L-A dsRNA-containing particles |
| 3 - 130,008 | PGK1 | CTT -> C; -60 | n/a | noncoding | 3-phosphoglycerate kinase |
| 4 - 54,617 | WHI4 | G -> C; 1729 | H577D | missense | Regulates Start and commitment to cell division |
| 4 - 177,251 | CLB3 | C -> G; 480 | Y160stop | nonsense | Activates Cdc28 to promote the G2/M transition |
| 4 - 478,608 | DAD1 | G -> C; 150 | E50D | missense | Aids in chromosome segregation; DASH complex |
| 4 - 527,742 | ENA1 | T -> C; 2955 | S985S | synonymous | P-type ATPase sodium pump |
| - 527,796 | | T -> C; 2901 | S967S | synonymous | |
| - 527,850 | | T -> C; 2847 | T949T | synonymous | |
| 5 - 463,552 | SCC4 | C -> A; 193 | D65Y | missense | Cohesin loader; chromosome segregation |
| 5 - 478,709 | BEM2 | T -> G; 3042 | P1014P* | synonymous | Cytoskeleton organization; cellular morphogenesis |
| 5 - 528,878 | BRR2 | G -> T; 6046 | V2016F | missense | RNA helicase; spliceosome |
| 6 - 51,324 | YFL040W | T -> G; -26 | n/a | noncoding | Putative sugar transporter |
| 6 - 235,653 | SAP155 | T -> G; 1424 | V475G | missense | Essential for Sit4 (G1/S transition); DNA stress |
| 7 - 336,635 | SPC105 | G -> C; 1749 | R583S | missense | Bridges centromeric heterochromatin and kinetochore |
| 7 - 669,081 | DBF2 | A -> T; 889 | S297T | missense | Activated by Cdc15 during mitotic exit; regulates Clb2 |
| 8 - 461,050 | STB5 | A -> T; 1752 | A584A | synonymous | Transcription factor; regulates oxidative stress response |
| 9 - 79,776 | TID3 | A -> C; 1703 | E568A | missense | Kinetochore component; chromosome segregation |
| 9 - 254,845 | YIL054W | G -> C; 301 | D101H | missense | Protein of unknown function |
| 10 - 172,891 | URA2 | C -> G; -524 | n/a | noncoding | De novo biosynthesis of pyrimidines |
| 11 - 257,541 | MTC2 | T -> C; 768 | Y256Y | synonymous | Protein of unknown function; sick with cdc13-1 |
| 11 - 511,612 | SPC34 | T -> A; 188 | L63Q | missense | Aids in chromosome segregation; DASH complex |
| 11 - 660,938 - 662,785 | GEX2 | Deletion | n/a | deletion | Proton:glutathione antiporter; expressed at low level |
| 11 - 666,600 - 666,838 | TY5 | Deletion | n/a | deletion | Ty5 retrotransposon |
| 11 - 662,164 | GEX2 | A -> C; 721 | K241Q | missense | Proton:glutathione antiporter; expressed at low level |
| 12 - 5,742 | YLL066W-B | T -> C; 137 | F46S | missense | Overexpression causes cell-cycle delay or arrest |
| 12 - 573,283 | CPR6 | A -> G; -59 | n/a | noncoding | Binds Hsp82p and contributes to chaperone activity |
| 12 - 802,533 | VRP1 | C -> T; 176 | G59D | missense | Cytoskeleton organization and cytokinesis |
| 12 - 1,029,289 | FPR4 | G -> C; 858 | L286L | synonymous | Isomerization of proline residues in histones H3 and H4 |
| 13 - 477,824 | ARS1317 | A -> G; 240 | n/a | noncoding | Putative replication origin |
| 13 - 812,924 | ZDS1 | G -> T; 1036 | A346S | missense | Mitotic exit; maintains Cdc55; regulates Cdc14, Swe1 |
| 14 - 42,487 | PHA2 | C -> G; 592 | Q594E | missense | Phenylalanine biosynthesis pathway |
| 14 - 67,507 | TRE5 | C -> T; 988 | R329stop | nonsense | Nuclear RNA degradation; TRAMP complex; poly(A) pol |
| 14 - 689,433 | SOL1 | GT -> G; 882 | FV294Lstop | nonsense | DNA replication stress; tRNA export |
| 15 - 143,923 | TRM10 | C -> T; +227 | n/a | noncoding | DNA replication stress; tRNA methyltransferase |
| 15 - 630,433 | NFI1 | C -> G; 397 | V133L | missense | Sumoylates Cse4, Sir4, Yku70/80; regulates telomerase |

Mutation; pos refers to the nucleotide mutation and position relative to the sense strand ORF. Negative values (-X) indicate promoter mutations and positive values (+X) refer to terminator mutations. Synonymous mutations were considered innocuous if codon usage difference was <2-fold.
*Synonymous mutation codon usage was different: BEM2 (CCT (0.31) to CCG (0.12), all other cases codon usage was similar.

TABLE 2

Whole genome sequencing mutation genotypes by lineage, Related to FIG. 2.

| Isolate | Alias | Mutations | Presumed Innocuous Mutations | mtDNA ($\rho^{+/-/0}$) | Chromosome aneuploidy | Doubling (h:min) |
|---|---|---|---|---|---|---|
| | | | parent: yHs1 | | | |
| 1 original pool | yHs1 | — | tda8$^{(-275)}$ | $\rho^-$ | XII (2×) | n/t |
| 1 maintenance | yHs1m | n/t | n/t | n/t | n/t | 16:02 |
| 1 cycle 5 pool | yHs1C5 | — | tda8$^{(-275)}$ trm10$^{(+227)}$ | $\rho^-$ | I, II, III, V, IX, XI, XVI (2×) | 10:33 |
| 1 cycle 5 i1 | 1C5i1 | spc105$^{(R583S)}$ vrp1$^{(G59D)}$ nfi1$^{(V133L)}$ | tda8$^{(-275)}$ trm10$^{(+227)}$ mtc2$^{(Y256Y)}$ | $\rho^-$ | XII (2×) | 10:18 |
| 1 cycle 5 i2 | 1C5i2 | spc105$^{(R583S)}$ vrp1$^{(G59D)}$ nfi1$^{(V133L)}$ | tda8$^{(-275)}$ trm10$^{(+227)}$ mtc2$^{(Y256Y)}$ | $\rho^-$ | XII (2×) | n/t |
| 1 plate 5 i3 | 1PC5i3 | brr2$^{(V2016F)}$ tid3$^{(E568A)}$ pha2$^{(Q594E)}$ sol1$^{(FV294Lstop)}$ | tda8$^{(-275)}$ pgk1$^{(-60)}$ | $\rho^-$ | II, III, XII (2×) | 13:10 |
| 1 plate 5 i5 | 1PC5i5 | brr2$^{(V2016F)}$ tid3$^{(E568A)}$ pha2$^{(Q594E)}$ sol1$^{(FV294Lstop)}$ | tda8$^{(-275)}$ pgk1$^{(-60)}$ | $\rho^-$ | II, III, XII (2×) | n/t |
| | | | parent: yHs2 | | | |
| 2 original pool | yHs2 | zds1$^{(A346S)}$ | tda8$^{(-275)}$ | $\rho^-$ | I (2×); II, III, IX, XVI (1.5×) | n/t |
| 2 maintenance | yHs2m | n/t | n/t | n/t | n/t | 13:48 |
| 2 cycle 5 pool | yHs2C5 | zds1$^{(A346S)}$ | tda8$^{(-275)}$ | $\rho^-$ | I, XVI (2×); II, III, V, IX, XI (1.7×) | 10:39 |
| 2 cycle 5 i1 | 2C5i1 | zds1(A346S) stb5$^{(A584A)}$ | tda8$^{(-275)}$ ars1317$^{(240)}$ | $\rho^0$ | I (3×); III, XVI (2×); II, V, VIII, IX, XI (1.5×) | n/t |
| 2 plate 6 i1 | 2PC6i1 | zds1$^{(A346S)}$ stb5$^{(A584A)}$ | tda8$^{(-275)}$ | $\rho^0$ | I (2×) | 11:54 |
| 2 phe AE | phe2AE | zds1$^{(A346S)}$ whi4$^{(H577D)}$ | tda8$^{(-275)}$ fpr4$^{(L286L)}$ | $\rho^0$ | I (2×) | 8:56 |
| 2 phe AF | phe2AF | zds1$^{(A346S)}$ whi4$^{(H577D)}$ gex2$^{(K241Q)}$ | tda8$^{(-275)}$ | $\rho^0$ | — | 12:13 |
| 2 phe AH | phe2AH | zds1$^{(A346S)}$ whi4$^{(H577D)}$ | tda8$^{(-275)}$ | $\rho^0$ | I (2×); III (1.7×) | 9:16 |

TABLE 2-continued

Whole genome sequencing mutation genotypes by lineage, Related to FIG. 2.

| Isolate | Alias | Mutations | Presumed Innocuous Mutations | mtDNA ($\rho^{+/-/0}$) | Chromosome aneuploidy | Doubling (h:min) |
|---|---|---|---|---|---|---|
| 2 phe BC | phe2BC | zds1$^{(A346S)}$ whi4$^{(H577D)}$ | tda8$^{(-275)}$ | $\rho^0$ | I (2×); IX, XVI (1.5×) | 13:02 |
| 2 phe BD | phe2BD | zds1$^{(A346S)}$ whi4$^{(H577D)}$ | tda8$^{(-275)}$ | $\rho^0$ | I (1.8×); XVI (1.5×) | n/a |
| 2 phe 3C | phe23C | zds1$^{(A346S)}$ whi4$^{(H577D)}$ dbf2$^{(S297T)}$ | tda8(−275) yfl040w$^{(-26)}$ | $\rho^0$ | I (1.5×) | 10:18 |
| | | | parent: yHs3 | | | |
| 3 pool | yHs3 | yll066w-b$^{(F46S)}$ | tda8$^{(-275)}$ | $\rho^-$ | XII (2×); II (1.5×) | n/t |
| 3 maintenance | yHs3m | n/t | n/t | n/t | n/t | 13:25 |
| 3 cycle 5 pool | yHs3C5 | yll066w-b$^{(F46S)}$ clb3$^{(Y160stop)}$ | tda8$^{(-275)}$ | $\rho^-$ | I (2×) | 10:18 |
| 3 cycle 5 i1 | 3C5i1 | yll066w-b$^{(F46S)}$ clb3$^{(Y160stop)}$ sap155$^{(V475G)}$ | tda8$^{(-275)}$ | $\rho^-$ | I, II, III, IX, X, XVI (1.5×) | 12:00 |
| | | | parent: yHs4 | | | |
| 4 original pool | yHs4 | — | — | $\rho^-$ | XII (2×) | n/t |
| 4 maintenance | yHs4m | n/t | n/t | n/t | n/t | 15:37 |
| 4 cycle 5 pool | yHs4C5 | trf5$^{(R329stop)}$ | — | $\rho^-$ | I, III, XVI (1.5×) | 9:44 |
| 4 cycle 5 i1 | 4C5i1 | bem2$^{(P1014P)}$ gex2-ty5$^{(deletion)}$ cpr6$^{(-59)}$ | — | $\rho^-$ | — | 9:24 |
| | | | parent: yHs5 | | | |
| 5 original pool | yHs5 | scc4$^{(D65Y)}$ | — | $\rho^+$ | I, II, III, V, IX, XI, XII, XVI (2×) | n/t |
| 5 maintenance | yHs5m | n/t | n/t | n/t | n/t | 15:04 |
| 5 cycle 5 pool | yHs5C5 | scc4$^{(D65Y)}$ | — | $\rho^+$ | I, II, III, V, IX, XI, XII, XVI (1.5×) | 10:19 |
| 5 cycle 5 i1 | 5C5i1 | scc4$^{(D65Y)}$ | — | $\rho^+$ | I, II, III, V, IX, XI, XII, XVI (1.5×) | 9:44 |
| | | | parent: yHs6 | | | |
| 6 original pool | yHs6 | — | — | $\rho^0$ | II, XII (2×) | n/t |
| 6 maintenance | yHs6m | n/t | n/t | n/t | n/t | 17:54 |
| 6 cycle 5 pool | 6C5 | yil054W$^{(D101H)}$ | ena1$^{(T949T, S967S, S985S)}$ | $\rho^0$ | I, III, XVI (2×) | 9:53 |
| 6 cycle 5 i1 | 6C5i1 | yil054W$^{(D101H)}$ | ena1$^{(T949T, S967S, S985S)}$ | $\rho^0$ | I, II, III, XI, XVI (1.5×) | 10:23 |
| | | | parent: yHs7 | | | |
| 7 original pool | yHs7 | — | ura2$^{(-524)}$ | $\rho^-$ | XII (2×), II (1.5×) | n/t |
| 7 maintenance | yHs7m | n/t | n/t | n/t | n/t | 17:18 |
| 7 cycle 5 pool | yHs7C5 | dad1$^{(E50D)}$ | ura2$^{(-524)}$ | $\rho^-$ | — | 9:15 |
| 7 cycle 5 i1 | 7C5i1 | dad1$^{(E50D)}$ | ura2$^{(-524)}$ | $\rho^-$ | — | 9:20 |
| | | | parent: yHs8 | | | |
| 8 maintenance | yHs8m | mak32$^{(A269S)}$ | | $\rho^-$ | II, III, XII (1.5×) | 12:07 |
| | | | parent: yDT51 | | | |
| yDT98 | 8-swap strain | — | — | $\rho^+$ | III (2×) | ~4 |
| yDT97 | 5-swap strain | — | — | $\rho^+$ | VI (0.5×) | ~4 |
| yDT67 | WT | n/t | n/t | n/t | n/t | 1:50 |
| yDT51 | parental | — | — | $\rho^+$ | — | n/t |

All mutations are in 65% or greater of reads.

Spaces showing a " " indicate an absence of mutations or abnormalities, while "n/t" refers to not tested.

TABLE 3

Initial humanization trials.

| Strain | Human histones location | Plates (10$^7$ cells per plate | Human colonies | Date | Notes |
|---|---|---|---|---|---|
| yDT51 | Low-copy plasmid | 3 | 3 | Apr. 2, 2016 | 15 cm 20 ml plates |
| yDT51 | Low-copy plasmid | 4 | 4 | May 31, 2016 | 15 cm 20 ml plates |
| yDT51 | Low-copy plasmid | 20 | 1 | Jun. 10, 2016 | 15 cm 30 ml plates |
| yDT51 | Genomic integration at HO-locus | 10 | 0 | Jun. 10, 2016 | 15 cm 30 ml plates |
| yDT51 | 2-micron High-copy plasmid | 20 | 0 | Jun. 10, 2016 | 15 cm 30 ml plates |
| yDT51 | Low-copy plasmid | 3 | 1 | Nov. 10, 2016 | 15 cm 20 ml plates |

TABLE 4

Evolution cycles from FIG. 2A ($A_{600}$ starts at 0.01).

| | cycle 1 | | cycle 2 | | cycle 3 | | cycle 4 | | cycle 5 | |
|---|---|---|---|---|---|---|---|---|---|---|
| | $A_{600}$ | days | $A_{600}$ | days | $A_{600}$ | days | $A_{600}$ | days | $A_{600}$ | days |
| yHs1 | 4.0 | 15 | 5.1 | 10 | 6.1 | 8 | 6.6 | 6 | 2.3 | 4 |
| yHs2 | 5.3 | 11 | 6.2 | 6 | 4.2 | 4 | 7.2 | 5 | 5.4 | 4 |
| yHs3 | 6.9 | 11 | 6.2 | 6 | 5.1 | 5 | 6.5 | 5 | 2.5 | 4 |
| yHs4 | 5.2 | 8 | 6.3 | 4 | 6.2 | 4 | 4.9 | 4 | 5.9 | 4 |
| yHs5 | 6.8 | 7 | 4.0 | 4 | 7.1 | 4 | 6.0 | 4 | 6.6 | 4 |
| yHs6 | 5.3 | 10 | 6.3 | 4 | 4.0 | 3 | 6.4 | 3 | 6.3 | 4 |
| yHs7 | 6.0 | 10 | 4.8 | 7 | 5.0 | 4 | 5.3 | 4 | 6.2 | 4 |

TABLE 5

Strains used in this disclosure

| Strain name | Other name | MAT | Genotype |
|---|---|---|---|
| BY4741 | | a | leu2Δ0 met15Δ0 ura3Δ0 his3Δl |
| BY4742 | | α | leu2Δ0 lys2Δ0 ura3Δ0 his3Δ1 |
| yAS034 | 17/17 | α | his1 |
| yAS033 | 17/14 | a | his1 |
| yDT17 | H3/H4 | a | his3Δ200 leu2Δ1 lys2Δ202 trp1Δ63 ura3-52 hht1-hhf1::NatMX4 hht2-hhf2::HygMX4 [pDM9 (HHT1-HHF1/URA3/CEN-ARS/Amp)] |
| yDT30 | H2A/H2B | α | his3Δ200 leu2Δ0 lys2Δ0 trp1Δ63 ura3Δ0 met15Δ0 hta2-htb2::HygMX4 hta1-htb1::KanMX [pJD78 (HTA2-HTB2/URA3/CEN-ARS/Amp)] |
| yDT51 | parental shuffle | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT83 (pRS416-HTA2-HTB2-HHT1-HHF1/URA3/CEN-ARS/Amp)] |
| yDT67 | isogenic WT | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT105 (pRS414-HHT2-HHF2-HTA1-HTB1/TRP1/CEN-ARS/Amp)] |
| yDT64 | yHs1 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] tda8$^{(-275)}$ ρ$^-$ |
| yDT65 | yHs2 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ ρ$^-$ |
| yDT66 | yHs3 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] tda8$^{(-275)}$ yll066w-b$^{(F46S)}$ ρ$^-$ |
| yDT71 | yHs4 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] ρ$^-$ |
| yDT72 | yHs5 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] scc4$^{(D65Y)}$ ρ$^+$ |
| yDT73 | yHs6 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] ρ$^0$ |
| yDT74 | yHs7 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] ura2$^{(-524)}$ ρ$^-$ |
| yDT79 | yHs8 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] mak32$^{(A269S)}$ ρ$^-$ |
| yDT75 | yHs1C5 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] tda8$^{(-275)}$ trm10$^{(+227)}$ ρ$^-$ |
| yDT76 | yHs2C5 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ ρ$^-$ |
| yDT77 | yHs3C5 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] tda8$^{(-275)}$ yll066w-b$^{(F46S)}$ clb3$^{(Y160stop)}$ ρ$^-$ |
| yDT81 | yHs4C5 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] trf5$^{(R329stop)}$ ρ$^-$ |
| yDT82 | yHs5C5 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] scc4$^{(D65Y)}$ ρ$^+$ |
| yDT83 | yHs6C5 | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT109 (pRS414-hH3.1-hH4-hH2A-hH2B/TRP1/CEN-ARS/Amp)] ena1$^{(T949T, S967S, S985S)}$ yil054W$^{(D101H)}$ ρ$^0$ |

TABLE 5-continued

Strains used in this disclosure

| Strain name | Other name | MAT | Genotype |
|---|---|---|---|
| yDT84 | yHs7C5 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] dad1$^{(E50D)}$ ura2$^{(-524)}$ ρ$^-$ |
| yDT86 | yHs1C5i2 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ trm10$^{(+227)}$ mtc2$^{(Y256Y)}$ spc105$^{R583S}$ vrp1$^{(G59D)}$ nfi1$^{(V133L)}$ ρ$^-$ |
| yDT87 | yHs2C5i1 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ ars1317$^{(240)}$ stb5$^{(A584A)}$ ρ$^0$ |
| yDT88 | yHs3C5i1 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (PRS414-hH3.1-hH4-hH2A-hH2B/TRP1/CEN-ARS/Amp)] tda8$^{(-275)}$ yll066w-b$^{(F46S)}$ clb3$^{(Y160stop)}$ sap155$^{(V475G)}$ ρ$^-$ |
| yDT94 | yHs4C5i1 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] bem2$^{(P1014P)}$ gex2-ty5$^{(deletion)}$ cpr6$^{(-59)}$ ρ$^-$ |
| yDT92 | yHs5C5i1 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] scc4$^{(D65Y)}$ ρ$^+$ |
| yDT93 | yHs6C5i1 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] ena1$^{(T949T, S967S, S985S)}$ yil054W$^{(D101H)}$ ρ$^0$ |
| yDT95 | yHs7C5i1 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] dad1$^{(E50D)}$ ura2$^{(-524)}$ ρ$^-$ |
| yDT85 | 2PC6i1 | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ stb5$^{(A584A)}$ ρ$^-$ |
| yDT105 | phe2AE | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ whi4$^{(H577D)}$ fpr4$^{(L286L)}$ ρ$^0$ |
| yDT106 | phe2AF | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ whi4$^{(H577D)}$ gex2$^{(K241Q)}$ ρ$^0$ |
| yDT107 | pheAH | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ whi4$^{(H577D)}$ ρ$^0$ |
| yDT109 | pheBC | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ whi4$^{(H577D)}$ ρ$^0$ |
| yDT108 | phe23C | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT109 (pRS414-hH3.1-hH4-hH2A-hH2B/TRP1/CEN-ARS/Amp)] tda8$^{(-275)}$ zds1$^{(A346S)}$ whi4$^{(H577D)}$ dbf2$^{(S297T)}$ yfl040w$^{(-26)}$ ρ$^0$ |
| yDT97 | 5-residue swap | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 pDT128 (pRS414-hH3.1KK-hH4-hH2A$_C$-hH2B/TRP1/CEN-ARS/Amp)] |
| yDT98 | 8-residue swap | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 pDT130 (pRS414-hH3.1KK-hH4-hH2AN$_C$-hH2B/TRP1/CEN-ARS/Amp)] |
| yDT124 | 1B 1C5i2 shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] tda8$^{(-275)}$ trm10$^{(+227)}$ mtc2$^{(Y256Y)}$ spc105$^{R583S}$ vrp1$^{(G59D)}$ nfi1$^{(V133L)}$ ρ$^-$ |
| yDT125 | 2A p1C5i3 shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] tda8$^{(-275)}$ pgk1$^{(-60)}$ brr2$^{(V2016F)}$ tid3$^{(E568A)}$ pha2$^{(Q594E)}$ sol1$^{(FV294Lstop)}$ ρ$^-$ |
| yDT128 | 4A 2pC6i1 shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] tda8$^{(-275)}$ zds1$^{(A346S)}$ stb5$^{(A584A)}$ ρ$^-$ |
| yDT130 | 5A phe2AE shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [[pDT83 (pRS416-HTA2-HTB2-HHT1-HHF1/URA3/CEN-ARS/Amp)] tda8$^{(-275)}$ zds1$^{(A346S)}$ whi4$^{(H577D)}$ fpr4$^{(L286L)}$ ρ$^0$ |
| yDT132 | 6A phe2AF shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] tda8$^{(-275)}$ zds1$^{(A346S)}$ whi4$^{(H577D)}$ gex2$^{(K241Q)}$ ρ$^0$ |
| yDT134 | 7A phe2AH shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] tda8$^{(-275)}$ zds1$^{(A346S)}$ whi4$^{(H577D)}$ ρ$^0$ |
| yDT136 | 8A phe2BC shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] tda8$^{(-275)}$ zds1$^{(A346S)}$ whi4$^{(H577D)}$ ρ$^0$ |
| yDT138 | 9A phe23C shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] tda8$^{(-275)}$ zds1$^{(A346S)}$ whi4$^{(H577D)}$ dbf2$^{(S297T)}$ yfl040w$^{(-26)}$ ρ$^0$ |
| yDT140 | 11A 4C5i1 shuffle | α | his3Δ200 leu2Δ0 lys2Δ0 trp1Δ63 ura3Δ0 met15Δ0 hta2-htb2Δ0 hta1-htb1Δ0 hhf1-hhf1Δ0 hht2-hhf2Δ0 [pDT83 (pRS416-HTA2-HTB2-HHT1-HHF1/URA3/CEN-ARS/Amp)] bem2$^{(P1014P)}$ gex2-ty5$^{(deletion)}$ cpr6$^{(-59)}$ ρ$^-$ |

TABLE 5-continued

Strains used in this disclosure

| Strain name | Other name | MAT | Genotype |
|---|---|---|---|
| yDT142 | 14A 7C5i1 shuffle | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT83 (pRS416-HTA2-HTB2-HHT1-HHF1/URA3/CEN-ARS/Amp)] dad1$^{(E50D)}$ ura2$^{(-524)}$ ρ$^-$ |
| yDT148 | 12A 5C5i1 shuffle | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT83 (pRS416-HTA2-HTB2-HHT1-HHF1/URA3/CEN-ARS/Amp)] scc4$^{(D65Y)}$ ρ$^+$ |
| yDT152 | 13A 6C5i1 shuffle | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT83 (pRS416-HTA2-HTB2-HHT1-HHF1/URA3/CEN-ARS/Amp)] ena1$^{(T949I, S967S, S985S)}$ yil054W$^{(D101H)}$ ρ$^0$ |
| yDT154 | 15A yHs8 shuffle | α | his3Δ200 leu2Δ0 lys2Δ0 trp1Δ63 ura3Δ0 met15Δ0 hta2-htb2Δ0 hta1-htb1Δ0 hht1-hhf1Δ0 hht2-hhf2Δ0 [pDT83 (pRS416-HTA2-HTB2-HHT1-HHF1/URA3/CEN-ARS/Amp)] mak32$^{(A269S)}$ ρ$^-$ |

TABLE 6

Plasmids

| Plasmid name | Other name | Plasmid markers | Description |
|---|---|---|---|
| pDT076 | pRS414-HTA1HTB1 | amp/Trp | pRS414 with HTA1, HTA1/HTB1 promoter, HTB1, each gene flanked by restriction sites. CYC1 and ADH1 terminators. |
| pDT077 | pRS414-hH2AhH2B | amp/Trp | pRS414 with human H2A, HTA1/HTB1 promoter, human H2B, each gene flanked by restriction sites. CYC1 and ADH1 terminators. |
| pDT083 | yHistones | amp/Ura | pRS416-HTA2-HTB2-HHT1-HHF1. Shuffle plasmid, parental strain. |
| pDT100 | | amp/Trp | pRS414-hH3.1QKK-hH4 |
| pDT101 | | amp/Trp | pRS414-hH3.1KK-hH4 |
| pDT102 | | amp/Trp | pRS414-hH3.3QKK-hH4 |
| pDT103 | | amp/Trp | pRS414-hH3.3KK-hH4 |
| pDT105 | yHistones2 | amp/Trp | pRS414-HHT2-HHF2-HTA-HTB1. Isogenic-WT plasmid. |
| pDT107 | | amp/Trp | pRS414-hH3.-hH4-hH2A-hH2B (HHT2F2HTA1B1 PROs/TERs) |
| pDT108 | | amp/Trp | pRS414-hH3.1QKK-hH4-hH2A-hH2B (HHT2F2HTA1B1 PROs/TERs) |
| pDT109 | hHistones | amp/Trp | pRS414-hH3.1-hH4-hH2A-hH2B (HHT2F2HTA1B1 PROs/TERs). yHs strains. |
| pDT110 | | amp/Trp | pRS414-hH3.1KK-hH4-hH2A-hH2B (HHT2F2HTA1B1 PROs/TERs) |
| pDT111 | | amp/Trp | pRS414-hH3.1QKK-hH4-hH2A2+4-hH2B (HHT2F2HTA1B1 PROs/TERs) |
| pDT112 | | amp/Trp | pRS414-hH3.1QKK-hH4-hH2A4-hH2B (HHT2F2HTA1B1 PROs/TERs) |
| pDT113 | | amp/Trp | pRS414-1H43.1KK-hH4-hH2A2+4-hH2B (HHT2F2HTA1B1 PROs/TERs) |
| pDT114 | | amp/Trp | pRS414-1H43.1KK-hH4-hH2A4-hH2B (HHT2F2HTA1B1 PROs/TERs) |
| pDT116 | | amp/Leu | E99 with hH3.1hH4hH2A4hH2B(HHT2F2HTA1B1 PROs/TERs) cloned in place of RFP. HO-integration vector with Leu tag. |
| pDT121 | | amp/Trp | pRS414-hH2A$_{NC}$-hH2B |
| pDT125 | | amp/Trp | pRS414-hH3.1-hH4-hH2A$_C$-hH2B (HHT2F2HTA1B1 PROs/TERs) |
| pDT126 | | amp/Trp | pRS414-hH3.1-hH4-hH2A$_N$-hH2B (HHT2F2HTA1B1 PROs/TERs) |
| pDT127 | | amp/Trp | pRS414-hH3.1-hH4-hH2A$_{NC}$-hH2B (HHT2F2HTA1B1 PROs/TERs) |
| pDT128 | | amp/Trp | pRS414-hH3.1KK-hH4-hH2A$_C$-hH2B (HHT2F2HTA1B1 PROs/TERs) |
| pDT130 | | amp/Trp | pRS414-hH3.1KK-hH4-hH2A$_{NC}$-hH2B (HHT2F2HTA1B1 PROs/TERs) |
| pDT130 | | amp/Trp | pRS424-hH3.1-hH4-hH2A-hH2B (HHT2F2HTA1B1 PROs/TERs) 2 micron version |

TABLE 7

PCRtag primers.

| Primer name | Target | Species | Orientation | Sequence |
|---|---|---|---|---|
| JB00133_DT | HTB1/2 | Yeast | Forward | GGTAACAGCTCTAGTACCTTCAGAG (SEQ ID NO: 1) |

TABLE 7-continued

PCRtaq primers.

| Primer name | Target | Species | Orientation | Sequence |
|---|---|---|---|---|
| JB00134_DT | HTB1/2 | Yeast | Reverse | GCCGAAAAGAAACCAGC (SEQ ID NO: 2) |
| JB00137_DT | HTA1/2 | Yeast | Forward | AGGTGGTAAAGCTGGTTCAG (SEQ ID NO: 3) |
| JB00138_DT | HTA1/2 | Yeast | Reverse | TTCTTGAGAAGCCTTGGTAGC (SEQ ID NO: 4) |
| DT484 | HHT1/2 | Yeast | Forward | GCTGCCAGAAAATCCGCC (SEQ ID NO: 5) |
| DT557 | HHT1/2 | Yeast | Reverse | GCCAACTTGATATCCTTCTTTTGGATAGT (SEQ ID NO: 6) |
| DT488 | HHF1/2 | Yeast | Forward | AGAGGTAAAGGTGGTAAAGGTCTA (SEQ ID NO: 7) |
| DT567 | HHF1/2 | Yeast | Reverse | GGATTTCAAGACNGCTCTGAC (SEQ ID NO: 8) |
| JB00131_DT | hH2B.J | Human | Forward | GTAACAGCCTTGGTACCTTCAG (SEQ ID NO: 9) |
| JB00132_DT | hH2B.J | Human | Reverse | AACCAGCTAAGTCTGCTCCAG (SEQ ID NO: 10) |
| JB00135_DT | hH2A.I | Human | Forward | AGAGGTAAGCAAGGTGGTAAGG (SEQ ID NO: 11) |
| JB00136_DT | hH2A.I | Human | Reverse | CTTACCCTTAGCCTTGTGGTG (SEQ ID NO: 12) |
| DT482 | hH3 | Human | Forward | AGGCTGCTAGAAAGTCTGCT (SEQ ID NO: 13) |
| DT483 | hH3 | Human | Reverse | TCTCTTAGCGTGGATAGCACA (SEQ ID NO: 14) |
| DT565 | hH4 | Human | Forward | GGTGGTAAGGGTTTGGGTAAG (SEQ ID NO: 15) |
| DT566 | hH4 | Human | Reverse | GAAAACCTTCAAAACACCTCTGGT (SEQ ID NO: 16) |

TABLE 8

Illumina high-throughput whole-genome sequencing files

| SRA accession | Type | File name 1 | File name 2 | Description | Filesize (Gb) | Date |
|---|---|---|---|---|---|---|
| SRR5359525 | PE150 | yDT51_R1_001.fastq.gz | yDT5l_R2_001.fastq.gz | WGS of parental strain | 1.46; 1.67 | Jul. 19, 2016 |
| SRR5359524 | PE150 | yHsl_R1_001.fastq.gz | yHs1_R2_001.fastq.gz | WGS of yHs1 original | 1.27; 1.47 | Jul. 19, 2016 |
| SRR5359523 | PE150 | yHs2_R1_001.fastq.gz | yHs2_R2_001.fastq.gz | WGS of yHs2 original | 1.32; 1.52 | Jul. 19, 2016 |
| SRR5359522 | PE150 | yHs3_R1_001.fastq.gz | yHs3_R2_001.fastq.gz | WGS of yHs3 original | 1.41; 1.61 | Jul. 19, 2016 |
| SRR5359521 | PE150 | yHs1m_R1_001.fastq.gz | yHs1m_R2_001.fastq.gz | WGS of yHs1 maintenance | 1.30; 1.50 | Jul. 19, 2016 |
| SRR5359520 | PE150 | yHs2m_R1_001.fastq.gz | yHs2m_R2_001.fastq.gz | WGS of yHs2 maintenance | 1.41; 1.62 | Jul. 19, 2016 |
| SRR5359519 | PE150 | yHs3m_R1_001.fastq.gz | yHs3m_R2_001.fastq.gz | WGS of yHs3 maintenance | 1.41; 1.61 | Jul. 19, 2016 |
| SRR5359518 | PE150 | yHs4_R1_001.fastq.gz | yHs4_R2_001.fastq.gz | WGS of yHs4 original | 1.38; 1.60 | Jul. 19, 2016 |
| SRR5359517 | PE150 | yHs5_R1_001.fastq.gz | yHs5_R2_001.fastq.gz | WGS of yHs5 original | 1.32; 1.53 | Jul. 19, 2016 |
| SRR5359516 | PE150 | yHs7_R1_001.fastq.gz | yHs7_R2_001.fastq.gz | WGS of yHs7 original | 1.41; 1.62 | Jul. 19, 2016 |
| SRR5359515 | PE150 | yHs1C5_R1_001.fastq.gz | yHs1C5_R2_001.fastq.gz | WGS of yHs1 cycle 5 | 1.44; 1.65 | Jul. 19, 2016 |
| SRR5359514 | PE150 | yHs2C5_R1_001.fastq.gz | yHs2C5_R2_001.fastq.gz | WGS of yHs2 cycle 5 | 1.28; 1.45 | Jul. 19, 2016 |
| SRR5359513 | PE150 | yHs3C5_R1_001.fastq.gz | yHs3C5_R2_001.fastq.gz | WGS of yHs3 cycle 5 | 1.36; 1.56 | Jul. 19, 2016 |
| SRR5359512 | PE100 | yHs6_R1_001.fastq.gz | yHs6_R2_001.fastq.gz | WGS of yHs6 original | 0.53; 0.52 | Sep. 2, 2016 |
| SRR5359511 | PE100 | yHs8_R1_001.fastq.gz | yHs8_R2_001.fastq.gz | WGS of yHs8 original | 0.60; 0.59 | Sep. 2, 2016 |
| SRR5359510 | PE100 | yHs4C5_R1_001.fastq.gz | yHs4C5_R2_001.fastq.gz | WGS of yHs4 cycle 5 | 0.96; 0.94 | Sep. 2, 2016 |
| SRR5359509 | PE100 | yHs5C5_R1_001.fastq.gz | yHs5C5_R2_001.fastq.gz | WGS of yHs5 cycle 5 | 0.75; 0.74 | Sep. 2, 2016 |
| SRR5359508 | PE100 | yHs6C5_R1_001.fastq.gz | yHs6C5_R2_001.fastq.gz | WGS of yHs6 cycle 5 | 0.53; 0.52 | Sep. 2, 2016 |
| SRR5359507 | PE100 | yHs7C5_R1_001.fastq.gz | yHs7C5_R2_001.fastq.gz | WGS of yHs7 cycle 5 | 0.52; 0.52 | Sep. 2, 2016 |
| SRR5359506 | PE100 | yHs1C5i2_R1_001.fastq.gz | yHs1C5i2_R2_001.fastq.gz | WGS of yHs1 cycle 5 isolate 2 | 0.56; 0.55 | Sep. 2, 2016 |

TABLE 8-continued

Illumina high-throughput whole-genome sequencing files

| SRA accession | Type | File name 1 | File name 2 | Description | Filesize (Gb) | Date |
|---|---|---|---|---|---|---|
| SRR5359505 | PE100 | yHs2C5i1_R1_001.fastq.gz | yHs2C5i1_R2_001.fastq.gz | WGS of yHs2 cycle 5 isolate 1 | 1.01; 0.99 | Sep. 2, 2016 |
| SRR5359504 | PE100 | yHs3C5i1_R1_001.fastq.gz | yHs3C5i1_R2_001.fastq.gz | WGS of yHs3 cycle 5 isolate 1 | 0.71; 0.96 | Sep. 2, 2016 |
| SRR5359503 | PE100 | yHs4C5i1_R1_001.fastq.gz | yHs4C5i1_R2_001.fastq.gz | WGS of yHs4 cycle 5 isolate 1 | 0.68; 0.68 | Sep. 2, 2016 |
| SRR5359502 | PE100 | yHs5C5i1_R1_001.fastq.gz | yHs5C5i1_R2_001.fastq.gz | WGS of yHs5 cycle 5 isolate 1 | 0.82; 0.81 | Sep. 2, 2016 |
| SRR5359501 | PE100 | yHs6C5i1_R1_001.fastq.gz | yHs6C5i1_R2_001.fastq.gz | WGS of yHs6 cycle 5 isolate 1 | 0.58; 0.58 | Sep. 2, 2016 |
| SRR5359500 | PE100 | yHs7C5i1_R1_001.fastq.gz | yHs7C5i1_R2_001.fastq.gz | WGS of yHs7 cycle 5 isolate 1 | 0.69; 0.68 | Sep. 2, 2016 |
| SRR5359499 | PE100 | phe2AE_R1_001.fastq.gz | phe2AE_R2_001.fastq.gz | WGS of phe2AE | 0.77; 0.76 | Sep. 2, 2016 |
| SRR5359498 | PE100 | phe2AF_R1_001.fastq.gz | phe2AF_R2_001.fastq.gz | WGS of phe2AF | 0.45; 0.45 | Sep. 2, 2016 |
| SRR5359497 | PE100 | phe2AH_R1_001.fastq.gz | phe2AH_R2_001.fastq.gz | WGS of phe2AH | 0.68; 0.67 | Sep. 2, 2016 |
| SRR5359496 | PE100 | phe2BC_R1_001.fastq.gz | phe2BC_R2_001.fastq.gz | WGS of phe2BC | 0.67; 0.69 | Sep. 2, 2016 |
| SRR5359495 | PE100 | phe2BD_R1_001.fastq.gz | phe2BD_R2_001.fastq.gz | WGS of phe2BD | 0.57; 0.56 | Sep. 2, 2016 |
| SRR5359494 | PE100 | phe23C_R1_001.fastq.gz | phe23C_R2_001.fastq.gz | WGS of phe23C | 0.55; 0.55 | Sep. 2, 2016 |
| SRR5359493 | PE100 | 2PC6i1_R1_001.fastq.gz | 2PC6i1_R2_001.fastq.gz | WGS of yHs2 plate cycle 6 isolate 1 | 0.54; 0.53 | Sep. 2, 2016 |
| SRR5359492 | PE100 | yHs1C5i1_R1_001.fastq.gz | yHs1C5i1_R2_001.fastq.gz | WGS of yHs1 cycle 5 isolate 1 | 0.61; 0.60 | Sep. 2, 2016 |
| SRR5359491 | PE100 | 1PC5i5_R1_001.fastq.gz | 1PC5i5_R2_001.fastq.gz | WGS of yHs1 plate cycle 5 isolate 5 | 0.58; 0.58 | Sep. 2, 2016 |
| SRR5359490 | PE100 | 1PC5i3_R1_001.fastq.gz | 1PC5i3_R2_001.fastq.gz | WGS of yHs1 plate cycle 5 isolate 3 | 0.37; 0.36 | Sep. 2, 2016 |
| SRR5359489 | PE100 | yDT97_R1_001.fastq.gz | yDT97_R2_001.fastq.gz | WGS of yDT97 | 0.78; 0.73 | Sep. 2, 2016 |
| SRR5359488 | PE100 | yDT98_R1_001.fastq.gz | yDT98_R2_001.fastq.gz | WGS of yDT98 | 0.82; 0.80 | Sep. 2, 2016 |

TABLE 9

Illumina high-throughput MNase DNA sequencing files

| SRA accession | Type | File name 1 | File name 2 | Description | Filesize (Gb) | Date |
|---|---|---|---|---|---|---|
| SAMN06619428 | PE150 | WTH1_R1_001.fastq.gz | WTH1_R2_001.fastq.gz | yDT67 (WT) high MNase experiment 1, bio rep 1 | 0.76; 0.89 | Dec. 8, 2016 |
| SAMN06619429 | PE150 | WTH2_R1_001.fastq.gz | WTH2_R2_001.fastq.gz | yDT67 (WT) high MNase experiment 1, bio rep 2 | 0.73; 0.85 | Dec. 8, 2016 |
| SAMN06619430 | PE150 | WTH3_R1_001.fastq.gz | WTH3_R2_001.fastq.gz | yDT67 (WT) high MNase experiment 1, bio rep 3 | 0.69; 0.80 | Dec. 8, 2016 |
| SAMN06619431 | PE150 | WTL1_R1_001.fastq.gz | WTL1_R2_001.fastq.gz | yDT67 (WT) low MNase experiment 1, bio rep 1 | 0.87; 0.99 | Dec. 8, 2016 |
| SAMN06619432 | PE150 | WTL2_R1_001.fastq.gz | WTL2_R2_001.fastq.gz | yDT67 (WT) low MNase experiment 1, bio rep 2 | 0.93; 1.09 | Dec. 8, 2016 |
| SAMN06619433 | PE150 | WTL3_R1_001.fastq.gz | WTL3_R2_001.fastq.gz | yDT67 (WT) low MNase experiment 1, bio rep 3 | 0.85; 0.98 | Dec. 8, 2016 |
| SAMN06619434 | PE150 | 5C5iH1_R1_001.fastq.gz | 5C5iHl_R2_001.fastq.gz | yHs5C5i1 high MNase experiment 1, bio rep 1 | 0.87; 1.00 | Dec. 8, 2016 |
| SAMN06619435 | PE150 | 5C5iH2_R1_001.fastq.gz | 5C5iH2_R2_001.fastq.gz | yHs5C5i1 high MNase experiment 1, bio rep 2 | 0.83; 1.00 | Dec. 8, 2016 |
| SAMN06619436 | PE150 | 5C5iH3_R1_001.fastq.gz | 5C5iH3_R2_001.fastq.gz | yHs5C5i1 high MNase experiment 1, bio rep 3 | 0.86; 1.00 | Dec. 8, 2016 |
| SAMN06619437 | PE150 | 5C5iL1_R1_001.fastq.gz | 5C5iL1_R2_001.fastq.gz | yHs5C5i1 low MNase experiment 1, bio rep 1 | 0.98; 1.20 | Dec. 8, 2016 |
| SAMN06619438 | PE150 | 5C5iL2_R1_001.fastq.gz | 5C5iL2_R2_001.fastq.gz | yHs5C5i1 low MNase experiment 1, bio rep 2 | 0.93; 1.13 | Dec. 8, 2016 |
| SAMN06619439 | PE150 | 5C5iL3_R1_001.fastq.gz | 5C5iL3_R2_001.fastq.gz | yHs5C5i1 low MNase experiment 1, bio rep 3 | 0.93; 1.14 | Dec. 8, 2016 |
| SAMN06619440 | PE150 | 7C5iH1_R1_001.fastq.gz | 7C5iH1_R2_001.fastq.gz | yHs7C5i1 high MNase experiment 1, bio rep 1 | 0.75; 0.86 | Dec. 8, 2016 |
| SAMN06619441 | PE150 | 7C5iH2_R1_001.fastq.gz | 7C5iH2_R2_001.fastq.gz | yHs7C5i1 high MNase experiment 1, bio rep 2 | 0.77; 0.90 | Dec. 8, 2016 |
| SAMN06619442 | PE150 | 7C5iH3_R1_001.fastq.gz | 7C5iH3_R2_001.fastq.gz | yHs7C5i1 high MNase experiment 1, bio rep 3 | 0.77; 0.89 | Dec. 8, 2016 |
| SAMN06619443 | PE150 | 7C5iL1_R1_001.fastq.gz | 7C5iL1_R2_001.fastq.gz | yHs7C5i1 low MNase experiment 1, bio rep 1 | 0.90; 1.06 | Dec. 8, 2016 |
| SAMN06619444 | PE150 | 7C5iL2_R1_001.fastq.gz | 7C5iL2_R2_001.fastq.gz | yHs7C5i1 low MNase experiment 1, bio rep 2 | 0.84; 0.98 | Dec. 8, 2016 |
| SAMN06619445 | PE150 | 7C5iL3_R1_001.fastq.gz | 7C5iL3_R2_001.fastq.gz | yHs7C5i1 low MNase experiment 1, bio rep 3 | 0.79; 0.82 | Dec. 8, 2016 |

TABLE 9-continued

Illumina high-throughput MNase DNA sequencing files

| SRA accession | Type | File name 1 | File name 2 | Description | Filesize (Gb) | Date |
|---|---|---|---|---|---|---|
| SAMN06619446 | PE150 | 97H1_R1_001.fastq.gz | 97H1_R2_001.fastq.gz | yDT97 high MNase experiment 1, bio rep 1 | 0.81; 0.93 | Dec. 8, 2016 |
| SAMN06619447 | PE150 | 97H2_R1_001.fastq.gz | 97H2_R2_001.fastq.gz | yDT97 high MNase experiment 1, bio rep 2 | 0.82; 0.93 | Dec. 8, 2016 |
| SAMN06619448 | PE150 | 97H3_R1_001.fastq.gz | 97H3_R2_001.fastq.gz | yDT97 high MNase experiment 1, bio rep 3 | 0.82; 0.94 | Dec. 8, 2016 |
| SAMN06619449 | PE150 | 97L1_R1_001.fastq.gz | 97L1_R2_001.fastq.gz | yDT97 low MNase experiment 1, bio rep 1 | 0.94; 1.10 | Dec. 8, 2016 |
| SAMN06619450 | PE150 | 97L2_R1_001.fastq.gz | 97L2_R2_001.fastq.gz | yDT97 low MNase experiment 1, bio rep 2 | 0.75; 0.87 | Dec. 8, 2016 |
| SAMN06619451 | PE150 | 97L3_R1_001.fastq.gz | 97L3_R2_001.fastq.gz | yDT97 low MNase experiment 1, bio rep 3 | 0.95; 1.13 | Dec. 8, 2016 |
| SAMN06619452 | PE150 | WTH4_R1_001.fastq.gz | WTH4_R2_001.fastq.gz | yD T67 high MNase experiment 2 | 1.32; 1.53 | Jan. 30, 2017 |
| SAMN06619453 | PE150 | WTL4_R1_001.fastq.gz | WTL4_R2_001.fastq.gz | yD T67 low MNase experiment 2 | 1.31; 1.59 | Jan. 30, 2017 |
| SAMN06619454 | PE150 | 5C5iH4_R1_001.fastq.gz | 5C5iH4_R2_001.fastq.gz | yHs5C5i1 high MNase experiment 2 | 1.31; 1.52 | Jan. 30, 2017 |
| SAMN06619455 | PE150 | 5C5iL4_R1_001.fastq.gz | 5C5iL4_R2_001.fastq.gz | yHs5C5i1 low MNase experiment 2 | 1.50; 1.85 | Jan. 30, 2017 |
| SAMN06619456 | PE150 | 7C5iH4_R1_001.fastq.gz | 7C5iH4_R2_001.fastq.gz | yHs7C5i1 high MNase experiment 2 | 1.16; 1.39 | Jan. 30, 2017 |
| SAMN06619457 | PE150 | 7C5iL4_R1_001.fastq.gz | 7C5iL4_R2_001.fastq.gz | yHs7C5i1 low MNase experiment 2 | 1.30; 1.57 | Jan. 30, 2017 |
| SAMN06619458 | PE150 | 97H4_R1_001.fastq.gz | 97H4_R2_001.fastq.gz | yDT97 high MNase experiment 2 | 1.47; 1.67 | Jan. 30, 2017 |
| SAMN06619459 | PE150 | 97L4_R1_001.fastq.gz | 97L4_R2_001.fastq.gz | yDT97 low MNase experiment 2 | 1.57; 1.87 | Jan. 30, 2017 |

REFERENCES

Acker, J., Conesa, C., and Lefebvre, O. (2013). Yeast RNA polymerase III transcription factors and effectors. Biochim Biophys Acta 1829, 283-295.

Annunziato, A. T. (2005). Split decision: what happens to nucleosomes during DNA replication? J Biol Chem 280, 12065-12068.

Bernstein, E., and Hake, S. B. (2006). The nucleosome: a little variation goes a long way. Biochem Cell Biol 84, 505-517.

Boeke, J. D., Trueheart, J., Natsoulis, G., and Fink, G. R. (1987). 5-Fluoroorotic acid as a selective agent in yeast molecular genetics. Methods Enzymol 154, 164-175.

Bolger, A. M., Lohse, M., and Usadel, B. (2014). Trimmomatic: a flexible trimmer for Illumina sequence data. Bioinformatics 30, 2114-2120.

Brogaard, K., Xi, L., Wang, J. P., and Widom, J. (2012). A map of nucleosome positions in yeast at base-pair resolution. Nature 486, 496-501.

Budhavarapu, V. N., Chavez, M., and Tyler, J. K. (2013). How is epigenetic information maintained through DNA replication? Epigenetics Chromatin 6, 32.

Buschbeck, M., and Hake, S. B. (2017). Variants of core histones and their roles in cell fate decisions, development and cancer. Nat Rev Mol Cell Biol.

Campos, E. I., Smits, A. H., Kang, Y. H., Landry, S., Escobar, T. M., Nayak, S., Ueberheide, B. M., Durocher, D., Vermeulen, M., Hurwitz, J., et al. (2015). Analysis of the Histone H3.1 Interactome: A Suitable Chaperone for the Right Event. Mol Cell 60, 697-709.

Campos, E. I., Stafford, J. M., and Reinberg, D. (2014). Epigenetic inheritance: histone bookmarks across generations. Trends Cell Biol 24, 664-674.

Chen, K., Xi, Y., Pan, X., Li, Z., Kaestner, K., Tyler, J., Dent, S., He, X., and Li, W. (2013). DANPOS: dynamic analysis of nucleosome position and occupancy by sequencing. Genome Res 23, 341-351.

Dai, J., Hyland, E. M., Yuan, D. S., Huang, H., Bader, J. S., and Boeke, J. D. (2008). Probing nucleosome function: a highly versatile library of synthetic histone H3 and H4 mutants. Cell 134, 1066-1078.

DiCarlo, J. E., Norville, J. E., Mali, P., Rios, X., Aach, J., and Church, G. M. (2013). Genome engineering in Saccharomyces cerevisiae using CRISPR-Cas systems. Nucleic Acids Res 41, 4336-4343.

Djebali, S., Davis, C. A., Merkel, A., Dobin, A., Lassmann, T., Mortazavi, A., Tanzer, A., Lagarde, J., Lin, W., Schlesinger, F., et al. (2012). Landscape of transcription in human cells. Nature 489, 101-108.

Eriksson, P. R., Ganguli, D., Nagarajavel, V., and Clark, D. J. (2012). Regulation of histone gene expression in budding yeast. Genetics 191, 7-20.

Fan, Y., Nikitina, T., Zhao, J., Fleury, T. J., Bhattacharyya, R., Bouhassira, E. E., Stein, A., Woodcock, C. L., and Skoultchi, A. I. (2005). Histone H1 depletion in mammals alters global chromatin structure but causes specific changes in gene regulation. Cell 123, 1199-1212.

Floer, M., Wang, X., Prabhu, V., Berrozpe, G., Narayan, S., Spagna, D., Alvarez, D., Kendall, J., Krasnitz, A., Stepansky, A., et al. (2010). A RSC/nucleosome complex determines chromatin architecture and facilitates activator binding. Cell 141, 407-418.

Gibson, D. G., Young, L., Chuang, R. Y., Venter, J. C., Hutchison, C. A., 3rd, and Smith, H. O. (2009). Enzymatic assembly of DNA molecules up to several hundred kilobases. Nat Methods 6, 343-345.

Hage, A. E., and Houseley, J. (2013). Resolution of budding yeast chromosomes using pulsed-field gel electrophoresis. Methods Mol Biol 1054, 195-207.

Hamza, A., Tammpere, E., Kofoed, M., Keong, C., Chiang, J., Giaever, G., Nislow, C., and Hieter, P. (2015). Complementation of Yeast Genes with Human Genes as an Experimental Platform for Functional Testing of Human Genetic Variants. Genetics 201, 1263-1274.

Han, J., Zhang, H., Zhang, H., Wang, Z., Zhou, H., and Zhang, Z. (2013). A Cul4 E3 ubiquitin ligase regulates histone hand-off during nucleosome assembly. Cell 155, 817-829.

Hyland, E. M., Molina, H., Poorey, K., Jie, C., Xie, Z., Dai, J., Qian, J., Bekiranov, S., Auble, D. T., Pandey, A., et al. (2011). An evolutionarily 'young' lysine residue in histone H3 attenuates transcriptional output in Saccharomyces cerevisiae. Genes Dev 25, 1306-1319.

Janke, C., Ortiz, J., Lechner, J., Shevchenko, A., Shevchenko, A., Magiera, M. M., Schramm, C., and Schiebel, E. (2001). The budding yeast proteins Spc24p and Spc25p interact with Ndc80p and Nuf2p at the kinetochore and are important for kinetochore clustering and checkpoint control. EMBO J 20, 777-791.

Kachroo, A. H., Laurent, J. M., Yellman, C. M., Meyer, A. G., Wilke, C. O., and Marcotte, E. M. (2015). Evolution. Systematic humanization of yeast genes reveals conserved functions and genetic modularity. Science 348, 921-925.

Krietenstein, N., Wal, M., Watanabe, S., Park, B., Peterson, C. L., Pugh, B. F., and Korber, P. (2016). Genomic Nucleosome Organization Reconstituted with Pure Proteins. Cell 167, 709-721 e712.

Kubik, S., Bruzzone, M. J., Jacquet, P., Falcone, J. L., Rougemont, J., and Shore, D. (2015). Nucleosome Stability Distinguishes Two Different Promoter Types at All Protein-Coding Genes in Yeast. Mol Cell 60, 422-434.

Kwolek-Mirek, M., and Zadrag-Tecza, R. (2014). Comparison of methods used for assessing the viability and vitality of yeast cells. FEMS Yeast Res 14, 1068-1079.

Lai, W. K. M., and Pugh, B. F. (2017). Understanding nucleosome dynamics and their links to gene expression and DNA replication. Nat Rev Mol Cell Biol.

Laurent, J. M., Young, J. H., Kachroo, A. H., and Marcotte, E. M. (2016). Efforts to make and apply humanized yeast. Brief Funct Genomics 15, 155-163.

Lee, K. P., Baxter, H. J., Guillemette, J. G., Lawford, H. G., and Lewis, P. N. (1982). Structural studies on yeast nucleosomes. Can J Biochem 60, 379-388.

Leung, A., Cheema, M., Gonzalez-Romero, R., Eirin-Lopez, J. M., Ausio, J., and Nelson, C. J. (2016). Unique yeast histone sequences influence octamer and nucleosome stability. FEBS Lett 590, 2629-2638.

Lew, D. J., and Reed, S. I. (1995). A cell cycle checkpoint monitors cell morphogenesis in budding yeast. J Cell Biol 129, 739-749.

Li, H. (2011). A statistical framework for SNP calling, mutation discovery, association mapping and population genetical parameter estimation from sequencing data. Bioinformatics 27, 2987-2993.

Li, H., and Durbin, R. (2010). Fast and accurate long-read alignment with Burrows-Wheeler transform. Bioinformatics 26, 589-595.

Looke, M., Kristjuhan, K., and Kristjuhan, A. (2011). Extraction of genomic DNA from yeasts for PCR-based applications. Biotechniques 50, 325-328.

Lopez-Serra, L., Kelly, G., Patel, H., Stewart, A., and Uhlmann, F. (2014). The Scc2-Scc4 complex acts in sister chromatid cohesion and transcriptional regulation by maintaining nucleosome-free regions. Nat Genet 46, 1147-1151.

Ma, Y., Kanakousaki, K., and Buttitta, L. (2015). How the cell cycle impacts chromatin architecture and influences cell fate. Front Genet 6, 19.

Macadangdang, B. R., Oberai, A., Spektor, T., Campos, O. A., Sheng, F., Carey, M. F., Vogelauer, M., and Kurdistani, S. K. (2014). Evolution of histone 2A for chromatin compaction in eukaryotes. Elife 3.

McBurney, K. L., Leung, A., Choi, J. K., Martin, B. J., Irwin, N. A., Bartke, T., Nelson, C. J., and Howe, L. J. (2016). Divergent Residues Within Histone H3 Dictate a Unique Chromatin Structure in Saccharomyces cerevisiae. Genetics 202, 341-349.

Mi, H., Poudel, S., Muruganujan, A., Casagrande, J. T., and Thomas, P. D. (2016). PANTHER version 10: expanded protein families and functions, and analysis tools. Nucleic Acids Res 44, D336-342.

Mitchell, L. A., Phillips, N. A., Lafont, A., Martin, J. A., Cutting, R., and Boeke, J. D. (2015). qPCRTag Analysis—A High Throughput, Real Time PCR Assay for Sc2.0 Genotyping. J Vis Exp, e52941.

Nakanishi, S., Sanderson, B. W., Delventhal, K. M., Bradford, W. D., Staehling-Hampton, K., and Shilatifard, A. (2008). A comprehensive library of histone mutants identifies nucleosomal residues required for H3K4 methylation. Nat Struct Mol Biol 15, 881-888.

Osborn, M. J., and Miller, J. R. (2007). Rescuing yeast mutants with human genes. Brief Funct Genomic Proteomic 6, 104-111.

Panday, A., and Grove, A. (2016). The high mobility group protein HMO1 functions as a linker histone in yeast. Epigenetics Chromatin 9, 13.

Pavelka, N., Rancati, G., Zhu, J., Bradford, W. D., Saraf, A., Florens, L., Sanderson, B. W., Hattem, G. L., and Li, R. (2010). Aneuploidy confers quantitative proteome changes and phenotypic variation in budding yeast. Nature 468, 321-325.

Quinlan, A. R. (2014). BEDTools: The Swiss-Army Tool for Genome Feature Analysis. Curr Protoc Bioinformatics 47, 11 12 11-34.

Radman-Livaja, M., Verzijlbergen, K. F., Weiner, A., van Welsem, T., Friedman, N., Rando, O. J., and van Leeuwen, F. (2011). Patterns and mechanisms of ancestral histone protein inheritance in budding yeast. PLoS Biol 9, e1001075.

Rando, O. J., and Winston, F. (2012). Chromatin and transcription in yeast. Genetics 190, 351-387.

Rosebrock, A. P. (2017). Analysis of the Budding Yeast Cell Cycle by Flow Cytometry. Cold Spring Harb Protoc 2017, pdb prot088740.

Sanchez-Perez, I., Renwick, S. J., Crawley, K., Karig, I., Buck, V., Meadows, J. C., Franco-Sanchez, A., Fleig, U., Toda, T., and Millar, J. B. (2005). The DASH complex and Klp5/Klp6 kinesin coordinate bipolar chromosome attachment in fission yeast. EMBO J 24, 2931-2943.

Santenard, A., and Torres-Padilla, M. E. (2009). Epigenetic reprogramming in mammalian reproduction: contribution from histone variants. Epigenetics 4, 80-84.

Segal, E., and Widom, J. (2009). What controls nucleosome positions? Trends Genet 25, 335-343.

Sheltzer, J. M., Blank, H. M., Pfau, S. J., Tange, Y., George, B. M., Humpton, T. J., Brito, I. L., Hiraoka, Y., Niwa, O., and Amon, A. (2011). Aneuploidy drives genomic instability in yeast. Science 333, 1026-1030.

Shen, L., Shao, N., Liu, X., and Nestler, E. (2014). ngs.plot: Quick mining and visualization of next-generation sequencing data by integrating genomic databases. BMC Genomics 15, 284.

Szklarczyk, D., Franceschini, A., Wyder, S., Forslund, K., Heller, D., Huerta-Cepas, J., Simonovic, M., Roth, A., Santos, A., Tsafou, K. P., et al. (2015). STRING v10:

protein-protein interaction networks, integrated over the tree of life. Nucleic Acids Res 43, D447-452.

Talbert, P. B., and Henikoff, S. (2010). Histone variants—ancient wrap artists of the epigenome. Nat Rev Mol Cell Biol 11, 264-275.

Talbert, P. B., and Henikoff, S. (2017). Histone variants on the move: substrates for chromatin dynamics. Nat Rev Mol Cell Biol 18, 115-126.

Thurman, R. E., Rynes, E., Humbert, R., Vierstra, J., Maurano, M. T., Haugen, E., Sheffield, N. C., Stergachis, A. B., Wang, H., Vernot, B., et al. (2012). The accessible chromatin landscape of the human genome. Nature 489, 75-82.

Toyama, B. H., Savas, J. N., Park, S. K., Harris, M. S., Ingolia, N. T., Yates, J. R., 3rd, and Hetzer, M. W. (2013). Identification of long-lived proteins reveals exceptional stability of essential cellular structures. Cell 154, 971-982.

Valouev, A., Johnson, S. M., Boyd, S. D., Smith, C. L., Fire, A. Z., and Sidow, A. (2011). Determinants of nucleosome organization in primary human cells. Nature 474, 516-520.

Veatch, J. R., McMurray, M. A., Nelson, Z. W., and Gottschling, D. E. (2009). Mitochondrial dysfunction leads to nuclear genome instability via an iron-sulfur cluster defect. Cell 137, 1247-1258.

Wen, D., Banaszynski, L. A., Liu, Y., Geng, F., Noh, K. M., Xiang, J., Elemento, O., Rosenwaks, Z., Allis, C. D., and Rafii, S. (2014). Histone variant H3.3 is an essential maternal factor for oocyte reprogramming. Proc Natl Acad Sci USA 111, 7325-7330.

White, C. L., Suto, R. K., and Luger, K. (2001). Structure of the yeast nucleosome core particle reveals fundamental changes in internucleosome interactions. EMBO J 20, 5207-5218.

Woodcock, C. L., Skoultchi, A. I., and Fan, Y. (2006). Role of linker histone in chromatin structure and function: H1 stoichiometry and nucleosome repeat length. Chromosome Res 14, 17-25.

Zhang, T., Lei, J., Yang, H., Xu, K., Wang, R., and Zhang, Z. (2011). An improved method for whole protein extraction from yeast *Saccharomyces cerevisiae*. Yeast 28, 795-798.

Although the embodiments have been described in detail for the purposes of illustration, it is understood that such detail is solely for that purpose, and variations can be made therein by those skilled in the art without departing from the spirit and scope of the disclosure, embodiments of which are defined by the following sample claims.

What is claimed is:

1. A modified yeast comprising: i) a mutated yeast DAD1 gene, the mutated DAD1 gene encoding an E50D mutation in yeast DAD1 protein such that the DAD1 gene encodes an amino acid sequence comprising the amino acid sequence of SEQ ID NO:20, and ii) an H3 histone sequence comprising the amino acid sequence of SEQ ID NO:17.

2. A yeast cell of the modified yeast of claim 1, wherein the yeast cell is fused to a non-yeast eukaryotic cell.

3. The yeast cell of claim 2, wherein the non-yeast eukaryotic cell is a non-yeast fungal cell.

4. The yeast cell of claim 2 wherein the non-yeast eukaryotic cell is an animal cell.

5. The yeast cell of claim 2, wherein the non-yeast eukaryotic cell is a mammalian cell, wherein the mammalian cell is optionally a human or porcine cell.

* * * * *